(12) United States Patent
Coffen et al.

(10) Patent No.: US 6,355,641 B1
(45) Date of Patent: Mar. 12, 2002

(54) OXAZOLONE DERIVATIVES AND USES THEREOF

(75) Inventors: David Llewellyn Coffen, San Diego; Michael Patrick Dillon, San Carlos; Anthony P. D. W. Ford, Mountain View; Zhe Li, San Diego; Timothy James Williams, Sunnyvale, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/521,185

(22) Filed: Mar. 8, 2000

Related U.S. Application Data

(60) Provisional application No. 60/124,781, filed on Mar. 17, 1999, and provisional application No. 60/165,312, filed on Nov. 12, 1999.

(51) Int. Cl.[7] ..................... A61K 31/496; C07D 413/06
(52) U.S. Cl. ................. 514/252.18; 514/254.02; 544/328; 544/331; 544/364; 544/369
(58) Field of Search ................. 544/328, 331, 544/364, 369; 514/252.18, 254.02

(56) References Cited

U.S. PATENT DOCUMENTS

| | | | |
|---|---|---|---|
| 5,736,412 A | 4/1998 | Zambias et al. | 536/918 |
| 5,859,014 A | 1/1999 | Bantle et al. | 514/255 |
| 5,962,736 A | 10/1999 | Zambias et al. | 564/152 |

FOREIGN PATENT DOCUMENTS

| | | |
|---|---|---|
| DE | 117 224 | 1/1975 |
| DE | 117 225 | 1/1975 |
| DE | 117 228 | 1/1975 |
| DE | 26 59 543 A1 | 7/1978 |
| EP | 0 602 851 A1 | 6/1994 |
| JP | 8-27132 | 1/1996 |
| WO | WO 95/17903 | 7/1995 |
| WO | WO 95/25726 | 9/1995 |
| WO | WO 96/16049 | 5/1996 |
| WO | WO 98/46551 | 10/1998 |
| WO | WO 98/46559 | 10/1998 |
| WO | WO 98/56028 | 12/1998 |
| WO | WO 99/09829 | 3/1999 |
| WO | WO 99/09979 | 3/1999 |
| WO | WO 99/09980 | 3/1999 |

OTHER PUBLICATIONS

Giardina et al., "Synthesis and Biological Profile of the Enantiomers of [4-(4-Amino-6,7-Dimethoxyquinazolin-2-yl)-cis-Octahydroquinoxalin-1-yl]Furan-2-ylmethanone (Cyclazosin), a Potent Competitive $\alpha_{1B}$-Adrenoceptor Antagonist," *J. Med. Chem. 39*: 4602–4607 (1996).

Patane et al., "4-Amino-2-[4-[1-(Benzyloxcarbonyl)-2(S)-[(1,1-Dimethylethyl)Amino]Carbonyl]-Piperazinyl]-6,7-Dimethoxyquinazoline (L-765,314): A Potent and Selective $\alpha_{1B}$ Adrenergic Receptor Antagonist," *Journal of Medicinal Chemistry 41*(8):1205–1208 (1998).

Xie et al., "Increase In $\alpha_{1B}$ Adrenergic Receptor mRNA Expression in the Rat Dorsal Root Ganglion (DRG) After Spinal Nerve Injury," *Society For Neuroscience Abstract 24*:2089 (1998).

Lee et al, "Receptor Subtype Mediating the Adreberguc Receptor of Pain Behavior and Ectopic Discharges in Neuropathic Lewis Rats," *American Physiological Society* 2226–2233 (1999).

*Primary Examiner*—Richard L. Raymond
(74) *Attorney, Agent, or Firm*—Gloria Pfister; Vandana Date

(57) ABSTRACT

This invention relates to compounds which are generally alpha$_{1B}$-receptor antagonists, and which are represented by Formula (I):

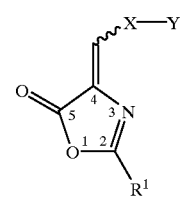

(I)

wherein X, Y, and R[1] are as defined in the specification, or individual isomers or racemic or non-racemic mixtures of isomers, or pharmaceutically acceptable salts or solvates thereof. The invention further relates to pharmaceutical compositions containing such compounds, and methods for their use as therapeutic agents.

30 Claims, No Drawings

OXAZOLONE DERIVATIVES AND USES THEREOF

CROSS-REFERENCE TO RELATED APPLICATIONS

This application claims benefit under Title 35 U.S.C. 119(e) of U.S. Provisional Application No. 60/124,781; filed Mar. 17, 1999 and No. 60/165,312, filed Nov. 12, 1999; and makes reference to the commonly owned U.S. patent application Ser. No. 60/124,721 by Ford et al. entitled "A Method For Screening Compounds For Alpha$_{1B}$ Adrenergic Receptor Antagonist and Analgesic Activity," filed on Mar. 17, 1999; all three applications are hereby incorporated by reference in its entirety.

TECHNICAL FIELD

The invention relates generally to oxazolone derivatives, and pharmaceutically acceptable salts or solvates thereof, which exhibit useful pharmacological properties. In particular, the invention relates to compounds, pharmaceutical compositions and methods of using oxazolone derivatives as alpha$_1$-adrenergic receptor (alpha$_1$-adrenoceptor) modulators, preferably antagonists.

BACKGROUND OF THE INVENTION

Alpha1-adrenergic receptors are G-protein coupled transmembrane receptors that mediate various actions of the sympathetic nervous system through the binding of the catecholamines, epinephrine and norepinephrine. Currently, several subtypes of the alpha$_1$-adrenergic receptors are known to exist for which the genes have been cloned: alpha$_{1A}$ (previously known as alpha$_{1C}$), alpha$_{1B}$ and alpha$_{1D}$. The existence of an additional subtype, the alpha$_{1L}$-adrenergic receptor subtype, has been proposed; however, the gene for the alpha$_{1L}$-adrenergic receptor subtype has yet to be cloned. Although these subtypes can be pharmacologically distinguished, existing subtype-selective compounds are only moderately specific and may interact with more than one alpha$_1$-adrenergic receptor subtype. Accordingly, therapeutic use of nonselective alpha$_1$-adrenergic receptor antagonists must be carefully monitored as such antagonists can produce significant undesirable side effects such as postural hypotension, sedation or depression, increased gastrointestinal motility and diarrhea, impaired ability to ejaculate, nasal stuffiness, akinesia and the like.

Non-selective alpha$_1$-adrenoceptor antagonists have been used to treat lower urinary tract symptoms associated with benign prostatic hyperplasia (BPH). Further, alpha$_1$-adrenoceptor antagonists can be effective in reducing or alleviating urinary tract disorders and/or the symptoms thereof, such as pelvic hypersensitivity, overactive bladder, urinary frequency, nocturia, urinary urgency, detrusor hyperreflexia, outlet obstruction, prostatitis, incontinence, urge incontinence, urethritis, prostatodynia, idiopathic bladder hypersensitivity, and the like.

Compounds that interact more selectively with a particular alpha$_1$-adrenergic receptor subtype may prove clinically useful in providing more selective treatment of conditions and diseases, and symptoms thereof, associated with activity at the receptor subtype. For example, alpha$_1$-adrenergic receptor antagonists that can selectively reduce or alleviate urinary tract disorders or symptoms, or ameliorate nociceptive and/or neurogenic pain without affecting blood pressure or causing postural hypotension, are desirable. Presently available alpha$_1$-adrenergic antagonists are either relatively nonselective with respect to the subtypes with which they interact or generally are not selective for the alpha$_{1B}$-adrenergic receptor subtype.

DESCRIPTION OF THE RELATED ART

U.S. Pat. No. 5,736,412 (Zambias et al.) refers to a method of generating a plurality of certain chemical compounds in a spatially arranged array.

U.S. Pat. No. 5,962,736 (Zambias et al.) refers to logically ordered arrays of compounds and methods of making and using the same.

U.S. Pat. No. 5,859,014 (Bantle et al.) refers to certain pyrimidinedione, pyrimidinetrione, triazinedione and tetrahydroquinazolinedione derivatives which are disclosed as being useful as alpha1 adrenergic receptor antagonists.

PCT Published Application WO 95/17903 (assigned to Arqule) refers to a modular design and synthesis of oxazolone-derived molecules.

PCT Published Application WO 95/25726 (assigned to Recordati) refers to certain quinazolyl-amino derivatives which are disclosed as having alpha antagonist activity.

PCT Published Application WO 98/46551 (assigned to Arqule) refers to a synthesis and use of certain biased arrays.

PCT Published Application WO 98/46559 (assigned to Arqule) refers to a synthesis and use of certain alpha-ketoamide derivatives and arrays.

PCT Published Application WO 98/56028 (assigned to Arqule) refers to an automated, highthroughput method for screening a plurality of compounds using mass spectrometry.

PCT Published Application WO 96/16049 (assigned to Glaxo) refers to certain oxazoles as alpha-1C antagonists.

PCT Published Applications WO 99/09979, WO 99/09980, and WO 99/09829 (all assigned to Eli Lilly) refer to certain oxazoles for treating neuropathic pain.

European Patent Application EP 602851 refers to certain quinazoline derivatives.

German Patent Publications No. 117 224, 117 225, 117 228, and DE 2 659 543 refer to synthesis of certain oxazolinones.

Japanese Patent Application No 08-27132 refers to the preparation of certain oxazolones.

Giardina et al., J. Med. Chem. 1996, 39, 4602–4607 refer to the synthesis of cyclazosin enantiomers and their activity as alpha-1B antagonists.

Patane et al., J. Med. Chem 1998, 41, 1206–1208 refer to L-765314 as a potent and selective alpha-1B antagonist.

Xie et al., Soc. for Neuroscience Abstract 24, 2089(1998) refer to certain alpha 1B adrenergic receptor mRNA expression in rat DRG after spinal nerve injury.

Lee et al, J. Neurophysiol. 81, 2226–2233 (1999) refer to certain receptor subtypes mediating the adrenergic sensitivity of pain behaviour.

SUMMARY OF THE INVENTION

The present invention addresses the aforementioned needs in the art by providing oxazolone derivatives, and pharmaceutically acceptable salts or solvates thereof, which exhibit useful pharmacological properties. Particularly, the present invention relates to oxazolone derivatives, pharmaceutical compositions thereof and methods of using such derivatives as alpha$_1$-adrenergic receptor (alpha$_1$-adrenoceptor) modulators, preferably antagonists.

In one embodiment, the invention relates to a compound comprising the Formula (I):

(I)

wherein:

X is Formula (A), (B) or (C);

(A)

(B)

(C)

m is an integer ranging from 1 to 6 inclusive;

n is an integer ranging from 0 to 5 inclusive;

p, q, r and s are each independently integers ranging from 1 to 3 inclusive, with the proviso that when p is greater than one, r is 1 and when s is greater than one, q is 1;

Y is —$(CH_2)_w$—$R^3$, —$(CH_2)_w$—CO—$R^4$, —$(CH_2)_w$—CO—NH—$R^5$, —$(CH_2)_w$—C($NR^6$)—NH—$R^7$, —$(CH_2)_w$—$SO_2$—$R^8$, —$(CH_2)_w$—NH—$R^9$, —$(CH_2)_w$—NH—CO—$R^{10}$, —$(CH_2)_w$—NH—CO—NH—$R^{11}$, or —$(CH_2)_w$—NH—$SO_2$—$R^{12}$; wherein w is an integer ranging from 0 to 3 inclusive;

Z is CH or N;

$R^1$ is cycloalkyl, cycloalkenyl, heterocyclic, aryl or heteroaryl;

$R^{2a}$, $R^{2b}$ or $R^{2c}$ are each independently in each occurrence hydrogen, alkyl, alkenyl, cycloalkyl, aryl, or arylalkyl; or $R^{2a}$ and $R^{2b}$ taken together with the carbons to which they are attached form a 5- to 7-membered ring structure;

$R^3$ is heterocyclic or heteroaryl;

$R^4$, $R^5$, $R^8$, $R^9$, $R^{10}$, $R^{11}$ and $R^{12}$ are each independently in each occurrence hydrogen, alkyl, alkoxy, hydroxyalkyl, alkylthio, alkenyl, cycloalkyl, cycloalkylalkyl, cycloalkenyl, cycloalkenylalkyl, heterocyclic, heterocyclicalkyl, aryl, arylalkyl, heteroaryl, or heteroarylalkyl;

$R^6$ and $R^7$ are each independently in each occurrence hydrogen, alkyl, hydroxyalkyl, alkenyl, cycloalkyl, cycloalkylalkyl, cycloalkenyl, cycloalkenylalkyl, heterocyclic, heterocyclicalkyl, aryl, arylalkyl, heteroaryl, or heteroarylalkyl;

or individual isomers or racemic or non-racemic mixtures of isomers, or pharmaceutically acceptable salts or solvates thereof.

In a preferred embodiment, X is:

or individual isomers or racemic or non-racemic mixtures of isomers, or pharmaceutically acceptable salts or solvates thereof.

In a more preferred embodiment, X is piperazinyl or piperidinyl; or individual isomers or racemic or non-racemic mixtures of isomers, or pharmaceutically acceptable salts or solvates thereof. Even more preferably X is piperazinyl; or individual isomers or racemic or non-racemic mixtures of isomers, or pharmaceutically acceptable salts or solvates thereof.

In a preferred embodiment, Y is —$(CH_2)_w$—$R^3$, —$(CH_2)_w$—CO—$R^4$, —$(CH_2)_w$—CO—NH—$R^5$, —$(CH_2)_w$—C($NR^6$)—NH—$R^7$, —$(CH_2)_w$—$SO_2$—$R^8$, —$(CH_2)_w$—NH—$R^9$, —$(CH_2)_w$—NH—CO—$R^{10}$, —$(CH_2)_w$—NH—CO—NH—$R^{11}$, or —$(CH_2)_w$—NH—$SO_2$—$R^{12}$; or individual isomers or racemic or non-racemic mixtures of isomers, or pharmaceutically acceptable salts or solvates thereof.

In another preferred embodiment, Y is —$(CH_2)_w$—CO—$R^4$, —$(CH_2)_w$—$SO_2$—$R^8$, —$(CH_2)_w$—NH—$R^9$, —$(CH_2)_w$—NH—CO—$R^{10}$, —$(CH_2)_w$—NH—CO—NH—$R^{11}$, or —$(CH_2)_w$—NH—$SO_2$—$R^{12}$; or individual isomers or racemic or non-racemic mixtures of isomers, or pharmaceutically acceptable salts or solvates thereof.

In another preferred embodiment, Y is —$(CH_2)_w$—$R^3$; or individual isomers or racemic or non-racemic mixtures of isomers, or pharmaceutically acceptable salts or solvates thereof.

In another preferred embodiment, Y is —$(CH_2)_w$—CO—NH—$R^5$; or individual isomers or racemic or non-racemic mixtures of isomers, or pharmaceutically acceptable salts or solvates thereof.

In another preferred embodiment, Y is —$(CH_2)_w$—C($NR^6$)—NH—$R^7$; or individual isomers or racemic or non-racemic mixtures of isomers, or pharmaceutically acceptable salts or solvates thereof.

In another preferred embodiment, $R^1$ is aryl or heteroaryl; more preferably $R^1$ is an alkyl-, halo- or alkoxy-substituted phenyl, a bicyclic aryl or a bicyclic heteroaryl; and even more preferably $R^1$ is a 3-substituted phenyl (e.g., 3-methylphenyl, 3-chlorophenyl, 3-methoxyphenyl), naphthyl, fluoronaphthyl, thianaphthenyl(benzothiophenyl), benzofuranyl, quinolinyl, indolyl, fluorobenzofuranyl, or benzimidazolyl; or individual isomers or racemic or non-racemic mixtures of isomers, or pharmaceutically acceptable salts or solvates thereof.

In another preferred embodiment, $R^3$ is a moiety selected from benzooxazolyl, pyrazolyl, pyrimidyl, pyrrolyl, quinolinyl, isoquinolinyl, benzoisoquinolinyl dione, indolyl, imidazolyl, benzimidazolyl, imidazopyridinyl, oxazolyl, isooxazolyl, quinoxanilyl, thiazolyl, benzothiazolyl, or thiazolidinyl; wherein the moiety is optionally substituted with one or more of the following substituents: hydroxy, cyano, alkyl, alkoxy, thioalkyl, halo, haloalkyl, trifluoromethyl, hydroxyalkyl, alkoxycarbonyl, nitro, amino, alkylamino, dialkylamino, cycloalkyl, cycloalkylenyl, heterocyclic, aryl or heteroaryl; or individual isomers or racemic or non-racemic mixtures of isomers, or pharmaceutically acceptable salts or solvates thereof.

In another preferred embodiment, $R^4$ is alkyl, alkoxy, cycloalkyl, aryl, arylalkyl, heteroaryl, or heteroarylalkyl; or individual isomers or racemic or non-racemic mixtures of isomers, or pharmaceutically acceptable salts or solvates thereof.

In another preferred embodiment, $R^5$ is alkyl, cycloalkyl, heterocyclicalkyl, aryl, arylalkyl, or heteroaryl; or individual isomers or racemic or non-racemic mixtures of isomers, or pharmaceutically acceptable salts or solvates thereof.

In another preferred embodiment, $R^6$ is hydrogen or alkyl; or individual isomers or racemic or non-racemic mixtures of isomers, or pharmaceutically acceptable salts or solvates thereof.

In another preferred embodiment, $R^7$ is hydrogen, alkyl, cycloalkyl, aryl, arylalkyl, or heteroaryl; or individual isomers or racemic or non-racemic mixtures of isomers, or pharmaceutically acceptable salts or solvates thereof.

In another preferred embodiment, $R^8$ is alkyl, aryl, arylalkyl, or heteroaryl; or individual isomers or racemic or non-racemic mixtures of isomers, or pharmaceutically acceptable salts or solvates thereof.

In another preferred embodiment, $R^9$ is alkyl, arylalkyl, or heteroarylalkyl; or individual isomers or racemic or non-racemic mixtures of isomers, or pharmaceutically acceptable salts or solvates thereof.

In another preferred embodiment, $R^{10}$ is alkyl, alkoxy, cycloalkyl, aryl, arylalkyl, heteroaryl, or heteroarylalkyl; or individual isomers or racemic or non-racemic mixtures of isomers, or pharmaceutically acceptable salts or solvates thereof.

In another preferred embodiment, $R^{11}$ is alkyl, cycloalkyl, heterocyclicalkyl, aryl, arylalkyl, or heteroaryl; or individual isomers or racemic or non-racemic mixtures of isomers, or pharmaceutically acceptable salts or solvates thereof.

In another preferred embodiment, $R^{12}$ is alkyl, aryl, arylalkyl, or heteroaryl; or individual isomers or racemic or non-racemic mixtures of isomers, or pharmaceutically acceptable salts or solvates thereof.

In an additional embodiment, the invention relates to a pharmaceutical composition comprising a therapeutically effective amount of at least one compound of Formula (I), or individual isomers or racemic or non-racemic mixtures of isomers, or pharmaceutically acceptable salts or solvates thereof as described herein. In another embodiment, at least one compound of Formula (I), or individual isomers or racemic or non-racemic mixtures of isomers, or pharmaceutically acceptable salts or solvates thereof as described herein, is an $alpha_1$-adrenoceptor modulator. In a preferred embodiment at least one compound is an $alpha_1$-adrenoceptor antagonist. In a more preferred embodiment, at least one compound of Formula (I), or individual isomers or racemic or non-racemic mixtures of isomers, or pharmaceutically acceptable salts or solvates thereof as described herein is an $alpha_{1B}$-adrenoceptor antagonist.

In another embodiment, the invention relates to a method of treating a disease state alleviable by treatment with an $alpha_1$-adrenoceptor modulator. In a preferred embodiment, the invention relates to a method of treating a disease state alleviable by treatment with an $alpha_1$-adrenoceptor antagonist, such as disease states of the urinary tract such as incontinence, benign prostatic hypertrophy, prostatitis, detrusor hyperreflexia, urinary frequency, nocturia, urinary urgency, overactive bladder, pelvic hypersensitivity (including interstitial cystitis, prostatitis, pelvic pain syndrome, infectious cystitis, prostatodynia, and the like), urge incontinence, urethritis, or idiopathic bladder hypersensitivity; male erectile dysfunction and female sexual dysfunction; pain including acute pain, inflammatory pain, neuropathic pain and complex regional pain syndromes; hypertension and cardiac dysfunctions resulting from altered contractility, and/or hypertrophy.

In a preferred embodiment, the disease state comprises disorders of the urinary tract, preferably the disease state is incontinence, benign prostatic hypertrophy, prostatitis, detrusor hyperreflexia, urinary frequency, nocturia, urinary urgency, overactive bladder, pelvic hypersensitivity, urge incontinence, urethritis, prostatodynia, cystitis or idiopathic bladder hypersensitivity.

In a preferred embodiment, the disease state is male erectile dysfunction or female sexual dysfunction.

In another preferred embodiment, the disease state is pain, preferably inflammatory pain, neuropathic pain, cancer pain, acute pain, chronic pain or complex regional pain syndromes.

In an additional embodiment, the invention relates to a method of treating a subject which comprises administering to the subject a therapeutically effective amount of at least one compound of Formula (I), or individual isomers or racemic or non-racemic mixtures of isomers, or pharmaceutically acceptable salts or solvates thereof as described herein or a pharmaceutical composition thereof as described herein. In a preferred embodiment, the subject has a disease state alleviable by treatment with an $alpha_1$-subtype adrenoceptor modulator, preferably an antagonist, more preferably an $alpha_{1B}$-adrenoceptor antagonist.

These and other embodiments of the present invention will readily occur to those of ordinary skill in the art in view of the disclosure herein.

DETAILED DESCRIPTION

The practice of the present invention will employ, unless otherwise indicated, conventional methods of chemistry, biochemistry and pharmacology, within the skill of the art. Such techniques are explained fully in the literature. See, e.g., *Remington's Pharmaceutical Sciences,* 19th Edition (Easton, Pa.: Mack Publishing Company, 1995); *Methods In Enzymology* (S. Colowick and N. Kaplan, eds., Academic Press, Inc.); *Textbook of Pain* (P. D. Wall and R. Melzack, editors, Third Edition, Churchill Livingstone, 1994); *Fieser and Fieser's Reagents for Organic Synthesis,* Wiley & Sons, New York, 1991, Volumes 1–15; *Rodd's Chemistry of Car-* bon Compounds, Elsevier Science Publishers, 1989, Volumes 1–5 and Supplementals; and Organic Reactions, Wiley & Sons, New York, 1991, Volumes 1–40.

All publications, patents and patent applications cited herein, whether supra or infra, are hereby each incorporated by reference in their entirety.

As used in this specification and the appended claims, the singular forms "a," "an" and "the" include singular and plural references unless the content clearly dictates otherwise. Thus, for example, reference to "an antagonist" may include a mixture of two or more such agents.

I. Definitions

In describing the present invention, the following terms will be employed, and are intended to be defined as indicated below.

"Alkyl" means the monovalent linear or branched saturated hydrocarbon radical, consisting solely of carbon and hydrogen atoms, having from one to twelve carbon atoms inclusive, unless otherwise indicated. Examples of an alkyl radical include, but are not limited to, methyl, ethyl, propyl, isopropyl, n-butyl, isobutyl, sec-butyl, tert-butyl, pentyl, n-hexyl, octyl, dodecyl, and the like.

"Lower alkyl" means the monovalent alkyl radical as defined herein, having from one to six carbon atoms inclusive, unless otherwise indicated. Examples of a lower alkyl radical include, but are not limited to, methyl, ethyl, propyl, isopropyl, n-butyl, isobutyl, tert-butyl, pentyl, n-hexyl and the like.

"Alkylene" means the divalent linear or branched saturated hydrocarbon radical consisting solely of carbon and hydrogen atoms, containing no unsaturation and having from one to six carbons inclusive, unless otherwise indicated. Examples of alkylene radicals include, but are not limited to, methylene, ethylene, propylene, 2-methylpropylene, butylene, 2-ethylbutylene, and the like.

"Alkenyl" means the monovalent linear or branched unsaturated hydrocarbon radical, consisting solely of carbon and hydrogen atoms, containing a double bond and having from two to six carbon atoms inclusive, unless otherwise indicated. Examples of an alkenyl radical include, but are not limited to, ethenyl, allyl, 1-propenyl, 2-butenyl, and the like.

"Alkynyl" means the monovalent linear or branched unsaturated hydrocarbon radical, consisting solely of carbon and hydrogen atoms, containing a triple bond and having from two to six carbon atoms inclusive, unless otherwise indicated. Examples of an alkynyl radical include, but are not limited to, ethynyl, 1-propynyl, 2-butynyl, and the like.

"Alkoxy" means the radical —O—R, wherein R is a lower alkyl radical as defined herein. Examples of an alkoxy radical include, but are not limited to, methoxy, ethoxy, isopropoxy, and the like.

"Alkoxycarbonyl" means the radical R—O—C(O)—, wherein R is a lower alkyl radical as defined herein. Examples of an alkoxycarbonyl radical include, but are not limited to, methoxycarbonyl, ethoxycarbonyl, sec-butoxycarbonyl, and the like.

"Acyloxy" means the radical —OC(O)R, wherein R is a lower alkyl radical as defined herein. Examples of acyloxy radicals include, but are not limited to, acetoxy, propionyloxy, and the like.

"Acyl" or "alkanoyl" means the radical —C(O)—R wherein R is a lower alkyl as defined herein. Examples of acyl radicals include, but are not limited to, formyl, acetyl, propionyl, butyryl, and the like.

"Alkylamino" means the radical —NHR, wherein R is a lower alkyl radical as defined herein. Examples of alkylamino radicals include, but are not limited to, methylamino, (1-ethylethyl)amino, and the like.

"Aminoalkyl" means the radical —RNR'R", wherein R is a lower alkyl radical as defined herein, and R' and R" are each independently H or a lower alkyl radical as defined herein. Examples of aminoalkyl radicals include, but are not limited to, aminomethyl, aminoethyl, aminopropyl, and the like.

"Alkylthio" means the radical —SR, wherein R is a lower alkyl radical as defined herein. Examples of alkylthio radicals include, but are not limited to, methylthio, butylthio, and the like.

"Dialkylamino" means the radical —NR'R", wherein R' and R" are each independently lower alkyl radicals as defined herein. Examples of dialkylamino radicals include, but are not limited to, dimethylamino, methylethylamino, diethylamino, di(1-methylethyl)amino, and the like.

"Aryl" means the monovalent monocyclic aromatic hydrocarbon radical consisting of one or more fused rings in which at least one ring is aromatic in nature, which can optionally be substituted with one or more of the following substituents: hydroxy, cyano, alkyl, alkoxy, thioalkyl, halo, haloalkyl, trifluoromethyl, hydroxyalkyl, alkoxycarbonyl, nitro, amino, alkylamino, dialkylamino, aminocarbonyl, carbonylamino, aminosulfonyl and sulfonylamino, unless otherwise indicated. Examples of aryl radicals include, but are not limited to, phenyl, naphthyl, biphenyl, diphenylmethyl, 9H-fluorenyl, indanyl, anthraquinolyl, and the like.

"Heteroaryl" means the monovalent aromatic carbocyclic radical having one or more rings incorporating one, two, or three heteroatoms within the ring (chosen from nitrogen, oxygen, or sulfur) which can optionally be substituted with one or more of the following substituents: hydroxy, cyano, alkyl, alkoxy, thioalkyl, halo, haloalkyl, trifluoromethyl, hydroxyalkyl, alkoxycarbonyl, nitro, amino, alkylamino, dialkylamino, aminocarbonyl, carbonylamino, aminosulfonyl and sulfonylamino, unless otherwise indicated. Examples of heteroaryl radicals include, but are not limited to, naphtyridinyl, anthranilyl, benzooxazolyl, pyridyl, pyrrolyl, pyrazolyl, pyrazinyl, pyrimidyl, thiophenyl, furanyl, benzofuranyl, dihydrobenzofuranyl, 3,3-dimethyl-2,3-dihydrobenzofuranyl, quinolinyl, isoquinolinyl, tetrahydroquinolinyl, 1,2,3,4-tetrahydroquinolinyl, 1,2,3,4-tetrahydroisoquinolinyl, tetrahydroquinoxalinyl, benzodioxazolyl, benzoisoquinolinyl dione, benzodioxanyl, indolyl, 2,3-dihydroindolyl, thianaphthenyl, dihydrothianaphthenyl, imidazolyl, benzoimidazolyl, benzimidazolyl, azabenzimidazolyl, oxazolyl, isooxazolyl, quinoxalinyl, thiazolyl, benzothiazolyl, thiazolidinyl, pyranyl, tetrahydropyranyl pyranyl, benzo[1,3]dioxolyl, 2,3-dihydrobenzo[1,4]dioxinyl, thienyl, benzo[b]thienyl, 1,2,3,4-tetrahydro[1,5]naphthyridinyl, 2H-3,4-dihydrobenzo[1,4]oxazine, 4,5-dihydro-1H-imidazol-2-yl, and the like.

"Arylalkyl" means the radical R'R"—, wherein R' is an aryl or heteroaryl radical as defined herein, and R" is an alkyl radical as defined herein. Examples of arylalkyl radicals include, but are not limited to, benzyl, phenylethyl, 3-phenylpropyl, and the like.

"Cycloalkyl" means the monovalent saturated carbocyclic radical consisting of one or more rings, which can optionally be substituted with one or more of the following substituents: hydroxy, cyano, alkyl, alkoxy, thioalkyl, halo, haloalkyl, trifluoromethyl, hydroxyalkyl, alkoxycarbonyl, nitro, amino, alkylamino, dialkylamino, aminocarbonyl, carbonylamino, aminosulfonyl and sulfonylamino, unless otherwise indicated. Examples of cycloalkyl radicals include, but are not limited to, cyclopropyl, cyclobutyl, 3-ethylcyclobutyl, cyclopentyl, cyclohexyl, cycloheptyl, hydrogenated derivatives of aryl as defined herein, and the like.

"Cycloalkylalkyl" means the radical R'R"—, wherein R' is a cycloalkyl radical as defined herein and R" is an alkyl radical as defined herein. Examples of cycloalkylalkyl radicals include, but are not limited to, cyclopropylmethyl, cyclohexylmethyl, 3-ethylcyclobutyl, cyclopentylethyl, and the like.

"Cycloalkenyl" means the monovalent unsaturated carbocyclic radical consisting of one or more rings, which can optionally be substituted with one or more of the following substituents: hydroxy, cyano, alkyl, alkoxy, thioalkyl, halo, haloalkyl, trifluoromethyl, hydroxyalkyl, alkoxycarbonyl, nitro, amino, alkylamino, dialkylamino, aminocarbonyl, carbonylamino, aminosulfonyl and sulfonylamino, unless otherwise indicated. Examples of cycloalkenyl radicals include, but are not limited to, cyclopentenyl, cyclohexenyl, cycloheptenyl, hydrogenated derivatives of aryl as defined herein, and the like.

"Heterocyclyl" means the monovalent saturated carbocyclic radical, consisting of one or more rings, incorporating one, two or three heteroatoms (chosen from nitrogen, oxygen or sulfur), which can optionally be substituted with one or more of the following substituents: hydroxy, cyano, alkyl, alkoxy, thioalkyl, halo, haloalkyl, trifluoromethyl, hydroxyalkyl, alkoxycarbonyl, nitro, amino, alkylamino, dialkylamino, aminocarbonyl, carbonylamino, aminosulfonyl and sulfonylamino, unless otherwise indicated. Examples of heterocyclic radicals include, but are not limited to, tetrahydrofuranyl, tetrahydropyranyl, piperidinyl, piperazinyl, morpholinyl, thiomorpholinyl, 1,1-dioxothiomorpholinyl, imidazolidinyl, pyrrolidinyl, pyrrolidin-2-one, pyrrolidin-2,3-dione, hydrogenated derivatives of heteroaryl as defined herein, and the like.

"Heterocycloalkyl" means the radical of the formula R'R", where R' is a heterocyclic radical as defined herein and R" is an alkylene radical as defined herein. Examples of heterocycloalkyl radicals include, but are not limited to, 1-piperazinylmethyl, 2-morpholinomethyl, and the like.

"Halogen" means the radical fluoro, chloro, bromo, and iodo.

"Haloalkyl" means the lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Hydroxyalkyl" means the lower alkyl radical as defined herein, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, and 2-(hydroxymethyl)-3-hydroxypropyl, and the like.

"Optional" or "optionally" means that the subsequently described event or circumstance may but need not occur, and that the description includes instances where the event or circumstance occurs and instances in which it does not. For example, the phrase "which group is optionally substituted with one to three halo atoms" or "optionally substituted aryl" means that the group referred to may or may not be substituted in order to fall within the scope of the invention, and that the description includes both substituted and unsubstituted moieties.

"Protected" in reference to a compound or a group means the derivative of compound or group in which a reactive site or sites are blocked with protective groups.

"Protective group" or "protecting group" means the group which selectively blocks one reactive site in a multifunctional compound such that a chemical reaction can be carried out selectively at another unprotective reactive site and which can be readily removed after the selective reaction is completed. Certain processes may rely upon the protective groups to block reactive oxygen or nitrogen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclic ethers, and methyl or alkyl ethers, and the like. Protective or blocking groups for carboxyl groups are similar to those described for hydroxyl groups, preferably tert-butyl, benzyl or methyl esters.

"Amino-protecting group" means the protecting group that refers to those organic groups intended to protect the nitrogen atom against undesirable reactions during synthetic procedures and includes, but is not limited to benzyl, benzyloxycarbonyl (carbobenzyloxy; CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by mild acids in the case of BOC, e.g., trifluoroacetic acid or hydrochloric acid in ethyl acetate; or by catalytic hydrogenation in the case of CBZ.

"Hydroxy-protecting group" means the protecting group that preserves a hydroxy group that otherwise would be modified by certain chemical reactions. Suitable hydroxy-protecting groups include ether-forming groups that can be removed easily after completion of all other reaction steps, such as the benzyl or the trityl group optionally substituted in their phenyl ring. Other suitable hydroxy-protecting groups include alkyl ether groups, the tetrahydropyranyl, silyl, trialkylsilyl ether groups and the allyl group.

"Deprotection" or "deprotecting" means the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Leaving group" means the group with the meaning conventionally associated with it in synthetic organic chemistry, i.e., an atom or group displaceable under alkylating conditions. Examples of leaving groups include, but are not limited to, halogen, alkane- or arenesulfonyloxy, such as methanesulfonyloxy, ethanesulfonyloxy, benzenesulfonyloxy, tosyloxy, thiomethyl, and thienyloxy, dihalophosphinoyloxy, tetrahalophosphoxy, optionally substituted benzyloxy, isopropyloxy, mesyloxy, tosyloxy, acyloxy, and the like.

"Inert organic solvent" or "inert solvent" means the solvent inert under the conditions of the reaction being described in conjunction therewith including, for example, benzene, toluene, acetonitrile, methyl sulfoxide (DMSO), tetrahydrofuran (THF), N,N-dimethylformamide (DMF), chloroform ($CHCl_3$), methylene chloride or dichloromethane ($CH_2Cl_2$), dichloroethane, diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

"Isomerism" means the compounds have identical molecular formulae but that differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes optical isomers. A carbon atom bonded to four nonidentical substituents is termed a "chiral center."

"Chiral isomer" means a compound with one chiral center. It has two enantiomeric forms of opposite chirality, and may exist as either an individual enantiomer or as a mixture of enantiomers. A mixture containing equal amounts of individual enantiomeric forms of opposite chirality is termed a "racemic mixture." A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture."

When one chiral center is present a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia* 1956, 12, 81; Cahn, *J. Chem. Educ.* 1964, 41, 116).

"Geometric isomers" means the diastereomers that owe their existence to hindered rotation about double bonds. These configurations are differentiated in their names by prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

The scope of the present invention comprises compounds that possess geometric isomerism, and that may or may not possess chiral or atropic isomerism in their substituents. Such compounds can therefore be produced as mixtures of stereoisomers, or as the individual isolated or purified stereoisomers. The individual enantiomers may be obtained by resolving a racemic or non-racemic mixture of an intermediate at some appropriate stage of the synthesis followed by completion of the synthesis in a way that preserves chirality, or by resolution of the compound of Formula (I) by conventional means. The individual enantiomers as well as racemic or non-racemic mixtures thereof are encompassed within the scope of the present invention, all of which are intended to be depicted by the structures of this specification unless otherwise specifically indicated.

A "pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable, as described herein, and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, benzenesulfonic acid, benzoic acid, 3-(4-hydroxybenzoyl)benzoic acid, camphorsulfonic acid, p-chlorobenzenesulfonic acid, cinnamic acid, citric acid, cyclopentanepropionic acid, ethanesulfonic acid, 1,2-ethanedisulfonic acid, fumaric acid, glucoheptonic acid, gluconic acid, glutamic acid, glycolic acid, hexanoic acid, heptanoic acid, hydroxynaphthoic acid, 2-hydroxyethanesulfonic acid, lactic acid, lauryl sulfuric acid, malic acid, maleic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-napthalenesulfonic acid, oxalic acid, 3-phenylpropionic acid, propionic acid, pyruvic acid, salicylic acid, stearic acid, succinic acid, tartaric acid, trimethylacetic acid, tertiary butylacetic acid, p-toluenesulfonic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methyl-glucamine, triethanolamine, tromethamine, and the like. Acceptable inorganic bases include aluminum hydroxide, calcium hydroxide, potassium hydroxide, sodium carbonate, and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt "Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate "Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

A "therapeutically effective amount" means an amount of a compound that, when administered to a subject for treating a disease state, is sufficient to effect such treatment for the disease state. The "therapeutically effective amount" will vary depending on the compound, and disease state being treated, the severity of the disease state treated, the age and relative health of the subject, the route and form of administration, the judgement of the attending medical or veterinary practitioner, and other factors.

"Prodrug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve easy of formulation, or provide site-specific delivery of the compound. Reference to a compound herein includes prodrug forms of a compound.

"Disease state" means any disease, condition, symptom, or indication.

"Modulator" means a molecule, such as a compound, that interacts with a target. The interactions include, but are not limited to, agonist, antagonist, and the like, as defined herein.

"Antagonist" means a molecule such as a compound, a drug, an enzyme inhibitor, or a hormone, that diminishes or prevents the action of another molecule or receptor site.

"Agonist" means a molecule, such as a compound, a drug, an enzyme activator or a hormone, that enhances the activity of another molecule or receptor site.

"Alpha$_1$-adrenergic receptors", "alpha$_{1A}$-adrenergic receptors" (previously known as "alpha$_{1C}$-adrenergic receptors"), "alpha$_{1B}$-adrenergic receptors", "alpha$_{1D}$-adrenergic receptors", or "alpha$_{1L}$-adrenergic receptors", used interchangeably with "alpha$_1$-adrenoceptors", "alpha$_{1A}$-adrenoceptors" (previously known as "alpha$_{1C}$-adrenoceptors"), "alpha$_{1B}$-adrenoceptors", "alpha$_{1D}$-adrenoceptors", and "alpha$_{1L}$-adrenoceptors", respectively, refers to a molecule conforming to the seven membrane-spanning G-protein receptors, which under physiologic conditions mediate various actions, for example, in the central and/or peripheral sympathetic nervous system through the binding of the catecholamines, epinephrine, and norepinephrine. Examples of physiological effects mediated by "alpha$_1$-adrenoceptors" include, but are not limited to, control of blood pressure, glycogenolysis, growth and hypertrophy of cardiac myocytes, contractility of the urinary tract, and the like.

The term "alpha$_1$-adrenergic receptor subtype" used interchangeably with "alpha$_1$-adrenoceptor subtype" refers to a distinct member of the class of alpha$_1$-adrenoceptors, selected from the alpha$_{1A}$- (previously known as alpha$_{1C}$-), alpha$_{1B}$-, alpha$_{1D}$- and alpha$_{1L}$-adrenoceptors. The subtypes have been distinguished based on differential binding profiles of ligands, such as the agonist oxymetazoline, and such as the antagonists, WB4101 and phentolamine. Furthermore, the genes encoding the alpha$_{1A}$- (previously known as alpha$_{1C}$-), alpha$_{1B}$- and alpha$_{1D}$-subtypes have been isolated and cloned. The existence of an additional subtype, the alpha$_{1L}$ adrenergic receptor subtype, has been proposed; however, the gene for the alpha$_{1L}$ adrenergic receptor subtype has not yet been cloned.

The term "specific alpha$_1$-adrenergic receptor" as used herein, refers to a distinct member of the group or class of adrenoceptors, which may be selected from the alpha$_{1A}$- (previously known as alpha$_{1C}$-), alpha$_{1B}$-, alpha$_{1D}$- and alpha$_{1L}$-adrenoceptors. Preferred species from which may be derived or isolated alpha$_1$-adrenergic receptor subtype polypeptides, genes encoding an alpha$_1$-adrenergic receptor subtype, and/or cells, tissues and organs that express one or more alpha$_1$-adrenergic receptor subtype, include human, bovine, rat, murine, porcine, bovine, and the like. A more preferred species is human.

"Alpha$_{1B}$-adrenergic receptors" means a specific alpha$_1$-adrenoceptor expressed in numerous tissues, most notably in the liver, heart and cerebral cortex. alpha$_{1B}$-adrenoceptors are also present in areas of the spinal cord which receive input from sympathetic neurons originating in the pontine micturition center, and are presumed to be involved in the regulation of bladder function.

The term "pharmacological effect" as used herein encompasses effects produced in the subject that achieve the intended purpose of a therapy. In one preferred embodiment, a pharmacological effect means that pain symptoms of the subject being treated are prevented, alleviated, or reduced. For example, a pharmacological effect would be one that results in the reduction of pain in a treated subject. In another preferred embodiment, a pharmacological effect means that disorders or symptoms of the urinary tract of the subject being treated are prevented, alleviated, or reduced. For example, a pharmacological effect would be one that results in the prevention or reduction of incontinence or pelvic hypersensitivity in a treated subject.

"Treating" or "treatment" of a disease state includes:

(1) preventing the disease state, i.e. causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state i.e., causing regression of the disease state or its clinical symptoms.

The term "subject" as used herein encompasses mammals and non-mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds and the like. The term does not denote a particular age or sex.

"Trauma" means any wound or injury. Trauma can produce, for example, acute and/or chronic pain, inflammatory pain, and neuropathic pain.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28th Edition, W.B. Saunders Company, Philadelphia, Pa.). The goal of treatment of pain is to reduce the degree or severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Hyperalgesia" means the abnormally increased pain sense, such as pain that results from an excessive sensitiveness or sensitivity.

"Hypalgesia" (or "hypoalgesia") means the decreased pain sense.

"Allodynia" means the pain that results from a non-noxious stimulus to the skin. Examples of allodynia include, but are not limited to cold allodynia, tactile allodynia and the like.

"Complex regional pain syndromes" means the pain that includes, but is not limited to, reflex sympathetic dystrophy, causalgia, sympathetically maintained pain, and the like.

"Causalgia" means the burning pain, often accompanied by trophic skin changes, due to injury of a peripheral nerve.

"Nociception" means pain sense. "Nociceptor" means a structure that mediates nociception. Nociception may be the result of a physical stimulus, such as, mechanical, electrical, thermal, or a chemical stimulus. Most nociceptors are in either the skin or the viscera walls.

"Analgesia" means the relief of pain without the loss of consciousness. An "analgesic" is an agent or drug useful for relieving pain, again, without the loss of consciousness.

"Disorders of the urinary tract" or "uropathy" used interchangeably with "symptoms of the urinary tract" means the pathologic changes in the urinary tract. Symptoms of the urinary tract include overactive bladder (also known as detrusor hyperactivity), outlet obstruction, outlet insufficiency, and pelvic hypersensitivity. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiopathic bladder hypersensitivity, and the like.

"Overactive bladder" or "Detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Outlet obstruction" includes, but is not limited to, benign prostatic hypertrophy (BPH), urethral stricture disease, tumors and the like. It is usually symptomatically manifested as obstructive (low flow rates, difficulty in initiating urination, and the like), and irritative (urinary urge and frequency, suprapubic pain, nocturia, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Nomenclature

The naming and numbering of the compounds of this invention is illustrated below.

In general, the nomenclature used in this application is based on AutoNom, a Beilstein Institute computerized system for the generation of IUPAC systematic nomenclature.

For example, a compound of Formula (I)

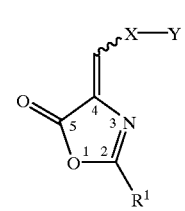

(I)

wherein $R^1$ is naphthyl, X is piperazinyl, and Y is —CO—$R^4$, wherein $R^4$ is furanyl, is named:
4-[4-(Furan-2-carbonyl)-piperazin-1-ylmethylene]-2-naphthalen-1-yl-4H-oxazol-5-one.

Similarly, a compound of Formula (I) wherein $R^1$ is benzofuranyl, X is piperazinyl, and Y is —$R^3$, wherein $R^3$ is benzimidazolyl, is named:
2-Benzofuran-4-yl-4-[4-(1H-benzoimidazol-2-yl)-piperazin-1-ylmethylene]-4H-oxazol-5-one.

Additionally, a compound of Formula (I) wherein $R^1$ is naphthyl, X is piperazinyl, and Y is —CO—NH—$R^5$, wherein $R^5$ is 3-fluorophenyl, is named:
4-(2-Naphthalen-1-yl-5-oxo-oxazol-4-ylidenemethyl)-piperazine-1-carboxylic acid (3-fluoro-phenyl)-amide.

Similarly, a compound of Formula (I) wherein $R^1$ is benzofuranyl, X is piperazinyl, and Y is —C(NH)—NH—$R^7$, wherein $R^7$ is pyridyl, is named:
4-(2-Benzofuran-7-yl-5-oxo-oxazol-4-ylidenemethyl)-N-pyridin-2-yl-piperazine-1-carboxamidine.

Preferred Compounds

Among the compounds of the present invention set forth in the Summary of the Invention, certain additional compounds are preferred. For example, preferred compounds of Formula (I), or individual isomers, racemic or non-racemic mixtures of isomers, or pharmaceutically acceptable salts or solvates thereof, include:
4-(2-Naphthalen-1-yl-5-oxo-oxazol-4-ylidenemethyl)-piperazine-1-carboxylic acid phenylamide (208, Example 13);
4-(2-Naphthalen-1-yl-5-oxo-oxazol-4-ylidenemethyl)-N-pyridin-2-yl-piperazine-1-carboxamidine (276, Example 16);
4-(2-Naphthalen-1-yl-5-oxo-oxazol-4-ylidenemethyl)-N-phenyl-piperazine-1-carboxamidine (334, Example 19);

4-[4-(1H-Benzoimidazol-2-yl)-piperazin-1-ylmethylene]-2-naphthalen-1-yl-4H-oxazol-5-one (416, Example 24);

4-[2-(4-Fluoro-naphthalen-1-yl)-5-oxo-oxazol-4-ylidenemethyl]-piperazine-1-carboxylic acid phenylamide (212, Example 13);

4-[2-(4-Fluoro-naphthalen-1-yl)-5-oxo-oxazol-4-ylidenemethyl]-N-pyridin-2-yl-piperazine-1-carboxamidine (278, Example 16);

4-[2-(4-Fluoro-naphthalen-1-yl)-5-oxo-oxazol-4-ylidenemethyl]-N-phenyl-piperazine-1-carboxamidine (336, Example 19);

4-[4-(1H-Benzoimidazol-2-yl)-piperazin-1-ylmethylene]-2-(4-fluoro-naphthalen-1-yl)-4H-oxazol-5-one (418, Example 24);

4-[4-(4,5-Dihydro-1H-imidazol-2-yl)-piperazin-1-ylmethylene]-2-(4-fluoro-naphthalen-1-yl)-4H-oxazol-5-one (500, Example 30);

4-[2-(7-Fluoro-benzofuran-4-yl)-5-oxo-oxazol-4-ylidenemethyl]-piperazine-1-carboxylic acid phenylamide (248, Example 14);

4-[2-(7-Fluoro-benzofuran-4-yl)-5-oxo-oxazol-4-ylidenemethyl]-N-pyridin-2-yl-piperazine-1-carboxamidine (as hydrochloride 324, Example 17);

4-[2-(7-Fluoro-benzofuran-4-yl)-5-oxo-oxazol-4-ylidenemethyl]-N-phenyl-piperazine-1-carboxamidine (as hydrochloride 382, Example 20);

4-[4-(1H-Benzoimidazol-2-yl)-piperazin-1-ylmethylene]-2-(7-fluoro-benzofuran-4-yl)-4H-oxazol-5-one (464, Example 25);

4-(2-Benzofuran-4-yl-5-oxo-oxazol-4-ylidenemethyl)-piperazine-1-carboxylic acid phenylamide (250, Example 14);

4-(2-Benzofuran-4-yl-5-oxo-oxazol-4-ylidenemethyl)-N-pyridin-2-yl-piperazine-1-carboxamidine (as hydrochloride 326, Example 17);

4-(2-Benzofuran-4-yl-5-oxo-oxazol-4-ylidenemethyl)-N-phenyl-piperazine-1-carboxamidine (as hydrochloride 338, Example 20);

2-Benzofuran-4-yl-4-[4-(1H-benzoimidazol-2-yl)-piperazin-1-ylmethylene]-4H-oxazol-5-one (as hydrochloride 458, Example 25);

4-[2-(2,3-Dihydro-benzofuran-4-yl)-5-oxo-oxazol-4-ylidenemethyl]-piperazine-1-carboxylic acid phenylamide (254, Example 14);

4-[2-(2,3-Dihydro-benzofuran-4-yl)-5-oxo-oxazol-4-ylidenemethyl]-N-pyridin-2-yl-piperazine-1-carboxamidine (as hydrochloride 330, Example 17);

4-[2-(2,3-Dihydro-benzofuran-4-yl)-5-oxo-oxazol-4-ylidenemethyl]-N-phenyl-piperazine-1-carboxamidine (as hydrochloride 386, Example 20);

4-(2-Benzofuran-7-yl-5-oxo-oxazol-4-ylidenemethyl)-piperazine-1-carboxylic acid phenylamide (252, Example 14);

1 5 4-(2-Benzofuran-7-yl-5-oxo-oxazol-4-ylidenemethyl)-N-pyridin-2-yl-piperazine-1-carboxamidine (as hydrochloride 318, Example 17);

4-(2-Benzofuran-7-yl-5-oxo-oxazol-4-ylidenemethyl)-N-phenyl-piperazine-1-carboxamidine (as hydrochloride 332, Example 20);

2-Benzofuran-7-yl-4-[4-(4,5-dihydro-1H-imidazol-2-yl)-piperazin-1-ylmethylene]-4H-oxazol-5-one (as hydrochloride 498, Example 30);

4-[2-(2,3-Dihydro-benzofuran-7-yl)-5-oxo-oxazol-4-ylidenemethyl]-piperazine-1-carboxylic acid phenylamide (242, Example 14);

4-[2-(2,3-Dihydro-benzo[1,4]dioxin-5-yl)-5-oxo-oxazol-4-ylidenemethyl]-N-pyridin-2-yl-piperazine-1-carboxamidine (256, Example 14);

4-[4-(1H-Benzoimidazol-2-yl)-piperazin-1-ylmethylene]-2-(2,3-dihydro-benzo[1,4]dioxin-5-yl)-4H-oxazol-5-one (466, Example 25); and 2-(2,3-Dihydro-benzo[1,4]dioxin-5-yl)-4-[4-(4,5-dihydro-1H-imidazol-2-yl)-piperazin-1-ylmethylene]-4H-oxazol-5-one (504, Example 30).

More preferred compounds of Formula (I), or individual isomers, racemic or non-racemic mixtures of isomers, or pharmaceutically acceptable salts or solvates thereof, include:

4-(2-Naphthalen-1-yl-5-oxo-oxazol-4-ylidenemethyl)-piperazine-1-carboxylic acid phenylamide (208, Example 13);

4-(2-Naphthalen-1-yl-5-oxo-oxazol-4-ylidenemethyl)-N-pyridin-2-yl-piperazine-1-carboxamidine (276, Example 16);

4-(2-Naphthalen-1-yl-5-oxo-oxazol-4-ylidenemethyl)-N-phenyl-piperazine-1-carboxamidine (334, Example 19);

4-[4-(1H-Benzoimidazol-2-yl)-piperazin-1-ylmethylene]-2-naphthalen-1-yl-4H-oxazol-5-one (416, Example 24);

4-[2-(4-Fluoro-naphthalen-1-yl)-5-oxo-oxazol-4-ylidenemethyl]-piperazine-1-carboxylic acid phenylamide (212, Example 13);

4-[2-(4-Fluoro-naphthalen-1-yl)-5-oxo-oxazol-4-ylidenemethyl]-N-pyridin-2-yl-piperazine-1-carboxamidine (278, Example 16);

4-[2-(4-Fluoro-naphthalen-1-yl)-5-oxo-oxazol-4-ylidenemethyl]-N-phenyl-piperazine-1-carboxamidine (336, Example 19);

4-[4-(1H-Benzoimidazol-2-yl)-piperazin-1-ylmethylene]-2-(4-fluoro-naphthalen-1-yl)-4H-oxazol-5-one (418, Example 24);

4-[2-(7-Fluoro-benzofuran-4-yl)-5-oxo-oxazol-4-ylidenemethyl]-piperazine-1-carboxylic acid phenylamide (248, Example 14);

4-[2-(7-Fluoro-benzofuran-4-yl)-5-oxo-oxazol-4-ylidenemethyl]-N-pyridin-2-yl-piperazine-1-carboxamidine (as hydrochloride 324, Example 17);

4-[2-(7-Fluoro-benzofuran-4-yl)-5-oxo-oxazol-4-ylidenemethyl]-N-phenyl-piperazine-1-carboxamidine (as hydrochloride 382, Example 20);

4-[4-(1H-Benzoimidazol-2-yl)-piperazin-1-ylmethylene]-2-(7-fluoro-benzofuran-4-yl)-4H-oxazol-5-one (464, Example 25);

4-(2-Benzofuran-4-yl-5-oxo-oxazol-4-ylidenemethyl)-piperazine-1-carboxylic acid phenylamide (250, Example 14);

4-(2-Benzofuran-4-yl-5-oxo-oxazol-4-ylidenemethyl)-N-pyridin-2-yl-piperazine-1-carboxamidine (as hydrochloride 326, Example 17);

4-(2-Benzofuran-4-yl-5-oxo-oxazol-4-ylidenemethyl)-N-phenyl-piperazine-1-carboxamidine (as hydrochloride 338, Example 20); and 2-Benzofuran-4-yl-4-[4-(1H-benzoimidazol-2-yl)-piperazin-1-ylmethylene]-4H-oxazol-5-one (as hydrochloride 458, Example 25).

Even more preferred compounds of Formula (I), wherein the compound is present as an individual isomer, a racemic or non-racemic mixture of isomers, or a pharmaceutically acceptable salt or solvate thereof, include:

4-(2-Naphthalen-1-yl-5-oxo-oxazol-4-ylidenemethyl)-N-pyridin-2-yl-piperazine-1-carboxamidine (276, Example 16);

4-(2-Naphthalen-1-yl-5-oxo-oxazol-4-ylidenemethyl)-N-phenyl-piperazine-1-carboxamidine (334, Example 19);

4-[2-(4-Fluoro-naphthalen-1-yl)-5-oxo-oxazol-4-ylidenemethyl]-N-pyridin-2-yl-piperazine-1-carboxamidine (278, Example 16);

4-[2-(4-Fluoro-naphthalen-1-yl)-5-oxo-oxazol-4-ylidenemethyl]-N-phenyl-piperazine-1-carboxamidine (336, Example 19);

4-(2-Benzofuran-4-yl-5-oxo-oxazol-4-ylidenemethyl)-N-pyridin-2-yl-piperazine-1-carboxamidine (as hydrochloride 326, Example 17); and 4-(2-Benzofuran-4-yl-5-oxo-oxazol-4-ylidenemethyl)-N-phenyl-piperazine-1-carboxamidine (as hydrochloride 338, Example 20).

Another preferred group includes the pharmaceutically acceptable salts or solvates of the compounds of the present invention wherein the pharmaceutically acceptable salts are formed from acetic acid, hydrochloric acid, sulphuric acid, methanesulfonic acid, maleic acid, phosphoric acid, tartaric acid, citric acid, sodium, potassium, calcium, zinc, and magnesium.

General Synthetic Scheme

Compounds of this invention can be made by the methods depicted in the reaction schemes shown below.

The starting materials and reagents used in preparing these compounds are either available from commercial suppliers, such as Aldrich Chemical Co., or are prepared by methods known to those skilled in the art following procedures set forth in references such as Fieser and *Fieser's Reagents for Organic Synthesis*, Wiley & Sons, New York, 1991, Volumes 1–15; *Rodd's Chemistry of Carbon Compounds*, Elsevier Science Publishers, 1989, Volumes 1–5 and Supplementals; and *Organic Reactions*, Wiley & Sons, New York, 1991, Volumes 1–40. These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to, filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C.

Compounds of Formula (I) are prepared using general methods described in the literature. Particularly, intermediate compounds of structure 3 in which $R^1$ is as described herein can be prepared as described in, for example, Cornforth, J. W., *The Chemistry of Penicillin*, Princeton University Press, Princeton N.J., 1949, Chapter 21; Bland J. M. et al., *Journal of Organic Chemistry*, 1984, 49, 1634–1636 and Kocevar M. et al., *Liebigs Ann. Chem.*, 1990, 5, 501–503.

Generally, as set forth in reaction Scheme 1, a carboxylic acid 1 is first converted to the corresponding acid chloride, by treatment with, for example, oxalyl chloride, followed by conversion to the corresponding glycine amide 2. The resulting acid-amide 2 can be cyclized using, for example, triethyl orthoformate and acetic anhydride at 80° C. to yield the $R^1$-substituted 4-ethoxymethylene-5-oxazolones 3.

SCHEME 1

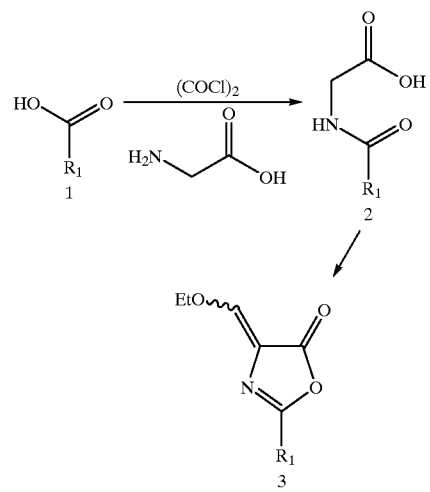

In general, the compounds of the present invention can be prepared by first alkylating an optionally substituted amine, such as 4A, 4B or 4C (wherein Y is as described above; see reaction Scheme 2) with an $R^1$-substituted 4-ethoxymethylene-5-oxazolone 3 (prepared as set forth in reaction Scheme 1), to yield compounds 5A, 5B or 5C, respectively.

SCHEME 2A

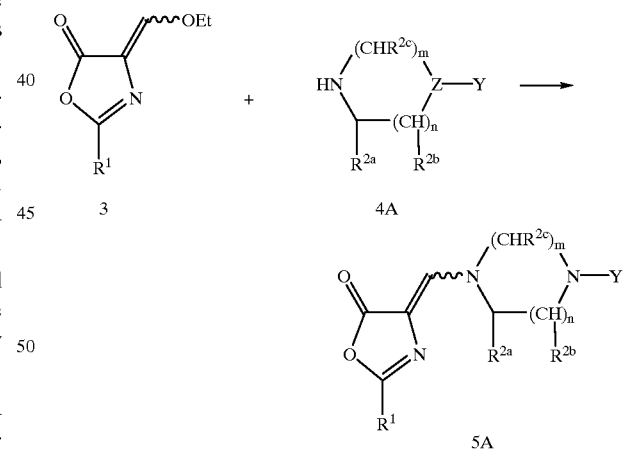

SCHEME 2B

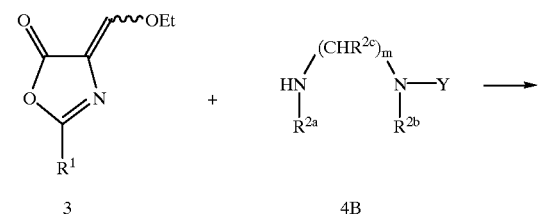

21

-continued

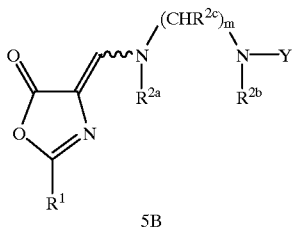

5B

SCHEME 2C

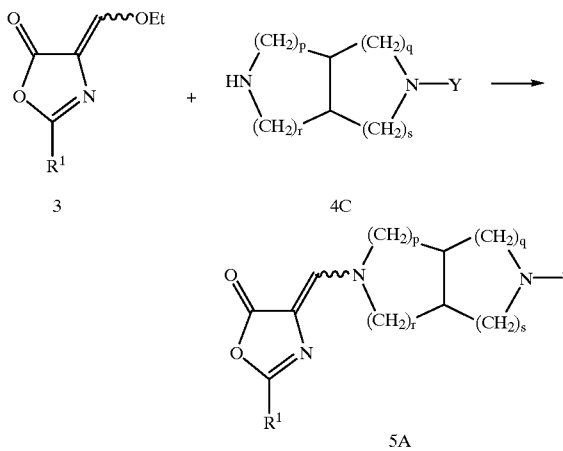

An alternative method of preparing the compounds of this invention is alkylation of a suitably mono-protected diamine, such as 6A, 6B or 6C, with an $R^1$-substituted 4-ethoxymethylene-5-oxazolone 3 (prepared as set forth in reaction Scheme 1), to yield compounds 7A, 7B or 7C (wherein P denotes a suitable protecting group as described herein, such as benzyl, benzyloxycarbonyl (carbobenzyloxy; CBZ), p-methoxybenzyloxycarbonyl, p-nitrobenzyloxycarbonyl, tert-butoxycarbonyl (BOC), trifluoroacetyl, preferably BOC or CBZ), and then deprotecting (see reaction Scheme 3), to yield compounds 8A, 8B or 8C. Compounds 5A, 5B and 5C can be then prepared by adding an appropriately activated Y, wherein Y is as defined herein, onto compounds 8A, 8B or 8C, respectively.

The alkylation of compounds 6A, 6B or 6C can be carried out neat at about 0° to about 250° C., typically at about 10° to about 150° C. and preferably at about 20° to about 100° C., requiring about 1 to about 24 hours (for further details see, e.g., Example 2, infra). Alternatively, the reaction can be carried out in a suitable inert organic solvent (e.g., acetonitrile, methyl sulfoxide (DMSO), N,N-dimethylformamide (DMF), N-methylpyrrolidione (NMP), benzene, toluene, any appropriate mixture of suitable solvents, etc., preferably acetonitrile or DMSO) with a suitable base present (e.g., sodium carbonate, potassium carbonate, cesium carbonate, 2,4,6-trimethylpyridine, triethylamine, N,N-diisopropylethylamine, etc., preferably sodium carbonate, triethylamine, or N,N-diisopropylethylamine) at 0° to about 250° C., typically at about 10° to about 150° C. and preferably at about 20° to about 100° C., and preferably at reflux, requiring about 2 to about 72 hours (for further details see, e.g., Example 3, infra).

Deprotection of compounds 7A, 7B or 7C, in which a nitrogen protective group is present, can be effected by any means which remove the protective group and give the desired product 8A, 8B or 8C. As described herein, a detailed description of the techniques applicable to protective groups and their removal can be found in T. W. Greene, *Protective Groups in Organic Synthesis,* Wiley and Sons, New York, 1991. For example, a convenient method of deprotection when the protective group is N-tert-butoxycarbonyl can be carried out with trifluoroacetic acid or hydrochloric acid in a suitable inert organic (e.g., ethyl acetate, dichloromethane, tetrahydrofuran (THF), hexamethylphosphoramide (HMPA), or any appropriate mixture of suitable solvents, etc., preferably THF or ethyl acetate) at 0° to about 250° C., typically at about 10° to about 150° C. and preferably at about 20° to about 100° C., and requires about 8 to about 24 hours (for further details see, e.g., Example 3, infra). Deprotection, when the protective group is benzyl or CBZ, can be carried out by catalytic hydrogenation. The hydrogenation is carried out with a suitable catalyst (e.g., 10% palladium on carbon (10% Pd/C), palladium hydroxide, palladium acetate, etc. preferably 10% Pd/C) in the presence of ammonium formate and in an appropriate solvent, typically an alcohol (e.g., ethanol, methanol, isopropanol, any appropriate mixture of alcohols, etc.), preferably methanol, at about 0° to about 250° C., typically at about 10° to about 150° C. and preferably at about 20° to about 100° C. and preferably at reflux. Alternatively, the benzyl group can be removed by treating the protected compound with the catalyst under a hydrogen atmosphere at 0 to 50 psi, typically at 10 to 20 psi and preferably at approximately 15 psi, at about 0° to about 250° C., typically at about 10° to about 150° C., and preferably at about 20° to about 100° C.

Compounds 5A, 5B and 5C can then prepared by adding an appropriately activated Y, wherein Y is as defined herein, onto compounds 8A, 8B or 8C, respectively. The substitution reaction is carried out at about 0° to about 250° C., typically at about 10° to about 150° C. and preferably at about 20° to about 100° C., requiring about 1 to about 24 hours. The reaction can be carried out in a suitable inert organic solvent (e.g., acetonitrile, methyl sulfoxide (DMSO), N,N-dimethylformamide (DMF), N-methylpyrrolidione (NMP), benzene, toluene, any appropriate mixture of suitable solvents, etc., preferably acetonitrile or DMSO) with a suitable base optionally present, e.g., sodium carbonate, potassium carbonate, cesium carbonate, 2,4,6-trimethylpyridine, triethylamine, N,N-diisopropylethylamine (Hünig's base), etc., preferably sodium carbonate, triethylamine, N,N-diisopropylethylamine (Hünig's base); for further details see, e.g., Examples 4, 5, 6 and 7, infra at about 0° to about 250° C., typically at about 10° to about 150° C. and preferably at about 20° to about 100° C. and more preferably at reflux, requiring 2 to 72 hours, see, e.g., Example 5, infra.

SCHEME 3A

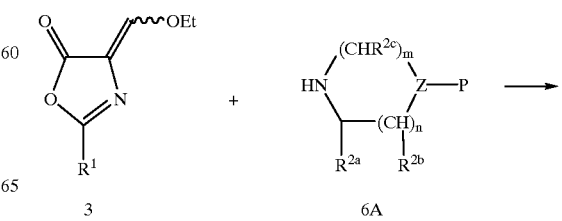

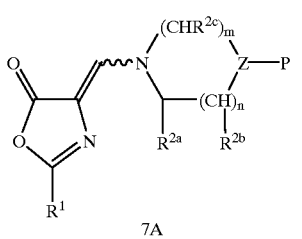

7A

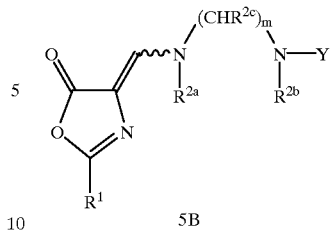

5B

SCHEME 3C

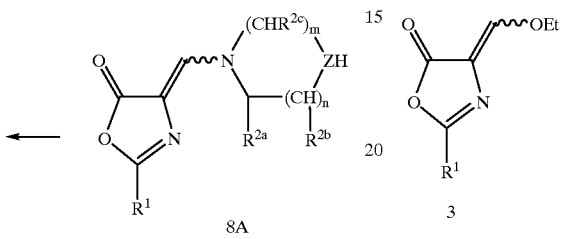

8A

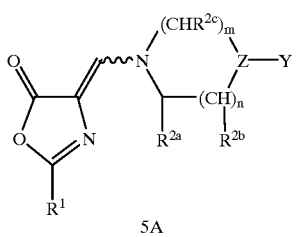

5A

SCHEME 3B

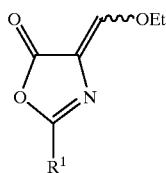

3

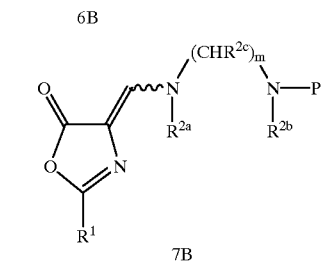

7B

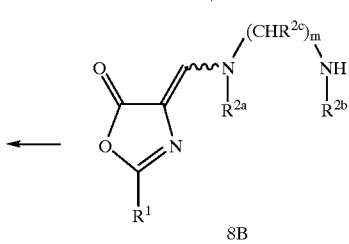

8B

Administration and Pharmaceutical Compositions

The invention provides pharmaceutical compositions comprising a compound of the present invention or a pharmaceutically acceptable salt, solvate or derivative thereof together with one or more pharmaceutically acceptable carriers, and optionally other therapeutic and/or prophylactic ingredients.

In general, the compounds of this invention will be administered in a therapeutically effective amount by any of the accepted modes of administration for agents that serve similar utilities. Suitable dosage ranges are about 1 mg to about 500 mg daily, preferably about 1 mg to about 100 mg daily, and more preferably about 1 mg to about 30 mg daily, depending upon numerous factors such as the severity of the disease state to be treated, the age and relative health of the subject, the potency of the compound used, the route and form of administration, the indication towards which the administration is directed, and the preferences and experience of the medical or veterinary practitioner involved. One of ordinary skill in the art of treating such a disease state will be able, without undue experimentation and in reliance upon personal knowledge and the disclosure of this application, to ascertain a therapeutically effective amount of the compounds of this invention for use in treating a given disease state.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous, and intravenous) administration or in a form suitable for administration by inhalation or insufflation. The preferred manner of administration is oral using a convenient daily dosage regimen which can be adjusted according to the degree of affliction.

The compounds of the invention, together with a conventional adjuvant, carrier, or diluent, may be placed into the form of pharmaceutical compositions and unit dosages. The pharmaceutical compositions and unit dosage forms may comprise conventional ingredients in conventional proportions, with or without additional active compounds or principles, and the unit dosage forms may contain any suitable effective amount of the active ingredient commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about 0.01 to 100 milligrams, preferably 1 to 50 milligrams, more preferably 1 to 10 milligrams, per tablet, are accordingly suitable representative unit dosage forms.

The compounds of the present invention may be formulated in a wide variety of oral administration dosage forms. The pharmaceutical compositions and dosage forms may comprise the compounds of the invention or its pharmaceutically acceptable salt or solvate as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the finely divided active component. In tablets, the active component is mixed with the carrier having the necessary binding capacity in suitable proportions and compacted in the shape and size desired. The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations such as emulsions, syrups, elixirs, aqueous solutions, aqueous suspensions, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into conveniently sized molds, allowed to cool, and to solidify.

The compounds of the present invention may be formulated for vaginal administration. Pessaries, tampons, creams, gels, pastes, foams or sprays, may contain agents in addition to the active ingredient, such carriers, known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract including intranasal administration. The compound will generally have a small particle size for example of the order of about 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively, the active ingredients may be provided in a form of a dry powder, for example a powder mix of the compound in a suitable powder base such as lactose, starch, starch derivatives such as hydroxypropylmethylcellulose and polyvinylpyrrolidine (PVP). The powder carrier will form a gel in the nasal cavity. The powder composition may be presented in unit dose form for example in capsules or cartridges of, e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Example 49.

Pharmacology and Utility

Alpha$_1$-adrenoceptors mediate the contractile state of smooth muscle tissue and are present in the human prostate, bladder neck and urethra. Sympathetic activity produces contraction of vascular smooth muscle which leads to elevated blood pressures. Alpha$_1$-adrenoceptor stimulation also produces glycogenolysis, growth and hypertrophy of cardiac myocytes and contraction of urethral and bladder neck smooth muscle, leading to increased resistance in urinary outflow. Thus, alpha$_1$-adrenoceptor antagonists may be useful in preventing hypertension and treating disorders or symptoms related to uropathies, such as obstruction due to benign prostatic hyperplasia (BPH). (See U.S. Pat. No. 5,859,014; Lepor, H., *The Prostate Supplement*, 1990, 3:75–84 and International Publication No. WO 95/25726.)

Some drugs effective in the treatment of benign prostatic hyperplasia block alpha$_{1A}$-adrenergic mediated contractions of the prostate. Alpha$_{1A}$-adrenoceptors may mediate smooth muscle hyperplasia in the prostate, therefore a selective alpha$_{1A}$-adrenoceptor antagonist may have utility not only in mitigating the excessive prostatic constriction, but also in preventing progression of tissue hyperplasia.

Experimental evidence supports a therapeutic role for alpha$_1$-adrenoceptor antagonists in treating prostatic hyperplasia. (See for example, Lepor, H., *The Prostate Supplement*, 1990, 3, 75–84.) Obstruction of the urinary tract can occur as a result of prostatic hyperplasia and excessive prostatic constriction of the urethra. This in turn leads to diminished urinary flow rates and an increased urgency and frequency of urination.

In a preferred embodiment, the compounds of this invention are useful for treating disease states which can be ameliorated by modulation, preferably by blockade of alpha$_1$-adrenoceptors, such as reduction or alleviation of urinary tract disorders, for example, pelvic hypersensitivity (including interstitial cystitis, prostatitis, pelvic pain syndrome, infectious cystitis, prostatodynia, and the like), overactive bladder, urinary frequency, nocturia, urinary urgency, detrusor hyperreflexia, outlet obstruction, prostatitis, urge incontinence, urethritis, idiophatic bladder hypersensitivity, and the like. Compounds of this invention may also be useful for treating male erectile dysfunction and female sexual dysfunction.

In a more preferred embodiment, the compounds of the invention are useful for treating disease states which can be ameliorated by blockade of alpha$_1$-adrenoceptors. Alpha$_{1B}$-adrenoceptors are present in the liver, heart and cerebral cortex and are believed to be involved in mediating vascular contractile and blood pressure responses. Additionally, alpha$_{1B}$-adrenoceptors are also present in areas of the spinal cord which receive input from sympathetic neurons originating in the pontine micturition center and are presumed to be involved in the regulation of bladder function. Selective blockade of the alpha$_{1B}$-adrenoceptor may lead to the symptomatic treatment of pelvic hypersensitivity including interstitial cystitis, prostatitis, pelvic pain syndrome, infectious cystitis, prostatodynia, and the like, and symptoms associated with overactive bladder.

Several clinical observations suggest a therapeutic role for alpha1B-adrenoceptor antagonists in the prevention of disease states of the urinary tract, such as pelvic hypersensitivity (including interstitial cystitis, prostatitis, pelvic pain syndrome, infectious cystitis, prostatodynia, and the like), urethritis, overactive bladder (manifested as urge incontinence), detrusor hyperreflexia, outlet obstruction (resulting from benign prostatic hypertrophy and prostatitis), and other conditions of idiophatic bladder hypersensitivity.

Additionally, alpha$_{1B}$-adrenoceptor antagonists are useful as analgesic/antihyperalgesic therapies for treating pain, including symptoms of acute pain, inflammatory pain, neuropathic pain (including thermal and mechanical hyperalgesia as well as thermal and mechanical allodynia), complex regional pain syndromes (including reflex sympathetic dystrophy, causalgia and sympathetically maintained pain). (See, commonly owned U.S. patent application Ser. No. 60/124,721 by Ford et al. entitled "A Method For Screening Compounds For Alpha$_{1B}$Adrenergic Receptor Antagonist and Analgesic Activity," filed on Mar. 17, 1999, the disclosure of which is hereby incorporated by reference in its entirety.)

Assays

The pharmacology of the compounds of this invention was determined by art-recognized procedures. In vitro techniques for determining the affinities of test compounds in radioligand binding and functional assays are described in Example 45.

The effect of the compounds of this invention on blood pressure can be evaluated by any method known in the art. Examples of such methods are as follows.

Rat In Vivo, Blood Pressure Assay

An in vivo assay for measuring the blood pressure lowering effects of test compounds in normotensive rats is described in Example 46.

Normotensive rats (0.25 to 0.45 kg) are fasted for 18 hours and anesthetized with ether. The right femoral vein is isolated and cannulated with a fluid-filled polyethylene cannulae for bolus administration of test substances. The right femoral artery is isolated and cannulated with a fluid-filled polyethylene cannula connected to an external pressure transducer for monitoring mean arterial blood pressure (MAP).

Following cannulation, rats are pretreated (intravenous route) with an angiotensin receptor antagonist, a β-adrenergic receptor antagonist and an alpha$_2$adrenergic receptor antagonist as described in Blue et al. (*Br. J. Pharmacol.* 120:107P).

The rats are placed in restrainers and allowed to recover from anesthesia. Following a 30-minute period for stabilization, test compound or vehicle are administered, i.v., and blood pressure is monitored continuously for at least 4 hours post-administration.

Rat In Vivo, Tilt-Response Assay

The following describes an in vivo assay in normotensive rats for measuring the propensity of a test compound to inhibit the reflex maintenance of basal blood pressure levels in response to vertical tilt.

Normotensive rats (0.25 to 0.45 kg) are fasted for 18 hours and anesthetized with ether. The right femoral vein is isolated and cannulated with a fluid-filled polyethylene cannulae for bolus administration of test substances. The right femoral artery is isolated and cannulated with a fluid-filled polyethylene cannula connected to an external pressure transducer for monitoring mean arterial blood pressure (MAP).

The rats are restrained in a supine position and allowed to recover from anesthesia. Following a 30-minute period for stabilization, test compound or vehicle are administered, i.v., and blood pressure is monitored continuously while the rats are tilted vertically at 30 to 60 degrees from supine at 15, 30 and 45 minutes post-administration.

Dog In Vivo, Blood and Intraurethral Pressure Assay

The following describes an in vivo assay for measuring the relative effect of a test compound on hypogastric nerve stimulation-induced increases in intraurethral pressure and phenylephrine-induced increases in diastolic blood pressure in anesthetized dog.

Mongrel dogs (10 to 20 kg) are fasted for 12 to 18 hours and anesthetized with phenobarbital sodium (35 mg/kg, i.v.). An endotracheal tube is inserted and thereafter the lungs are mechanically ventilated with room air. The right femoral vein is isolated and cannulated with two polyethylene cannulae, one for the administration of a continuous infusion of phenobarbital sodium (5 to 10 mg/kg/hr) and the other for bolus administration of test substances. The right femoral artery is isolated and cannulated to the abdominal aorta with a fluid filled polyethylene cannula connected to an external pressure transducer for monitoring diastolic aortic pressure (DAP). The bladder is exposed via a ventral midline abdominal incision and emptied of urine through a 22-gauge needle. The bladder is cannulated through a stab incision with a water-filled balloon catheter connected to an external pressure transducer for monitoring prostatic intraurethral pressure (IUP). The right hypogastric nerve (HGN) is carefully isolated and attached to a Dastre's electrode for nerve stimulation.

The preparation is allowed to stabilize for a least 30 minutes and must have a stable basal IUP for not less than 15 minutes prior to commencement of the assay protocol. The HGN is stimulated (20–50 V, 10 Hz, 10 msec pulse train for 10 sec) to induce a measurable increase in IUP and then phenylephrine (PE) is administered by bolus injection (0.5 to 0.6 µg/kg, i. v.) to induce a measurable increase in DAP. The HGN stimulation and PE bolus injection are repeated every 5 minutes until three consecutive reproducible increases in IUP and DAP are achieved. Vehicle (0.1 to 0.3 mL/kg) is administered and 20 minutes later the HGN stimulation and PE bolus injection are repeated. Test compound is then administered and 20 minutes later the HGN stimulation and PE bolus injection are repeated. Test compound is administered approximately every 20 minutes, increasing the dose until maximal or near maximal inhibition of the increases in IUP and DAP is attained.

The analgesic activity of the compounds of this invention can be evaluated by any method known in the art. Examples of such methods are as follows.

Tail Flick Model

The tail-flick test (D'Amour et al. (1941) *J. Pharmacol. Exp. and Ther.* 72:74–79) is a model of acute pain. A towel-wrapped rat is placed on a test stage such that a focused light source beams on the dorsal surface of the rat's tail. A photosensor is present on the test stage located opposite the light source and below the rat's tail. To begin the test the rat's tail blocks the light, thus preventing the light reaching the photosensor. Latency measurement begins with the activation of the light source. When a rat moves or flicks its tail the photosensor detects the light source and stops the measurement. The test measures the period of time (duration) that the rat's tail remains immobile (latent). Rats are tested pre-dose and then tested at various times post-dose. The light source is set to an intensity that produced a tail response latency of about 3 seconds when applied to the tails of pre-dose rats.

Rat Tail Immersion Model

The rat tail immersion assay is also a model of acute pain. A rat is loosely held in hand while covered with a small folded thin cotton towel with its tail exposed. The tip of the tail is dipped into a, e.g., 52° C. water bath to a depth of two inches. The rat responds by either wiggling of the tail or withdrawal of the tail from the water; either response is scored as the behavioral end-point. A rat is tested for a pre-dose tail response latency (TRL) score. It is then dosed with a selected agent and, following dosing, retested for tail response latency at various times post-dosing.

Carrageenan-induced Paw Hyperalgesia Model

The carrageenan paw hyperalgesia test is a model of inflammatory pain. A subcutaneous injection of carrageenan is made into the left hindpaws of rats. The mammals are dosed with a selected agent before, e.g., 30 minutes, the carrageenan injection or after, e.g., two hours, the carrageenan injection. Paw pressure sensitivity for each animal is tested with an analgesymeter three hours after the carrageenan injection. See, Randall et al., *Arch. Int. Pharmacodyn.*, 1957, 111:409–419.

The effects of selected agents on carrageenan-induced paw edema can also be examined. This test (see, Vinegar et al., *J. Phamacol. Exp. Ther.*, 1969, 166:96–103) allows an assessment of the ability of a compound to reverse or prevent the formation of edema evoked by paw carrageenan injection. The paw edema test is carried out using a plethysmometer for paw measurements. After administration of a drug, a carrageenan solution is injected subcutaneously into the lateral foot pad on the plantar surface of the left hind paw. At three hours post-carrageenan treatment, the volume of the treated paw (left) and the un-treated paw (right) is measured using a plethysmometer.

Formalin Behavioral Response Model

The formalin test is a model of acute, persistent pain. Response to formalin treatment is biphasic (Dubuisson et al., *Pain*, 1977, 4:161–174). The Phase 1 response is indicative of a pure nociceptive response to the irritant. Phase 2, typically beginning 20 to 60 minutes following injection of formalin, is thought to reflect increased sensitization of the spinal cord.

Von Frey Filament Test

The effect of $alpha_{1B}$-adrenergic receptor antagonists on mechanical allodynia can be determined by the von Frey filament test in rats with a tight ligation of the L-5 spinal nerve: a model of painful peripheral neuropathy. The surgical procedure is performed as described by Kim et al., *Pain*, 1992, 50:355–363. A calibrated series of von Frey filaments are used to assess mechanical allodynia (Chaplan et al., *J. Neurosci. Methods*, 1994, 53:55–63). Filaments of increasing stiffness are applied perpendicular to the midplantar surface in the sciatic nerve distribution of the left hindpaw. The filaments are slowly depressed until bending occurred and are then held for 4–6 seconds. The filament application order and number of trials were determined by the up-down method of Dixon (Chaplan et al., supra). Flinching and licking of the paw and paw withdrawal on the ligated side are considered positive responses.

Chronic Constriction Injury

Heat and cold allodynia responses can be evaluated as described below in rats having a chronic constriction injury (CCI). A unilateral mononeuropathy is produced in rats using the chronic constriction injury model described in Bennett et al., *Pain*, 1988, 33:87–107.

CCI is produced in anesthetized rats as follows. The lateral aspect of each rat's hind limb is shaved and scrubbed with Nolvasan. Using aseptic techniques, an incision is made on the lateral aspect of the hind limb at the mid-thigh level. The biceps femoris is bluntly dissected to expose the sciatic nerve. On the right hind limb of each rat, four loosely tied ligatures (for example, Chromic gut 4.0; Ethicon, Johnson and Johnson, Somerville, N.J.) are made around the sciatic nerve approximately 1–2 mm apart. On the left side of each rat, an identical dissection is performed except that the sciatic nerve is not ligated (sham). The muscle is closed with a continuous suture pattern with, e.g., 4-0 Vicryl (Johnson and Johnson, Somerville, N.J.) and the overlying skin is closed with wound clips. The rats are ear-tagged for identification purposes and returned to animal housing.

Radiant Heat Model

An in vivo assay for measuring the pain response to radiant heat in neuropathic rats is described in Example 47. Generally, CCI rats are tested for thermal hyperalgesia at least 10 days post-op. The test apparatus consists of an elevated heated (80–82° F.) glass platform. Eight rats at a time, representing all testing groups, are confined individually in inverted plastic cages on the glass floor of the platform at least 15 minutes before testing. A radiant heat source placed underneath the glass is aimed at the plantar hind paw of each rat. The application of heat is continued until the paw is withdrawn (withdrawal latency) or the time elapsed is 20 seconds. This trial is also applied to the sham operated leg. Two to four trials are conducted on each paw, alternately, with at least 5 minutes interval between trials. The average of these values represents the withdrawal latency.

Cold Allodynia Model

The test apparatus and methods of behavioral testing is described in Ford et al., *Analgesia*, 1997, 3:111–118. An in vivo assay for measuring the pain response to cold allodynia model in neuropathic rats is described in Example 48.

The apparatus for testing cold allodynia in neuropathic (CCI) rats consists of a Plexiglass chamber with a metal plate 6 cm from the bottom of the chamber. The chamber is filled with ice and water to a depth of 2.5 cm above the metal plate, with the temperature of the bath maintained at 0–4° C. throughout the test.

Each rat is placed into the chamber individually, a timer started, and the animal's response latency was measured to the nearest tenth of a second. A "response" is defined as a rapid withdrawal of the right ligated hindpaw completely out of the water what the animal is stationary and not pivoting. An exaggerated limp while the animal is walking and turning is not scored as a response. The animals' baseline scores for withdrawal of the ligated leg from the water typically range from 7–13 seconds. The maximum immersion time is 20 seconds with a 20-minute interval between trials.

Preferred compounds of this invention demonstrate selectivity for the $alpha_{1B}$-adrenoceptor subtype over the $alpha_{1A}$- and $alpha_{1D}$-adrenoceptor subtypes. In contrast to non-subtype-selective $alpha_1$-adrenoceptor antagonists, the $alpha_{1B}$-adrenoceptor selective antagonist compounds of this invention do not demonstrate any significant cardiovascular effects in vivo at therapeutically effective doses. The compounds of this invention can selectively reduce or alleviate urinary tract disorders or symptoms, or ameliorate nociceptive and/or neurogenic pain, without producing the blood pressure lowering effects and/or the postural hypotension that are associated with previously described $alpha_1$-adrenoceptor antagonists.

EXAMPLES

The following preparations and examples are given to enable those skilled in the art to more clearly understand and practice the present invention. They should not be considered as limiting the scope of the invention, but merely as being illustrative and representative thereof.

Example 1

Furan-2-carboxylic acid methyl-(6-methylamino-hexyl)-amide 10

In accordance with the general Scheme 2B, the following is the preparation of a compound of Structure 4B, wherein each of $R^{2a}$ and $R^{2b}$ are methyl, $R^{2c}$ is hydrogen, m=6; and Y is furan-2-carbonyl.

A solution of di-tert-butyl dicarbonate (7.85 g, 36 mmol) in dichloromethane (100 mL) was added to a solution of N,N'-dimethyl-1,6-hexanediamine (7.2 g, 50 mmol) in dichloromethane (250 mL) solution at −78° C. under nitrogen. After addition was complete, the cool-bath was removed and the resulting mixture was stirred (6 h) and warmed up to room temperature. The reaction mixture was washed with water (120 mL), the dichloromethane layer was separated, dried over anhydrous magnesium sulfate, filtered and concentrated under reduced pressure. The residue was purified by chromatography on silica gel (eluent dichloromethane:methanol: $Et_3N$ 90:8:2) to yield N-tert-butoxycarbonyl-N,N'-dimethyl-1,6-hexanediamine.

2-Furanoyl chloride (3.75 mL, 38 mmol) was added dropwise, at 0° C., to a mixture of N-tert-butoxycarbonyl- N,N'-dimethyl-1,6-hexanediamine (9.3 g, 38 mmol) and triethylamine (8.4 mL, 60 mmol) in dichloromethane (120 mL). The resulting mixture was stirred (2 h). The reaction mixture was washed with water (2×20 mL), brine (20 mL), dried over $Na_2SO_4$, and concentrated under reduced pressure. The residue was treated with 50% trifluoroacetic acid/dichloromethane (100 mL) overnight. Trifluoroacetic acid and dichloromethane were removed under reduced pressure and the residue was azeotroped with toluene (50 mL). The residue was dissolved in dichloromethane (120 mL), treated carefully with excess $NaHCO_3$ (aqueous), the organic layer separated and the aqueous layer extracted with dichloromethane (2×50 mL). The combined organic layers were washed with water, brine and dried over $Na_2SO_4$. After removing the solvent, the residue was dried under vacuum to give the desired product 10 (7.8 g). $MH^+$ 239.2, $^1H$ NMR ($CDCl_3$) δ7.50 (s, 1H), 7.0 (d, 1H), 6.50 (d, 1H), 3.55 (br. s, 3H), 3.0–3.3 (m, 4H), 2.4 5(s, 3H), 1.35–1.75 (m, 8H).

Similarly, substituting N,N-dimethyl-1,6-hexanediamine with a diamine, as described in Formulas (A), (B) and/or (C) herein, and following the procedure described in Example 1 the following compounds were prepared:

Furan-2-yl-(octahydro-quinoxalin-1-yl)-methanone 12 ($MH^+$ 235);
[1,4]Diazepan-1-yl-furan-2-yl-methanone 14 ($MH^+$ 195);
Furan-2-yl-piperazin-1-yl-methanone 16 ($MH^+$ 181);
Furan-2-carboxylic acid methyl-(2-methylamino-ethyl)-amide 18 ($MH^+$ 183); and
(2,5-Dimethyl-piperazin-1-yl)-furan-2-yl-methanone 20 ($MH^+$ 281).

Example 2

4-[4-(Furan-2-carbonyl)-piperazin-1-ylmethylene]-2-naphthalen-1-yl-4H-oxazol-5-one 22

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is furan-2-carbonyl; and $R^1$ is naphthyl.

A 0.25 M acetonitrile solution of 4-ethoxymethylene-2-naphthalen-1-yl-4H-oxazol-5-one (200 μL) was added to a 0.25 M acetonitrile solution of 1-(2-furanoyl)piperazine (200 μL). The reaction vessel was sealed and the mixture shaken at 55° C. overnight. The volatile materials were removed under reduced pressure to yield the desired product 22 ($MH^+$ 402).

Similarly, substituting 1-(2-furanoyl)piperazine with other amines prepared using Example 1, and 4-ethoxymethylene-2-naphthalen-1-yl-4H-oxazol-5-one with other oxazolones, utilizing the procedure described in Example 2 the following compounds were prepared:

Furan-2-carboxylic acid methyl-{6-[methyl-(2-naphthalen-1-yl-5-oxo-oxazol-4-ylidenemethyl)-amino]-hexyl}-amide 24 ($MH^+$ 460);
4-[4-(Furan-2-carbonyl)-octahydro-quinoxalin-1-ylmethylene]-2-(3-methoxy-phenyl)-4H-oxazol-5-one 26 ($MH^+$ 436);
4-[4-(Furan-2-carbonyl)-2,5-dimethyl-piperazin-1-ylmethylene]-2-naphthalen-1-yl-4H-oxazol-5-one 28 ($MH^+$ 430);
Furan-2-carboxylic acid (6-{[2-(3-methoxy-phenyl)-5-oxo-oxazol-4-ylidenemethyl]-methyl-amino}-hexyl)-methyl-amide 30 ($MH^+$ 440);
4-[4-(Furan-2-carbonyl)-octahydro-quinoxalin-1-ylmethylene]-2-m-tolyl-4H-oxazol-5-one 32 ($MH^+$ 420);
Furan-2-carboxylic acid methyl-{6-[methyl-(5-oxo-2-m-tolyl-oxazol-4-ylidenemethyl)-amino]-hexyl}-amide 34 ($MH^+$ 424);
Furan-2-carboxylic acid (6-{[2-(2-chloro-phenyl)-5-oxo-oxazol-4-ylidenemethyl]-methyl-amino}-hexyl)-methyl-amide 36 ($MH^+$ 444);
Furan-2-carboxylic acid (6-{[2-(4-chloro-phenyl)-5-oxo-oxazol-4-ylidenemethyl]-methyl-amino}-hexyl)-methyl-amide 38 ($MH^+$ 444);
Furan-2-carboxylic acid methyl-{6-[methyl-(5-oxo-2-phenyl-oxazol-4-ylidenemethyl)-amino]-hexyl}-amide 40 ($MH^+$ 410);
4-[4-(Furan-2-carbonyl)-2,5-dimethyl-piperazin-1-ylmethylene]-2-naphthalen-2-yl-4H-oxazol-5-one 42 ($MH^+$ 430);
Furan-2-carboxylic acid methyl-(6-{methyl-[5-oxo-2-(2-trifluoromethyl-phenyl)-oxazol-4-ylidenemethyl]-amino}-hexyl)-amide 44 ($MH^+$ 478);
Furan-2-carboxylic acid methyl-{6-[methyl-(5-oxo-2-o-tolyl-oxazol-4-ylidenemethyl)-amino]-hexyl}-amide 46 ($MH^+$ 424); and
2-Biphenyl-4-yl-4-[4-(furan-2-carbonyl)-[1,4]diazepan-1-ylmethylene]-4H-oxazol-5-one 48 ($MH^+$ 442).

Example 3

2-Naphthalen-1-yl-4-piperazin-1-ylmethylene-4H-oxazol-5-one 50

In accordance with the general Scheme 3A, the following is the preparation of a compound of Structure 8A, wherein each of $R^{2a}$, $R^{2b}$ and $R^{2c}$ is hydrogen, m=2, n=1; Z is NH; and $R^1$ is naphthyl.

A mixture of 4-ethoxymethylene-2-naphthalen-1-yl-4H-oxazol-5-one (4.0 g, 15 mmol) and N-tert-butoxycarbonyl-piperazine (2.8 g, 15 mmol) was refluxed in acetonitrile for 4 h. The reaction mixture was cooled to room temperature and the resulting yellow solid product (5.7 g) was collected by filtration. The yellow solid was then treated with 50% trifluoroacetic acid/dichloromethane (100 mL) overnight at room temperature, the solvents were removed under reduced pressure and the residue was azeotroped with toluene (50 mL). The residue was suspended in dichloromethane (100 mL) and aqueous $NaHCO_3$ (20 mL), the phases were separated and the aqueous layer was extracted further with dichloromethane (3×100 mL). The combined organic layers were dried over $Na_2SO_4$ and concentrated to yield the desired product 50 as a pale yellow solid (3.0 g). $MH^+$ 308.1, $^1H$ NMR: ($CDCl_3$) δ9.20 (d, 1H), 8.35 (d, 1H), 8.05 (m, 2H), 7.7 (m, 3H), 7.30 (s, 1H), 4.60 (m, 2H), 3.70 (m, 2H), 3.25 (m, 4H).

Similarly, substituting N-tert-butoxycarbonyl-piperazine with other suitably mono-protected diamines prepared using Example 1, and 4-ethoxymethylene-2-naphthalen-1-yl-4H-oxazol-5-one with other oxazolones, following the procedure described in Example 3, the following compounds were prepared:

2-Naphthalen-1-yl-4-(octahydro-quinoxalin-1-ylmethylene)-4H-oxazol-5-one 52 ($MH^+$ 362);
4-{[Methyl-(6-methylamino-hexyl)-amino]-methylene}-2-naphthalen-1-yl-4H-oxazol-5-one 54 ($MH^+$ 366);
4-[1,4]Diazepan-1-ylmethylene-2-naphthalen-1-yl-4H-oxazol-5-one 56 ($MH^+$ 322);
2-(3-Methoxy-phenyl)-4-piperazin-1-ylmethylene-4H-oxazol-5-one 58 ($MH^+$ 288);
2-(3-Methoxy-phenyl)-4-(octahydro-quinoxalin-1-ylmethylene)-4H-oxazol-5-one 60 ($MH^+$ 342);
2-(3-Methoxy-phenyl)-4-{[methyl-(6-methylamino-hexyl)-amino]-methylene}-4H-oxazol-5-one 62 ($MH^+$ 346); and
4-[1,4]Diazepan-1-ylmethylene-2-(3-methoxy-phenyl)-4H-oxazol-5-one 64 ($MH^+$ 302).

Example 4

4-[4-(Furan-2-carbonyl)-piperazin-1-ylmethylene]-2-naphthalen-1-yl-4H-oxazol-5-one 66

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is furan-2-carbonyl; and $R^1$ is naphthyl.

To a 0.125 M solution of 50, prepared as described in Example 3 (400 μL, 50 μmole), in methylene chloride was added a 1.25 M acetonitrile solution of Hünig's base (50 μL) followed by a 0.25 M solution of 2-furanoyl chloride in acetonitrile (200 μL, 50 μmole). The reaction vessel sealed, and the resulting mixture shaken at room temperature for 24 h. The solvent was removed to yield the desired product 66 ($MH^+$ 402).

Similarly, substituting 2-furanoyl chloride with other acid chlorides, and 50 prepared as described in Example 3 with other oxazolones, following the procedure described in Example 4, the following compounds were prepared:

Furan-2-carboxylic acid methyl-{6-[methyl-(2-naphthalen-1-yl-5-oxo-oxazol-4-ylidenemethyl)-amino]-hexyl}-amide 68 ($MH^+$ 460);

2-(3-Methoxy-phenyl)-4-[4-(3-methyl-benzoyl)-octahydro-quinoxalin-1-ylmethylene]-4H-oxazol-5-one 70 ($MH^+$ 460);

4-[4-(Furan-2-carbonyl)-octahydro-quinoxalin-1-ylmethylene]-2-naphthalen-1-yl-4H-oxazol-5-one 72 ($MH^+$ 456);

Furan-2-carboxylic acid (6-{[2-(3-methoxy-phenyl)-5-oxo-oxazol-4-ylidenemethyl]-methyl-amino}-hexyl)-methyl-amide 74 ($MH^+$ 440);

2-Naphthalen-1-yl-4-[4-(2-thiophen-2-yl-acetyl)-piperazin-1-ylmethylene]-4H-oxazol-5-one 76 ($MH^+$ 432);

4-[4-(3-Methyl-butyryl)-piperazin-1-ylmethylene]-2-naphthalen-1-yl-4H-oxazol-5-one 78 ($MH^+$ 392);

2-Naphthalen-1-yl-4-(4-phenylacetyl-[1,4]diazepan-1-ylmethylene)-4H-oxazol-5-one 80 ($MH^+$ 440);

2-(3-Methoxy-phenyl)-4-[4-(2-trifluoromethyl-benzoyl)-octahydro-quinoxalin-1-ylmethylene]-4H-oxazol-5-one 82 ($MH^+$ 514);

4-(4-Cyclohexanecarbonyl-piperazin-1-ylmethylene)-2-naphthalen-1-yl-4H-oxazol-5-one 84 ($MH^+$ 418);

3,N-Dimethyl-N-{6-[methyl-(2-naphthalen-1-yl-5-oxo-oxazol-4-ylidenemethyl)-amino]-hexyl}-butyramide 86 ($MH^+$ 450);

2-(3-Methoxy-phenyl)-4-[4-(4-methyl-benzoyl)-octahydro-quinoxalin-1-ylmethylene]-4H-oxazol-5-one 88 ($MH^+$ 460);

4-[4-(2-Chloro-benzoyl)-octahydro-quinoxalin-1-ylmethylene]-2-(3-methoxy-phenyl)-4H-oxazol-5-one 90 ($MH^+$ 480);

4-(4-Isobutyryl-piperazin-1-ylmethylene)-2-naphthalen-1-yl-4H-oxazol-5-one 92 ($MH^+$ 378);

2-Chloro-N-methyl-N-{6-[methyl-(2-naphthalen-1-yl-5-oxo-oxazol-4-ylidenemethyl)-amino]-hexyl}-benzamide 94 ($MH^+$ 504);

2-(3-Methoxy-phenyl)-4-[4-(3-methyl-butyryl)-octahydro-quinoxalin-1-ylmethylene]-4H-oxazol-5-one 96 ($MH^+$ 426);

4-[4-(2,4-Difluoro-benzoyl)-octahydro-quinoxalin-1-ylmethylene]-2-(3-methoxy-phenyl)-4H-oxazol-5-one 98 ($MH^+$ 482);

4-[4-(Furan-2-carbonyl)-octahydro-quinoxalin-1-ylmethylene]-2-(3-methoxy-phenyl)-4H-oxazol-5-one 100 ($MH^+$ 436);

2-Naphthalen-1-yl-4-[4-(pyridine-4-carbonyl)-piperazin-1-ylmethylene]-4H-oxazol-5-one 102 ($MH^+$ 413);

N-Methyl-N-{6-[methyl-(2-naphthalen-1-yl-5-oxo-oxazol-4-ylidenemethyl)-amino]-hexyl}-2-trifluoromethyl-benzamide 104 ($MH^+$ 538); and 4-[4-(2-Fluoro-benzoyl)-octahydro-quinoxalin-1-ylmethylene]-2-(3-methoxy-phenyl)-4H-oxazol-5-one 106 ($MH^+$ 464).

Example 5

4-(2-Naphthalen-1-yl-5-oxo-oxazol-4-ylidenemethyl)-piperazine-1-carboxylic acid (3-fluoro-phenyl)-amide 108

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is (3-fluoro-phenyl)-amide; and $R^1$ is naphthyl.

To a 0.125 M solution of 50, prepared as described in Example 3 (400 μL, 50 μmole), in methylene chloride was added a 0.25 M acetonitrile solution of 3-fluoro-phenyl isocyanate (200 μL, 50 μmole). The reaction vessel was sealed and the mixture shaken at room temperature for 24 h. Removal of the volatile materials under high vacuum yielded the desired product 108 ($MH^+$ 445).

Similarly, substituting 3-fluoro-phenyl isocyanate with other isocyanates and, prepared as described in Example 3, with other oxazolones, following the procedure described in Example 5, the following compounds were prepared:

4-(2-Naphthalen-1-yl-5-oxo-oxazol-4-ylidenemethyl)-piperazine-1-carboxylic acid m-tolylamide 110 ($MH^+$ 441);

4-(2-Naphthalen-1-yl-5-oxo-oxazol-4-ylidenemethyl)-piperazine-1-carboxylic acid (3-chloro-phenyl)-amide 112 ($MH^+$ 461);

4-[2-(3-Methoxy-phenyl)-5-oxo-oxazol-4-ylidenemethyl]-piperazine-1-carboxylic acid phenylamide 114 ($MH^+$ 407);

4-(2-Naphthalen-1-yl-5-oxo-oxazol-4-ylidenemethyl)-piperazine-1-carboxylic acid (3-methoxy-phenyl)-amide 116 ($MH^+$ 457);

4-[2-(3-Methoxy-phenyl)-5-oxo-oxazol-4-ylidenemethyl]-piperazine-1-carboxylic acid (3-chloro-phenyl)-amide 118 ($MH^+$ 441);

4-[2-(3-Methoxy-phenyl)-5-oxo-oxazol-4-ylidenemethyl]-piperazine-1-carboxylic acid m-tolylamide 120 ($MH^+$ 421);

4-[2-(3-Methoxy-phenyl)-5-oxo-oxazol-4-ylidenemethyl]-piperazine-1-carboxylic acid (3-fluoro-phenyl)-amide 122 ($MH^+$ 425);

4-[2-(3-Methoxy-phenyl)-5-oxo-oxazol-4-ylidenemethyl]-piperazine-1-carboxylic acid phenethyl-amide 124 ($MH^+$ 435);

4-(2-Naphthalen-1-yl-5-oxo-oxazol-4-ylidenemethyl)-[1,4]diazepane-1-carboxylic acid (3-fluoro-phenyl)-amide 126 ($MH^+$ 459);

1-Methyl-1-{6-[methyl-(2-naphthalen-1-yl-5-oxo-oxazol-4-ylidenemethyl)-amino]-hexyl}-3-m-tolyl-urea 128 ($MH^+$ 499);

4-(2-Naphthalen-1-yl-5-oxo-oxazol-4-ylidenemethyl)-piperazine-1-carboxylic acid cyclohexylamide 130 ($MH^+$ 433);

4-(2-Naphthalen-1-yl-5-oxo-oxazol-4-ylidenemethyl)-piperazine-1-carboxylic acid isopropylamide 132 ($MH^+$ 393);

4-(2-Naphthalen-1-yl-5-oxo-oxazol-4-ylidenemethyl)-piperazine-1-carboxylic acid ethylamide 134 ($MH^+$ 379);

4-(2-Naphthalen-1-yl-5-oxo-oxazol-4-ylidenemethyl)-piperazine-1-carboxylic acid tert-butylamide 136 ($MH^+$ 407);

4-(2-Naphthalen-1-yl-5-oxo-oxazol-4-ylidenemethyl)-piperazine-1-carboxylic acid allylamide 138 (MH⁺ 391);

4-(2-Naphthalen-1-yl-5-oxo-oxazol-4-ylidenemethyl)-piperazine-1-carboxylic acid (2-ethoxy-phenyl)-amide 140 (MH⁺ 471);

4-(2-Naphthalen-1-yl-5-oxo-oxazol-4-ylidenemethyl)-piperazine-1-carboxylic acid (2-fluoro-phenyl)-amide 142 (MH⁺ 445);

4-(2-Naphthalen-1-yl-5-oxo-oxazol-4-ylidenemethyl)-piperazine-1-carboxylic acid (3-cyano-phenyl)-amide 144 (MH⁺ 452);

4-(2-Naphthalen-1-yl-5-oxo-oxazol-4-ylidenemethyl)-piperazine-1-carboxylic acid (tetrahydro-pyran-2-yl)-amide 146 (MH⁺ 435); and 3-{[4-(2-Naphthalen-1-yl-5-oxo-oxazol-4-ylidenemethyl)-piperazine-1-carbonyl]-amino}-propionic acid ethyl ester 148 (MH⁺ 451).

Example 6

2-Naphthalen-1-yl-4-[4-(quinoline-8-sulfonyl)-piperazin-1-ylmethylene]-4H-oxazol-5-one 150

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is quinoline-8-sulfonyl; and $R^1$ is naphthyl.

To a 0.125 M solution of 50, prepared as described in Example 3 (400 μL, 50 μmole), in methylene chloride was added a 1.25 M acetonitrile solution of Hünig's base (50 μL). A 0.25 M solution of 8-quinolinylsulfonyl chloride in acetonitrile (200 μL, 50 μmole) was added, the reaction vessel sealed and the resulting mixture shaken at room temperature for 24 h. The solvent was removed to yield the desired product 150 (MH⁺ 498).

Similarly, substituting 8-quinolinylsulfonyl chloride with other sulfonyl chlorides, and 50, prepared as described in Example 3, with other oxazolones, following the procedure described in Example 6, the following compounds were prepared:

N-Methyl-N-{6-[methyl-(2-naphthalen-1-yl-5-oxo-oxazol-4-ylidenemethyl)-amino]-hexyl}-methanesulfonamide 152 (MH⁺ 444);

N-[4-(Methyl-{6-[methyl-(2-naphthalen-1-yl-5-oxo-oxazol-4-ylidenemethyl)-amino]-hexyl}-sulfamoyl)-phenyl]-acetamide 154 (MH⁺ 562);

2-Naphthalen-1-yl-4-[4-(quinoline-8-sulfonyl)-[1,4]diazepan-1-ylmethylene]-4H-oxazol-5-one 156 (MH⁺ 513);

4-(4-Benzenesulfonyl-[1,4]diazepan-1-ylmethylene)-2-naphthalen-1-yl-4H-oxazol-5-one 158 (MH⁺461);

4-(4-Methanesulfonyl-[1,4]diazepan-1-ylmethylene)-2-naphthalen-1-yl-4H-oxazol-5-one 160 (MH⁺ 400);

4, Dimethyl-N-{6-[methyl-(2-naphthalen-1-yl-5-oxo-oxazol-4-ylidenemethyl)-amino]-hexyl}-benzenesulfonamide 162 (MH⁺ 520);

4-Chloro-N-methyl-N-{6-[methyl-(2-naphthalen-1-yl-5-oxo-oxazol-4-ylidenemethyl)-amino]-hexyl}-benzenesulfonamide 164 (MH⁺ 540);

N-Methyl-N-{6-[methyl-(2-naphthalen-1-yl-5-oxo-oxazol-4-ylidenemethyl)-amino]-hexyl}-benzenesulfonamide 166 (MH⁺ 506);

N-(6-{[2-(3-Methoxy-phenyl)-5-oxo-oxazol-4-ylidenemethyl]-methyl-amino}-hexyl)-N-methyl-methanesulfonamide 168 (MH⁺ 424);

5-Dimethylamino-naphthalene-1-sulfonic acid methyl-{6-[methyl-(2-naphthalen-1-yl-5-oxo-oxazol-4-ylidenemethyl)-amino]-hexyl}-amide 170 (MH⁺ 598); and 4-Methoxy-N-methyl-N-{6-[methyl-(2-naphthalen-1-yl-5-oxo-oxazol-4-ylidenemethyl)-amino]-hexyl}-benzenesulfonamide 172 (MH⁺ 536).

Example 7

4-(2-Naphthalen-1-yl-5-oxo-oxazol-4-ylidenemethyl)-piperazine-1-carboxylic acid isopropyl ester 174

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is isopropoxycarbonyl; and $R^1$ is naphthyl.

To a 0.125 M solution of 50, prepared as described in Example 3 (400 μL, 50 μmole), in methylene chloride was added a 1.25 M acetonitrile solution of Hünig's base (50 μL). A 0.25 M solution of isopropyl chloroformate in acetonitrile (200 μL, 50 μmole) was added the reaction vessel sealed and the resulting mixture shaken at room temperature for 24 h. The solvent was removed to yield the desired product 174 (MH⁺ 394).

Similarly, substituting isopropyl chloroformate with other chloroformates, and 50, prepared as described in Example 3 with other oxazolones, following the procedure described in Example 7, the following compounds were prepared:

Methyl-{6-[methyl-(2-naphthalen-1-yl-5-oxo-oxazol-4-ylidenemethyl)-amino]-hexyl}-carbamic acid methyl ester 176 (MH⁺ 424);

4-(2-Naphthalen-1-yl-5-oxo-oxazol-4-ylidenemethyl)-piperazine-1-carboxylic acid isopropyl ester 178 (MH⁺ 394);

(6-{[2-(3-Methoxy-phenyl)-5-oxo-oxazol-4-ylidenemethyl]-methyl-amino}-hexyl)-methyl-carbamic acid cyclopentyl ester 180 (MH⁺ 458);

4-(2-Naphthalen-1-yl-5-oxo-oxazol-4-ylidenemethyl)-piperazine-1-carboxylic acid cyclopentyl ester 182 (MH⁺ 420);

Methyl-{6-[methyl-(2-naphthalen-1-yl-5-oxo-oxazol-4-ylidenemethyl)-amino]-hexyl}-carbamic acid cyclopentyl ester 184 (MH⁺ 478);

(6-{[2-(3-Methoxy-phenyl)-5-oxo-oxazol-4-ylidenemethyl]-methyl-amino}-hexyl)-methyl-carbamic acid methyl ester 186 (MH⁺ 404);

Methyl-{6-[methyl-(2-naphthalen-1-yl-5-oxo-oxazol-4-ylidenemethyl)-amino]-hexyl}-carbamic acid isobutyl ester 188 (MH⁺ 466);

(6-{[2-(3-Methoxy-phenyl)-5-oxo-oxazol-4-ylidenemethyl]-methyl-amino}-hexyl)-methyl-carbamic acid isobutyl ester 190 (MH⁺ 446);

Methyl-{6-[methyl-(2-naphthalen-1-yl-5-oxo-oxazol-4-ylidenemethyl)-amino]-hexyl}-carbamic acid p-tolyl ester 192 (MH⁺ 500); and (6-{[2-(3-Methoxy-phenyl)-5-oxo-oxazol-4-ylidenemethyl]-methyl-amino}-hexyl)-methyl-carbamic acid isopropyl ester 194 (MH⁺ 432).

Example 8

Piperazine-1-carboxylic acid phenylamide trifluoroacetate 196

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is N-phenylamide.

Phenyl isocyanate (3.50 g, 29.7 mmol) was added to a solution of N-tert-butoxycarbonyl-piperazine (5.03 g, 27 mmol) in acetonitrile. The mixture was refluxed (90 min), cooled to room temperature and evaporated under reduced pressure to yield a white solid (8.0 g). The resulting solid was dissolved in dichloromethane (15 mL), cooled to 0° C., and trifluoroacetic acid (15 mL) was added. The solution was stirred (2 h) and evaporated under reduced pressure to yield the desired product as its trifluoroacetate salt 196, as a clear colorless oil that crystallized on standing. $^1$H NMR: (DMSO d6) δ9.00 (s, 2H, exch. $D_2O$), 8.75 (s, 1H exch. $D_2O$), 7.45 (m, 2H), 7.21 (m, 2H), 7.00 (m, 1H), 3.66 (m, 4H), 3.14 (m, 4H).

Example 9

2-Benzyl-octahydro-pyrrolo[3,4-c]pyrrole 198

In accordance with the general Scheme 2C, the following is the preparation of a compound of Structure 4C, wherein each of p, q, r and s=1; and Y is benzyl.

Triethylamine (16.2 g, 0.16 mol) was added to a suspension of N-benzylmaleimide (25.0 g, 0.13 mol), N-benzylglycine hydrochloride (32.3 g, 0.16 mol) and paraformaldehyde (25.2 g, 0.84 mol) in benzene (1 L) in a mechanically stirred flask, under a nitrogen atmosphere. The resulting solution was refluxed (3.5 h), cooled to room temperature, dried over anhydrous magnesium sulfate, treated with decolorizing charcoal, filtered through Celite and evaporated under reduced pressure. The residue (52.9 g) was dissolved in 1,2-dichloroethane, and under a nitrogen atmosphere, sodium bicarbonate (22.4 g, 0.26 mol) was added followed by dropwise addition of 1-chloroethylchloroformate (38.18 g, 0.26 mol). The resulting mixture was refluxed overnight before cooling to room temperature. The solution was dried over anhydrous magnesium sulfate, treated with decolorizing charcoal, filtered through Celite and evaporated under reduced pressure. The residue was dissolved in anhydrous methanol (500 mL) and heated at 50° C. for 3 h. On cooling to room temperature the solution was concentrated to approximately half its volume yielding a precipitate. The solid was collected by filtration, washed on the filter with diethyl ether and dried under vacuum yielding a white crystalline solid (26.0 g).

A solution of the above mentioned solid (25.9 g) in tetrahydrofuran (250 mL) was added dropwise under a nitrogen atmosphere (over 1 h) to a solution of lithium aluminum hydride (1.0 M in tetrahydrofuran, 300 mL, 300 mmol) in tetrahydrofuran (200 mL) cooled to 0° C. The resulting slurry was warmed slowly, refluxed for 15 min, cooled and stirred overnight at room temperature. Water (11.3 mL) was added very carefully with stirring followed by 15% aqueous NaOH (11.3 mL). Additional water (34.1 mL) was added followed by anhydrous magnesium sulfate, and the mixture was stirred at room temperature, filtered through Celite and evaporated under reduced pressure to yield the desired product as a yellow oil 198 (18.7 g). $^1$H NMR: ($CDCl_3$) δ7.36–7.19 (m, 5H), 3.51 (s, 2H), 2.89–2.57 (m, 8H), 2.35–2.27 (m, 2H), 2.01 (br. s,1H, exch. $D_2O$).

Example 10

Hexahydro-pyrrolo[3,4-c]pyrrole-2-carboxylic acid phenylamide 200

In accordance with the general Scheme 2C, the following is the preparation of a compound of Structure 4C, wherein each of p, q, r and s=1; and Y is N-phenylamide.

To a solution of 198 (250 mg, 1.2 mmol), prepared as described in Example 9, in dichloromethane (5 mL) at 0° C., under a nitrogen atmosphere, was added N,N-diisopropylethylamine (175 mg, 1.4 mmol) followed by phenyl isocyanate (147 mg, 1.2 mmol). The reaction mixture was stirred at 0° C. for 4 h, diluted with dichloromethane (25 mL), washed with saturated aqueous ammonium chloride solution (5 mL), water (5 mL), and brine (5 mL), dried over anhydrous magnesium sulfate, filtered and evaporated under reduced pressure. Flash chromatography of the residue over silica gel (eluent dichloromethane:methanol, 93:7) yielded a white solid (247 mg).

To a solution of the resulting white solid (243 mg, 7.7 mmol) in ethanol (20 mL), ammonium formate (290 mg, 4.6 mmol) was added, followed by 10% palladium on activated carbon (100 mg) and the mixture was refluxed for 5 h. On cooling to room temperature, the mixture was filtered through Celite to yield the desired product as a white solid 200 (211 mg). $^1$H NMR: (DMSO d6) δ8.40 (br. s, 1H, exch. $D_2O$), 7.56 (m, 2H), 7.28 (m, 2H), 7.00 (m,1H), 3.74–2.96 (m, 10H).

Example 11

Piperazine-1-carboxylic acid pyridin-2-ylamide trifluoroacetate 202

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is N-pyridin-2-ylamide.

To a solution of 2-aminopyridine (2.50 g, 26.6 mmol) and triethylamine (4.05 mL) in dichloromethane (25 mL), cooled to −20° C., was added phenyl chloroformate (3.65 mL, 29.2 mmol). The mixture was stirred at −20° C. for 1 h, warmed up to room temperature and washed with aqueous solution of saturated $NaHCO_3$ (100 mL). The organic phase was separated, dried over anhydrous magnesium sulfate, filtered and evaporated under reduced pressure to yield a pale yellow solid (6.05 g).

To a solution of the resulting pale yellow solid (5.57 g, 26 mmol) in DMF (100 mL), triethylamine (3.80 mL, 27.5 mmol) was added, followed by N-tert-butoxycarbonyl-piperazine (5.1 g, 27.5 mmol). The mixture was heated at 100° C. for 1 hour, cooled to room temperature and evaporated under reduced pressure. The residue was purified by flash chromatography over silica gel (eluent hexane:ethyl acetate 50:50) to yield a white solid (4.15 g).

The resulting white solid (4.0 g, 13 mmol) was dissolved in 1:1 trifluoroacetic acid:dichloromethane and the mixture stirred at room temperature for 2 h before removal of the volatile materials by evaporation under reduced pressure. Recrystallization of the residue from ethanol/diethyl ether yielded the trifluoroacetic acid salt of the desired product as a white solid 202 (5.02 g). $^1$H NMR: (DMSO d6) δ9.02 (br. s,1H, exch. $D_2O$), 8.28 (m,1H), 7.84 (m,1H), 7.75 (m, 1H), 7.10 (m, 1H), 3.69 (m, 4H), 3.15 (m, 4H).

Similarly, replacing 2-aminopyridine with 4-aminopyridine and following the procedure outlined in Example 11 the trifluoroacetate salt of piperazine-1-carboxylic acid pyridin-4-ylamide 204 was obtained as a thick syrup. $^1$H NMR: (DMSO d6) δ9.37 (s, 2H), 8.85 (m, 2H), 8.18 (m, 2H), 3.98 (m, 4H), 3.44 (m, 4H).

Example 12

Piperazine-1-carboxylic acid pyridin-3-ylamide trifluoroacetate 206

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is N-pyridin-3-ylamide.

Cold concentrated aqueous HCl (2.43 mL) was added to nicotinyl hydrazide (2.0 g, 15.6 mmol) cooled to 0° C. in an ice bath. To the resulting mixture a solution of sodium nitrite (2.0 g, 29.1 mmol) in water (3.3 mL) was added dropwise. On completion of addition a green solution was formed. The solution was extracted with diethyl ether (2×30 mL) and the aqueous phase neutralized carefully with solid sodium bicarbonate. The resulting basic solution was extracted with diethyl ether (2×20 mL), the ether extracts combined, washed with aqueous saturated $NaHCO_3$, dried over $CaCl_2$/$CaSO_4$ for 30 min and evaporated under reduced pressure without warming to yield a residue. The residue was dissolved in toluene (43 mL) and refluxed for 80 min, cooled to room temperature, added to a solution of N-tert-butoxycarbonyl-piperazine (1.5 g, 8.3 mmol) in dichloromethane (43 mL) and stirred at room temperature overnight. The resulting yellow solution was evaporated under reduced pressure and the residue purified by flash chromatography over silica gel (eluent dichloromethane:methanol, 95:5) to yield a pale yellow solid (1.94 g).

Trifluoroacetic acid (8 mL) was added to a solution of the pale yellow solid (1.90 g) in dichloromethane (8 mL). The reaction mixture was stirred at room temperature for 1 h and evaporated to yield the trifluoroacetic acid salt of the desired product 206 (4.20 g). $^1$H NMR: (DMSO d6) $\delta$9.67 (s, 1H), 9.02 (m, 1H), 8.50 (m, 1H), 8.38 (m, 1H), 7.88 (m, 1H), 3.71 (m, 4H), 3.18 (m, 4H).

Example 13

4-(2-Naphthalen-1-yl-5-oxo-oxazol-4-ylidenemethyl)-piperazine-1-carboxylic acid phenylamide 208

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is N-phenylamide; and $R^1$ is naphthyl.

A 0.1 M solution of 4-ethoxymethylene-2-naphthalen-1-yl-4H-oxazol-5-one in DMSO (500 μL, 50 μmole) was added to a 0.15 M solution of 196 (333 μL, 50 μmole), prepared as described in Example 8. The reaction vessel was sealed and the resulting mixture shaken at room temperature overnight to yield the desired product as a DMSO solution 208 ($MH^+$ 427).

Similarly, substituting 4-ethoxymethylene-2-naphthalen-1-yl-4H-oxazol-5-one with other oxazolones and following the procedure described in Example 13, the following compounds were prepared:

4-[2-(4-Fluoro-naphthalen-1-yl)-5-oxo-oxazol-4-ylidenemethyl]-piperazine-1-carboxylic acid phenylamide 212 ($MH^+$ 445);

4-(5-Oxo-2-quinolin-4-yl-oxazol-4-ylidenemethyl)-piperazine-1-carboxylic acid phenylamide 214 ($MH^+$ 428);

4-[2-(3-Methoxy-phenyl)-5-oxo-oxazol-4-ylidenemethyl]-piperazine-1-carboxylic acid phenylamide 216 ($MH^+$ 407);

4-(2-Biphenyl-4-yl-5-oxo-oxazol-4-ylidenemethyl)-piperazine-1-carboxylic acid phenylamide 218 ($MH^+$ 453);

4-(5-Oxo-2-o-tolyl-oxazol-4-ylidenemethyl)-piperazine-1-carboxylic acid phenylamide 220 ($MH^+$ 391);

4-[2-(1-Methyl-1H-indol-2-yl)-5-oxo-oxazol-4-ylidenemethyl]-piperazine-1-carboxylic acid phenylamide 222 ($MH^+$ 430);

4-(5-Oxo-2-m-tolyl-oxazol-4-ylidenemethyl)-piperazine-1-carboxylic acid phenylamide 224 ($MH^+$ 391);

4-[2-(3-Methoxy-phenyl)-5-oxo-oxazol-4-ylidenemethyl]-piperazine-1-carboxylic acid phenylamide 226 ($MH^+$ 407);

4-[2-(2-Chloro-phenyl)-5-oxo-oxazol-4-ylidenemethyl]-piperazine-1-carboxylic acid phenylamide 228 ($MH^+$ 411);

4-[5-Oxo-2-(2-trifluoromethyl-phenyl)-oxazol-4-ylidenemethyl]-piperazine-1-carboxylic acid phenylamide 230 ($MH^+$ 445);

4-(5-Oxo-2-phenyl-oxazol-4-ylidenemethyl)-piperazine-1-carboxylic acid phenylamide 232 ($MH^+$ 377);

4-(2-Benzo[b]thiophen-2-yl-5-oxo-oxazol-4-ylidenemethyl)-piperazine-1-carboxylic acid phenylamide 234 ($MH^+$ 433);

4-[5-Oxo-2-(3-trifluoromethyl-phenyl)-oxazol-4-ylidenemethyl]-piperazine-1-carboxylic acid phenylamide 236 ($MH^+$ 445);

4-[2-(2,3-Dichloro-phenyl)-5-oxo-oxazol-4-ylidenemethyl]-piperazine-1-carboxylic acid phenylamide 238 ($MH^+$ 445); and 4-[2-(2,4-Dichloro-phenyl)-5-oxo-oxazol-4-ylidenemethyl]-piperazine-1-carboxylic acid phenylamide 240 ($MH^+$ 445).

Example 14

4-[2-(2,3-Dihydro-benzofuran-7-yl)-5-oxo-oxazol-4-ylidenemethyl]-piperazine-1-carboxylic acid phenylamide 242

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is N-phenylamide; and $R^1$ is 2,3-dihydro-benzofuran-7-yl.

To a suspension of 196 (227 mg, 0.71 mmol), prepared as described in Example 8, and 2-(2,3-dihydro-benzofuranoyl-7-yl)-4-ethoxymethylene-4H-oxazol-5-one (185 mg, 0.71 mmol) in acetonitrile (5 mL), N,N-diisopropylethylamine (184 mg, 1.42 mmol) was added, and the mixture stirred at room temperature for 2 h. The desired product 242 (115 mg) was collected by filtration and dried under vacuum. $MH^+$419, $^1$H NMR: (DMSO d6) $\delta$8.64 (s, 1H, exch. $D_2O$), 7.22–7.58 (m, 7H), 6.95 (m, 2H), 4.65 (m, 2H), 4.38 (m, 2H), 3.67 (m, 2H), 3.38 (m, 4H), 3.19 (m, 2H)

Similarly, substituting 196 for other substituted amines, and 2-(2,3-dihydro-benzofuran-7-yl)-4-ethoxymethylene-4H-oxazol-5-one with other oxazolones, following the procedure described in Example 14, the following compounds were prepared:

4-[2-(4-Fluoro-naphthalen-1-yl)-5-oxo-oxazol-4-ylidenemethyl]-piperazine-1-carboxylic acid phenylamide 212; $MH^+$445; $^1$H NMR (DMSO d6) $\delta$9.30 (d, 1H), 8.68 (s, 1H), 8.15 (m, 2H), 7.78 (m, 2H), 7.50 (m, 4H), 7.28 (m,1H), 6.98 (m,1H 4.45 (m, 2H), 3.70 (m, 6H);

4-(2-Naphthalen-1-yl-5-oxo-oxazol-4-ylidenemethyl)-piperazine-1-carboxylic acid phenylamide 208; $MH^+$427; $^1$H NMR: (DMSO d6) $\delta$9.20 (d, 1H), 8.68 (s, 1H), 8.05 (m, 3H), 7.65 (m, 3H), 7.55 (s,1H), 7.48 (d, 2H), 7.25 (t, 2H), 6.95 (t, 1H), 4.45 (m, 2H), 3.70 (m, 6H);

4-[2-(7-Fluorobenzofuran-4-yl)-5-oxo-oxazol-4-ylidenemethyl]-piperazine-1-carboxylic acid phenylamide 248; $M^+$435; $^1$H NMR (DMSO d6) $\delta$8.73 (s, 1H, exch. $D_2O$), 8.29 (d,1H), 7.72 (m, 1H), 7.50 (m, 4H), 7.48 (m,1H), 7.25 (m, 2H), 6.95 (m, 1H), 3.73 (m, 2H), 3.73 (m, 4H), 3.66 (m, 2H);

4-(2-Benzofuran-4-yl-5-oxo-oxazol-4-ylidenemethyl)-piperazine-1-carboxylic acid phenylamide 250; $MH^+$416;

¹H NMR (DMSO d6) δ8.67 (br. s, 1H, exch. D₂O), 8.18 (d, 1H), 7.75 (m ,2H), 7.51 (m, 5H), 7.26 (m, 2H), 6.96 (m, 1H), 4.46 (m, 2H), 3.73 (m, 4H), 3.66 (m, 2H);

4-(2-Benzofuran-7-yl-5-oxo-oxazol-4-ylidenemethyl)-piperazine-1-carboxylic acid phenylamide 252 (MH⁺ 417);

4-[2-(2,3-Dihydro-benzofuran-4-yl)-5-oxo-oxazol-4-ylidenemethyl]-piperazine-1-carboxylic acid phenylamide 254 (M⁺ 418);

4-[2-(2,3-Dihydro-benzo[1,4]dioxin-5-yl)-5-oxo-oxazol-4-ylidenemethyl]-piperazine-1-carboxylic acid phenylamide 256 (MH⁺ 435);

4-(2-Benzo[1,3]dioxol-4-yl-5-oxo-oxazol-4-ylidenemethyl)-piperazine-1-carboxylic acid phenylamide 258 (MH⁺ 421);

4-(2-Naphthalen-1-yl-5-oxo-oxazol-4-ylidenemethyl)-piperazine-1-carboxylic acid pyridin-2-ylamide 260 (MH⁺ 428);

4-(2-Naphthalen-1-yl-5-oxo-oxazol-4-ylidenemethyl)-piperazine-1-carboxylic acid pyridin-3-ylamide 262 (M⁺ 427);

4-(2-Naphthalen-1-yl-5-oxo-oxazol-4-ylidenemethyl)-piperazine-1-carboxylic acid pyridin-4-ylamide 264 (MH⁺ 428);

4-(2-Naphthalen-1-yl-5-oxo-oxazol-4-ylidenemethyl)-piperazine-1-carboxylic acid (3-cyano-phenyl)-amide 266 (MH⁺ 452);

4-(2-Naphthalen-1-yl-5-oxo-oxazol-4-ylidenemethyl)-piperazine-1-carboxylic acid diphenylamide 268 (MH⁺ 517);

4-(2-Naphthalen-1-yl-5-oxo-oxazol-4-ylidenemethyl)-piperazine-1-carboxylic acid tert-butylamide 270 (MH⁺ 407); and 5-(2-Naphthalen-1-yl-5-oxo-oxazol-4-ylidenemethyl)-hexahydro-pyrrolo[3,4-c]pyrrole-2-carboxylic acid phenylamide 272 (MH⁺ 453).

Example 15

N-Pyridin-2-yl-piperazine-1-carboxamidine trifluoroacetate 274

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is N-pyridin-2-yl-carboxamidine.

A mixture of 1H-pyrrole-1-carboxamidine hydrochloride (4.40 g, 30 mmol), N-tert-butoxycarbonyl-piperazine (5.59 g, 30 mmol) and N,N-diisopropylethylamine (6.3 mL, 36 mmol) in 2-propanol (50 mL) was refluxed for 24 h. The volatile materials were removed on a rotavapor, the residue suspended in acetonitrile (50 mL) and filtered. The precipitate was further washed with acetonitrile (50 mL) to yield a white solid (6.2 g).

To a solution of the resulting white solid (37.29 g, 163 mmol), in dioxane (500 mL) sodium hydride (60% dispersion in mineral oil, 16.3 g, 407 mmol) was added under a nitrogen atmosphere, followed by 2-fluoropyridine (15.8 g, 163 mmol). The resulting mixture was refluxed for 90 min, cooled to room temperature and stirred overnight. Water was added carefully to quench the excess sodium hydride, and all of the volatile materials removed by evaporation under reduced pressure. Purification of the residue by flash chromatography over silica gel (eluent dichloromethane:methanol:NH₄OH, 95:5:0.5) yielded a pale solid (16.0 g).

Trifluoroacetic acid (40 mL) was added to a solution of the resulting pale solid (16.0 g, 52.4 mmol) in dichloromethane (40 mL), and the mixture was stirred for 2 h at room temperature. Removal of the volatile materials under reduced pressure followed by recrystallization of the residue from ethanol/diethyl ether yielded the trifluoroacetate salt of the desired product 274 (16.4g). ¹H NMR: (DMSO d6) δ9.35 (br. s,1H), 8.37 (m,1H), 7.93 (m,1H), 7.31 (m,1H), 7.23 (m,1H), 3.79 (m, 4H), 3.28 (m, 4H).

Example 16

4-(2-Naphthalen-1-yl-5-oxo-oxazol-4-ylidenemethyl)-N-pyridin-2-yl-piperazine-1-carboxamidine 276

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is N-pyridin-2-yl-carboxamidine; and $R^1$ is naphthyl.

A 0.125 M solution of 4-ethoxymethylene-2-naphthalen-1-yl-4H-oxazol-5-one in DMSO (200 μL, 25 μmole) was added to a 0.125 M solution of N-pyridin-2-yl-piperazine-1-carboxamidine (200 μL, 25 μmole). The reaction vessel was sealed and the resulting mixture shaken at 40° C. for 2 h to yield the desired product as a DMSO solution 276 (MH⁺ 427).

Similarly, substituting 4-ethoxymethylene-2-naphthalen-1-yl-4H-oxazol-5-one with other oxazolones, following the procedure described in Example 16, the following compounds were prepared:

4-[2-(4-Fluoro-naphthalen-1-yl)-5-oxo-oxazol-4-ylidenemethyl]-N-pyridin-2-yl-piperazine-1-carboxamidine 278 (MH⁺ 445);

4-(5-Oxo-2-quinolin-4-yl-oxazol-4-ylidenemethyl)-N-pyridin-2-yl-piperazine-1-carboxamidine 280 (MH⁺ 428);

4-[2-(3-Methoxy-phenyl)-5-oxo-oxazol-4-ylidenemethyl]-N-pyridin-2-yl-piperazine-1-carboxamidine 282 (MH⁺ 407);

4-[2-(2,3-Dichloro-phenyl)-5-oxo-oxazol-4-ylidenemethyl]-N-pyridin-2-yl-piperazine-1-carboxamidine 284 (MH⁺ 446);

4-[2-(2,3-Dimethyl-phenyl)-5-oxo-oxazol-4-ylidenemethyl]-N-pyridin-2-yl-piperazine-1-carboxamidine 286 (MH⁺ 405);

4-[5-Oxo-2-(1-phenyl-cyclopentyl)-oxazol-4-ylidenemethyl]-N-pyridin-2-yl-piperazine-1-carboxamidine 288 (MH⁺ 445);

4-(5-Oxo-2-m-tolyl-oxazol-4-ylidenemethyl)-N-pyridin-2-yl-piperazine-1-carboxamidine 290 (MH⁺ 391);

4-(5-Oxo-2-o-tolyl-oxazol-4-ylidenemethyl)-N-pyridin-2-yl-piperazine-1-carboxamidine 292 (MH⁺ 391);

4-[2-(1-Methyl-1H-indol-2-yl)-5-oxo-oxazol-4-ylidenemethyl]-N-pyridin-2-yl-piperazine-1-carboxamidine 294 (MH⁺ 430);

4-[5-Oxo-2-(3-trifluoromethyl-phenyl)-oxazol-4-ylidenemethyl]-N-pyridin-2-yl-piperazine-1-carboxamidine 296 (MH⁺ 445);

4-(2-Benzo[b]thiophen-2-yl-5-oxo-oxazol-4-ylidenemethyl)-N-pyridin-2-yl-piperazine-1-carboxamidine 298 (MH⁺ 433);

4-(2-Benzofuran-2-yl-5-oxo-oxazol-4-ylidenemethyl)-N-pyridin-2-yl-piperazine-1-carboxamidine 300 (MH⁺ 418);

4-[2-(2-Chloro-phenyl)-5-oxo-oxazol-4-ylidenemethyl]-N-pyridin-2-yl-piperazine-1-carboxamidine 302 (MH⁺ 411);

4-[2-(4-Chloro-phenyl)-5-oxo-oxazol-4-ylidenemethyl]-N-pyridin-2-yl-piperazine-1-carboxamidine 304 (MH⁺ 411);

4-[5-Oxo-2-(1-phenyl-cyclopropyl)-oxazol-4-ylidenemethyl]-N-pyridin-2-yl-piperazine-1-carboxamidine 306 (MH⁺ 417);

4-[2-(3,4-Dimethoxy-phenyl)-5-oxo-oxazol-4-ylidenemethyl]-N-pyridin-2-yl-piperazine-1-carboxamidine 308 (MH$^+$ 437);

4-[2-(6-Methoxy-naphthalen-1-yl)-5-oxo-oxazol-4-ylidenemethyl]-N-pyridin-2-yl-piperazine-1-carboxamidine 310 (MH$^+$ 457);

4-(2-Naphthalen-2-yl-5-oxo-oxazol-4-ylidenemethyl)-N-pyridin-2-yl-piperazine-1-carboxamidine 312 (MH$^+$ 427);

4-(5-Oxo-2-phenyl-oxazol-4-ylidenemethyl)-N-pyridin-2-yl-piperazine-1-carboxamidine 314 (MH$^+$ 377); and 4-[5-Oxo-2-(2-trifluoromethyl-phenyl)-oxazol-4-ylidenemethyl]-N-pyridin-2-yl-piperazine-1-carboxamidine 316 (MH$^+$ 445).

Example 17

4-(2-Benzofuran-7-yl-5-oxo-oxazol-4-ylidenemethyl)-N-pyridin-2-yl-piperazine-1-carboxamidine hydrochloride 318

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is N-pyridin-2-yl-carboxamidine; and $R^1$ is 2-benzofuran-7-yl.

N,N-diisopropylethylamine (268 mg, 2.07 mmol) was added to a suspension of 274 (300 mg, 0.69 mmol), prepared as described in Example 15, and 2-benzofuran-7-yl-4-ethoxymethylene-4H-oxazol-5-one (178 mg, 0.69 mmol) in acetonitrile (10 mL), and the mixture stirred at room temperature for 1 h. The volatile materials were removed under reduced pressure and the residue recrystallized from ethano/diethyl ether saturated with gaseous HCl to yield the desired product as its hydrochloride salt 318 (235 mg). MH$^+$ 417; $^1$H NMR: (DMSO d6) δ8.37 (m, 1H), 8.14 (m, 1H), 7.93 (m, 1H), 7.85 (m, 2H), 7.53 (m, 2H), 7.39 (m, 1H), 7.25 (m, 1H), 7.10 (m, 1H), 4.58 (m, 2H), 4.11 (br. s, 2H), 3.88 (m, 6H).

Similarly, substituting 2-benzofuran-7-yl-4-ethoxymethylene-4H-oxazol-5-one with other oxazolones and following the procedure described in Example 17, the following compounds were prepared:

4-(2-Naphthalen-1-yl-5-oxo-oxazol-4-ylidenemethyl)-N-pyridin-2-yl-piperazine-1-carboxamidine hydrochloride 276; MH$^+$ 427; $^1$H NMR: (CD$_3$OD) δ9.20 (d, 1H), 8.32 (d, 1H), 8.08 (d, 1H), 7.90 (m, 3H), 7.50 (m, 3H), 7.40 (s,1H), 7.20 (m, 2H), 4.65 (m, 2H), 3.90 (m, 6H);

4-[2-(4-Fluoro-naphthalen-1-yl)-5-oxo-oxazol-4-ylidenemethyl]-N-pyridin-2-yl-piperazine-1-carboxamidine hydrochloride 278; MS: 445; $^1$H NMR: (CD$_3$OD) δ9.18 (d, 1H), 8.40 (d, 1H), 8.20 (m, 2H), 7.90 (m, 1H), 7.70 (m, 2H), 7.45 (s, 1H) 3H), 4.70 (m, 2H), 3.95 (m, 6H);

4-[2-(7-Fluoro-benzofuran-4-yl)-5-oxo-oxazol-4-ylidenemethyl]-N-pyridin-2-yl-piperazine-1-carboxamidine hydrochloride 324; MH$^+$ 435; $^1$H NMR (DMSO d6) δ8.57 (br. s,1H, exch. D$_2$O), 8,29 (d,1H), 8.13 (m, 1H), 7.71 (m, 1H), 7.50 (m, 3H), 7.37 (m, 1H), 6.76 (m, 2H), 4.44 (m, 2H), 3.80 (m, 2H), 3.75 (m, 4H);

4-(2-Benzofuran-4-yl-5-oxo-oxazol-4-ylidenemethyl)-N-pyridin-2-yl-piperazine-1-carboxamidine hydrochloride 326; MH$^+$ 417; $^1$H NMR (DMSO d6) δ10.87 (s, 1H, exch. D$_2$O), 8.37 (d, 1H), 8.20 (d, 1H), 7.93 (m, 1H), 7.75 (m, 2H), 7.59 (m, 1H), 7.55 (s, 1H), 7.43 (m, 2H), 7.25 (m, 1H), 4.58 (m, 2H), 3.90 (m, 6H);

4-[2-(2,3-Dihydro-benzo[1,4]dioxin-5-yl)-5-oxo-oxazol-4-ylidenemethyl]-N-pyridin-2-yl-piperazine-1-carboxamidine hydrochloride 328 (MH$^+$ 435); and 4-[2-(2,3-Dihydro-benzofuran-4-yl)-5-oxo-oxazol-4-ylidenemethyl]-N-pyridin-2-yl-piperazine-1-carboxamidine hydrochloride 330 (MH$^+$ 419).

Example 18

N-Phenyl-piperazine-1-carboxamidine trifluoroacetate 332

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is N-phenyl-carboxamidine.

Methyl iodide (301 g, 2.12 mol) was added dropwise, over 30 min, to a solution of phenyl thiourea (300 g, 1.93 mol) in ethanol (1.5 L). The resulting solution was refluxed for 1 hour and cooled to room temperature. Concentration of the solution to approximately half its volume yielded a white precipitate that was collected by filtration, washed on the filter with diethyl ether and dried to yield a white solid (532 g). The resulting white solid (200 g, 0.68 mol) was dissolved in 4 M aqueous sodium hydroxide (1 L) and the resulting solution extracted with chloroform (4×400 mL). The combined chloroform extracts were dried over anhydrous magnesium sulfate, filtered and evaporated under reduced pressure yielding a thick oil (92.7 g).

N-tert-butoxycarbonyl-piperazine (100 g, 0.54 mol) was added to a solution of the thick oil (89.1 g, 0.54 mol) in isopropanol (1 L), and the mixture refluxed overnight. The mixture was cooled to room temperature and the volatile materials removed under reduced pressure. Recrystallization of the residue from ethanol/H$_2$O yielded a white solid (82.0 g).

A solution of the white solid (25.7 g) in dichloromethane (125 mL) was cooled to 0° C. and trifluoroacetic acid (125 mL) added dropwise over 30 min. The ice bath was removed and the mixture was warmed up to room temperature and stirred for 1 h. Removal of the volatile materials under reduced pressure followed by recrystallization from ethanol/diethyl ether yielded the desired product as its trifluoroacetate salt 332. $^1$H NMR: (DMSO d6) δ9.08 (br. s, 1H, exch. D$_2$O), 8.22 (br. s, 1H, exch. D$_2$O), 7.53 (m, 2H), 7.34 (m, 3H), 3.78 (m, 4H), 3.36 (m, 4H).

Example 19

4-(2-Naphthalen-1-yl-5-oxo-oxazol-4-ylidenemethyl)-N-phenyl-piperazine-1-carboxamidine 334

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is N-phenyl-carboxamidine; and $R^1$ is naphthyl.

To a 0.25 M solution of N-phenyl-piperazine-1-carboxamidine (200 μL, 50 μmole) was added a 0.25 M solution of 4-ethoxymethylene-2-naphthalen-1-yl-4H-oxazol-5-one in DMSO (200 μL, 25 μmole). The reaction vessel was sealed and the resulting mixture shaken at room temperature for 1 h to yield the desired product as a DMSO solution 334 (MH$^+$ 426).

Similarly, substituting 4-ethoxymethylene-2-naphthalen-1-yl-4H-oxazol-5-one with other oxazolones and following the procedure described in Example 19, the following compounds were prepared:

4-[2-(4-Fluoro-naphthalen-1-yl)-5-oxo-oxazol-4-ylidenemethyl]-N-phenyl-piperazine-1-carboxamidine 336 (MH$^+$ 444);

4-(2-Benzofuran-4-yl-5-oxo-oxazol-4-ylidenemethyl)-N-phenyl-piperazine-1-carboxamidine 338 (MH+ 416);

4-[2-(3-Methoxy-phenyl)-5-oxo-oxazol-4-ylidenemethyl]-N-phenyl-piperazine-1-carboxamidine 340 (MH+ 406);

4-(5-Oxo-2-m-tolyl-oxazol-4-ylidenemethyl)-N-phenyl-piperazine-1-carboxamidine 342 (MH+ 390);

4-[2-(2,3-Dimethyl-phenyl)-5-oxo-oxazol-4-ylidenemethyl]-N-phenyl-piperazine-1-carboxamidine 344 (MH+ 404);

4-(5-Oxo-2-quinolin-4-yl-oxazol-4-ylidenemethyl)-N-phenyl-piperazine-1-carboxamidine 346 (MH+ 427);

4-(2-Benzo[b]thiophen-2-yl-5-oxo-oxazol-4-ylidenemethyl)-N-phenyl-piperazine-1-carboxamidine 348 (MH+ 432);

4-[2-(2,3-Dichloro-phenyl)-5-oxo-oxazol-4-ylidenemethyl]-N-phenyl-piperazine-1-carboxamidine 350 (MH+ 446);

4-[2-(3,4-Dimethoxy-phenyl)-5-oxo-oxazol-4-ylidenemethyl]-N-phenyl-piperazine-1-carboxamidine 352 (MH+ 436);

4-[2-(1-Methyl-1H-indol-2-yl)-5-oxo-oxazol-4-ylidenemethyl]-N-phenyl-piperazine-1-carboxamidine 354 (MH+ 429);

4-[2-(1H-Indol-4-yl)-5-oxo-oxazol-4-ylidenemethyl]-N-phenyl-piperazine-1-carboxamidine 356 (MH+ 416);

4-[5-Oxo-2-(2-trifluoromethyl-phenyl)-oxazol-4-ylidenemethyl]-N-phenyl-piperazine-1-carboxamidine 358 (MH+ 444);

4-(2-Naphthalen-2-yl-5-oxo-oxazol-4-ylidenemethyl)-N-phenyl-piperazine-1-carboxamidine 360 (MH+ 426);

4-[2-(2,4-Dichloro-phenyl)-5-oxo-oxazol-4-ylidenemethyl]-N-phenyl-piperazine-1-carboxamidine 362 (MH+ 445);

4-[2-(6-Methoxy-naphthalen-1-yl)-5-oxo-oxazol-4-ylidenemethyl]-N-phenyl-piperazine-1-carboxamidine 364 (MH+ 456);

4-(5-Oxo-2-o-tolyl-oxazol-4-ylidenemethyl)-N-phenyl-piperazine-1-carboxamidine 366 (MH+ 390);

4-[5-Oxo-2-(3,4,5-trimethoxy-phenyl)-oxazol-4-ylidenemethyl]-N-phenyl-piperazine-1-carboxamidine 368 (MH+ 467);

4-[2-(3-Methoxy-naphthalen-2-yl)-5-oxo-oxazol-4-ylidenemethyl]-N-phenyl-piperazine-1-carboxamidine 370 (MH+ 456);

4-[2-(4-Chloro-phenyl)-5-oxo-oxazol-4-ylidenemethyl]-N-phenyl-piperazine-1-carboxamidine 372 (MH+ 411); and 4-[2-(5-Fluoro-2-methyl-phenyl)-5-oxo-oxazol-4-ylidenemethyl]-N-phenyl-piperazine-1-carboxamidine 374 (MH+ 408).

Example 20

4-(2-Benzofuran-7-yl-5-oxo-oxazol-4-ylidenemethyl)-N-phenyl-piperazine-1-carboxamidine hydrochloride 376

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is N-phenyl-carboxamidine; and $R^1$ is 2-benzofuran-7-yl.

To a suspension of 332 (672 mg, 1.55 mmol) prepared as described in Example 18, and 2-benzofuran-7-yl-4-ethoxymethylene-4H-oxazol-5-one (400 mg, 1.55 mmol) in acetonitrile (15 mL) was added N,N-diisopropylethylamine (1.0 g, 7.77 mmol) and the mixture stirred at room temperature for 1 h. The volatile materials were removed under reduced pressure and the residue recrystallized from ethanol/diethyl ether saturated with gaseous HCl to yield the desired product as its hydrochloride salt 376 (202 mg). M+ 415, $^1$H NMR: (DMSO d6) δ8.17 (br. s, 1H, exch. $D_2O$), 8.11 (m, 1H), 7.82 (m, 2H), 7.53 (s, 1H), 7.48–7.36 (m, 3H), 7.29–7.23 (m, 3H), 7.09 (m, 1H), 4.57 (m, 2H), 3.87 (m, 2H), 3.77 (m, 4H).

Similarly, substituting 332 with other substituted amines, and 2-benzofuran-7-yl-4-ethoxymethylene-4H-oxazol-5-one with other oxazolones, following the procedure described in Example 20, the following compounds were prepared:

4-[2-(4-Fluoro-naphthalen-1-yl)-5-oxo-oxazol-4-ylidenemethyl]-N-phenyl-piperazine-1-carboxamidine hydrochloride 336; MH+ 444; $^1$H NMR: (DMSO d6) δ9.90 (s, 1H), 9.30 (d, 1H), 8.15 (m, 4H), 7.80 (m, 2H), 7.55 (s, 1H), 7.50 (m, 3H), 7.30 (m, 2H), 4.75 (m, 2H), 3.90 (m, 2H), 3.80 (m, 2H), 3.75 (m, 2H);

4-(2-Naphthalen-1-yl-5-oxo-oxazol-4-ylidenemethyl)-N-phenyl-piperazine-1-carboxamidine hydrochloride 334; MH+ 426; $^1$H NMR: ($CD_3OD$) δ9.25 (d, 1H), 8.15 (d, 1H), 8.05 (d, 1H), 7.95 (d, 1H), 7.50 (m, 6H), 7.35 (m, 3H), 4.70 (m, 2H), 3.95 (m, 6H);

4-[2-(7-Fluoro-benzofuran-4-yl)-5-oxo-oxazol-4-ylidenemethyl]-N-phenyl-piperazine-1-carboxamidine hydrochloride 382; MH+ 434; $^1$H NMR (DMSO d6) δ9.78 (s, 1H), 8.19 (d, 1H), 7.16 (m, 1H), 7.43 (s, 1H), 7.39–7.14 (m, 7H), 4.43 (m, 2H), 3.77 (m, 2H), 3.72 (m, 2H), 3.64 (m, 2H);

4-(2-Benzofuran-4-yl-5-oxo-oxazol-4-ylidenemethyl)-N-phenyl-piperazine-1-carboxamidine hydrochloride 338; MH+ 416; $^1$H NMR (DMSO d6) δ8.24 (br. s, 1H, exch. $D_2O$), 8.16 (d, 1H), 7.75 (m, 2H), 7.56 (s, 1H), 7.44 (m, 4H), 7.27 (m, 3H), 4.57 (m, 2H), 3.88 (m, 4H), 3.81 (m, 2H);

4-[2-(2,3-Dihydro-benzofuran-4-yl)-5-oxo-oxazol-4-ylidenemethyl]-N-phenyl-piperazine-1-carboxamidine hydrochloride 386 (MH+ 418);

4-(2-Naphthalen-1-yl-5-oxo-oxazol-4-ylidenemethyl)-N-thiophen-2-yl-piperazine-1-carboxamidine hydrochloride 388 (MH+ 432);

4-[2-(4-Fluoro-naphthalen-1-yl)-5-oxo-oxazol-4-ylidenemethyl]-N-thiophen-2-yl-piperazine-1-carboxamidine hydrochloride 390 (M+ 449);

4-(2-Naphthalen-1-yl-5-oxo-oxazol-4-ylidenemethyl)-N-o-tolyl-piperazine-1-carboxamidine hydrochloride 392 (M+ 439);

N-(3-Cyano-phenyl)-4-(2-naphthalen-1-yl-5-oxo-oxazol-4-ylidenemethyl)-piperazine-1-carboxamidine hydrochloride 394 (MH+ 451);

N-(3-Methoxy-phenyl)-4-(2-naphthalen-1-yl-5-oxo-oxazol-4-ylidenemethyl)-piperazine-1-carboxamidine hydrochloride 396 (M+ 455);

N-(2-Chloro-phenyl)-4-(2-naphthalen-1-yl-5-oxo-oxazol-4-ylidenemethyl)-piperazine-1-carboxamidine hydrochloride 398 (MH+ 460);

N-(4-Benzyloxy-phenyl)-4-(2-naphthalen-1-yl-5-oxo-oxazol-4-ylidenemethyl)-piperazine-1-carboxamidine hydrochloride 400 (MH+ 532); and 4-(2-Naphthalen-1-yl-5-oxo-oxazol-4-ylidenemethyl)-N,N-diphenyl-piperazine-1-carboxamidine hydrochloride 402 (MH+ 502).

Example 21

N-(4-Chloro-phenyl)-4-(2-naphthalen-1-yl-5-oxo-oxazol-4-ylidenemethyl)-piperazine-1-carboxamidine hydrochloride 404

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is N-(4-chloro-phenyl)-carboxamidine; and $R^1$ is naphthyl.

Triethylamine (154 mg, 1.52 mmol) was added to a suspension of 1-(4-chloro-phenyl)-2-methyl-isothiourea hydroiodide (200 mg, 0.6 mmol) and 50 (187 mg, 0.6 mmol), as produced in Example 3, in DMF (5 mL). The mixture was heated at reflux for 30 min, cooled to room temperature and the insoluble precipitate removed. The DMF solution was evaporated under reduced pressure and the residue purified by flash chromatography over silica gel (eluent dichloromethane:methanol:$NH_4OH$, 93:7:0.1) to yield a yellow oil. Further purification by preparative thin layer chromatography yielded the desired product as a yellow powder. Recrystallization from ethanoldiethyl ether saturated with gaseous HCl yielded the hydrochloride salt 404. $MH^+$ 460; $^1H$ NMR: (DMSO d6) $\delta$10.22 (s, 1H), 9.20 (d, 1H), 8.22 (br. s, 2H, exch. $D_2O$), 8.12–8.03 (m, 3H), 7.69–7.59 (m, 3H), 7.57 (s, 1H), 7.50 (d, 2H), 7.31 (d, 2H), 4.56 (m, 2H), 3.88 (m, 4H), 3.79 (m, 2H).

Similarly, substituting 1-(4-Chloro-phenyl)-2-methyl-isothiourea with other 2-methyl-isothiourea derivatives and following the procedure described in Example 21, the following compounds were prepared:

N-(4-Cyclohexyl-phenyl)-4-(2-naphthalen-1-yl-5-oxo-oxazol-4-ylidenemethyl)-piperazine-1-carboxamidine hydrochloride 406 ($MH^+$ 508);

4-(2-Naphthalen-1-yl-5-oxo-oxazol-4-ylidenemethyl)-N-m-tolyl-piperazine-1-carboxamidine hydrochloride 408 ($MH^+$ 440); and N-(2-Isopropyl-phenyl)-4-(2-naphthalen-1-yl-5-oxo-oxazol-4-ylidenemethyl)-piperazine-1-carboxamidine hydrochloride 410 ($MH^+$ 468).

Example 22

2-Piperazin-1-yl-1H-benzoimidazole trifluoroacetate 412

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is benzoimidazolyl.

A mixture of 2-chlorobenzimidazole (3.05 g, 20 mmol) and N-tert-butoxycarbonyl-piperazine (3.65 g, 19.6 mmol) in 1-butanol (40 mL) was refluxed for 6 h and cooled to room temperature. The resulting white precipitate (5.02 g) was collected by filtration and dried.

Trifluoroacetic acid (10 mL) was added to a solution of the white precipitate in dichloromethane (20 mL). The mixture was stirred at room temperature for 2 h and evaporated under reduced pressure. The residue was triturated with tert-butyl methyl ether and the resulting white precipitate collected by filtration to yield the desired product as it trifluoroacetate salt 412. $MH^+$ 203, $^1H$ NMR: (D2O) $\delta$7.48 (m, 2H), 7.38 (m, 2H), 3.98 (m, 4H), 3.55 (m, 4H).

Example 23

2-(Hexahydro-pyrrolo[3,4-c]pyrrol-2-yl)-1H-benzoimidazole hydrochloride 414

In accordance with the general Scheme 2C, the following is the preparation of a compound of Structure 4C, wherein each of p, q, r and s=1; and Y is benzoimidazolyl.

To a solution of 198 (3.0 g, 15 mmol), prepared as described in Example 9, in 1-butanol (30 mL), 2-chlorobenzimidazole (2.26 g, 15 mmol) was added, and the resulting solution was refluxed overnight under a nitrogen atmosphere. On cooling to room temperature the solution was evaporated under reduced pressure. The residue was dissolved in chloroform (100 mL), and washed with water (2×20 mL) and brine (2×20 mL). The organic layer was dried over anhydrous magnesium sulfate, filtered and evaporated under reduced pressure to yield a colorless foam (2.17 g).

To a solution the colorless foam (2.17 g, 6.8 mmol) in ethanol (100 mL), ammonium formate (4.29 g, 68.1 mmol) was added, followed by 10% palladium on carbon (1.0 g). The resulting mixture was refluxed for 3 h, cooled to room temperature, filtered through Celite and evaporated under reduced pressure to yield a white powder. Recrystallization of this powder from ethanol/diethyl ether saturated with gaseous HCl yielded the hydrochloride salt of the desired product 414 (1.32 g). $^1H$ NMR: (DMSO d6) $\delta$13.37 (br. s, 1H, exch. $D_2O$), 7.42 (m, 2H), 7.26 (m, 2H), 3.87–3.72 (m, 4H), 3.42–3.18 (m, 6H).

Example 24

4-[4-(1H-Benzoimidazol-2-yl)-piperazin-1-ylmethylene]-2-naphthalen-1-yl-4H-oxazol-5-one 416

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is benzoimidazol-2-yl; and $R^1$ is naphthyl.

A 0.25 M solution of 4-ethoxymethylene-2-naphthalen-1-yl-4H-oxazol-5-one in DMSO (200 μL, 25 μmole) was added to a 0.25 M solution of 2-piperazin-1-yl-1H-benzoimidazole (200 μL, 50 μmole). The reaction vessel was sealed and the resulting mixture shaken at room temperature for 1 h to yield the desired product as a DMSO solution 416 ($MH^+$ 424).

Similarly, substituting 4-ethoxymethylene-2-naphthalen-1-yl-4H-oxazol-5-one with other oxazolones, following the procedure described in Example 24, the following compounds were prepared:

4-[4-(1H-Benzoimidazol-2-yl)-piperazin-1-ylmethylene]-2-(4-fluoro-naphthalen-1-yl)-4H-oxazol-5-one 418 ($MH^+$ 442);

4-[4-(1H-Benzoimidazol-2-yl)-piperazin-1-ylmethylene]-2-(2,3-dichloro-phenyl)-4H-oxazol-5-one 420 ($MH^+$ 442);

4-[4-(1H-Benzoimidazol-2-yl)-piperazin-1-ylmethylene]-2-(3-methoxy-phenyl)-4H-oxazol-5-one 422 ($MH^+$ 404);

4-[4-(1H-Benzoimidazol-2-yl)-piperazin-1-ylmethylene]-2-m-tolyl-4H-oxazol-5-one 424 ($MH^+$ 388);

4-[4-(1H-Benzoimidazol-2-yl)-piperazin-1-ylmethylene]-2-(2,3-dimethyl-phenyl)-4H-oxazol-5-one 426 ($MH^+$ 402);

4-[4-(1H-Benzoimidazol-2-yl)-piperazin-1-ylmethylene]-2-(2-trifluoromethyl-phenyl)-4H-oxazol-5-one 428 ($MH^+$ 443);

4-[4-(1H-Benzoimidazol-2-yl)-piperazin-1-ylmethylene]-2-(2,3-difluoro-phenyl)-4H-oxazol-5-one 430 ($MH^+$ 409);

4-[4-(1H-Benzoimidazol-2-yl)-piperazin-1-ylmethylene]-2-o-tolyl-4H-oxazol-5-one 432 ($MH^+$ 388);

4-[4-(1H-Benzoimidazol-2-yl)-piperazin-1-ylmethylene]-2-(2-chloro-phenyl)-4H-oxazol-5-one 434 ($MH^+$ 408);

4-[4-(1H-Benzoimidazol-2-yl)-piperazin-1-ylmethylene]-2-(3,4-dimethoxy-phenyl)-4H-oxazol-5-one 436 ($MH^+$ 434);

4-[4-(1H-Benzoimidazol-2-yl)-piperazin-1-ylmethylene]-2-phenyl-4H-oxazol-5-one 438 ($MH^+$ 374);

4-[4-(1H-Benzoimidazol-2-yl)-piperazin-1-ylmethylene]-2-(3-trifluoromethyl-phenyl)-4H-oxazol-5-one 440 ($MH^+$ 441);

4-[4-(1H-Benzoimidazol-2-yl)-piperazin-1-ylmethylene]-2-(3-methoxy-naphthalen-2-yl)-4H-oxazol-5-one 442 (MH+ 454);

4-[4-(1H-Benzoimidazol-2-yl)-piperazin-1-ylmethylene]-2-thiophen-2-yl-4H-oxazol-5-one 444 (MH+ 380);

2-Benzo[1,3]dioxol-5-yl-4-[4-(1H-benzoimidazol-2-yl)-piperazin-1-ylmethylene]-4H-oxazol-5-one 446 (MH+ 417);

4-[4-(1H-Benzoimidazol-2-yl)-piperazin-1-ylmethylene]-2-naphthalen-2-yl-4H-oxazol-5-one 448 (MH+ 424);

4-[4-(1H-Benzoimidazol-2-yl)-piperazin-1-ylmethylene]-2-(4-chloro-phenyl)-4H-oxazol-5-one 450 (MH+ 408);

4-[4-(1H-Benzoimidazol-2-yl)-piperazin-1-ylmethylene]-2-(6-methoxy-naphthalen-1-yl)-4H-oxazol-5-one 452 (MH+ 454);

2-Benzo[b]thiophen-2-yl-4-[4-(1H-benzoimidazol-2-yl)-piperazin-1-ylmethylene]-4H-oxazol-5-one 454 (MH+ 430); and 4-[4-(1H-Benzoimidazol-2-yl)-piperazin-1-ylmethylene]-2-quinolin-3-yl-4H-oxazol-5-one 456 (MH+ 424).

Example 25

2-Benzofuran-4-yl-4-[4-(1H-benzoimidazol-2-yl)-piperazin-1-ylmethylene]-4H-oxazol-5-one 458

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is benzoimidazol-2-yl; and $R^1$ is 2-benzofuran-7-yl.

N,N-Diisopropylethylamine (403 mg, 3.1 mmol) was added to a suspension of 412 (246 mg, 0.78 mmol), prepared as described in Example 22, and 2-benzofuran-4-yl-4-ethoxymethylene-4H-oxazol-5-one (200 mg, 0.78 mmol) in acetonitrile (10 mL). The resulting mixture was stirred overnight at room temperature. The resulting yellow precipitate was filtered, washed with acetonitrile and dried under vacuum to yield the desired product 458 (186 mg). M+ 413, $^1$H NMR: (DMSO d6) δ8.20 (d, 1H), 7.77 (m, 2H), 7.53 (s, 1H), 7.45 (m, 2H), 7.25 (m, 2H), 6.97 (m, 2H), 2H), 3.84 (m, 4H), 3.72 (m, 2H).

Similarly, substituting 2-piperazin-1-yl-1H-benzoimidazole with other substituted amines, and 2-benzofuran-4-yl-4-ethoxymethylene-4H-oxazol-5-one with other oxazolones, following the procedure described in Example 25, the following compounds were prepared:

4-[4-(1H-Benzoimidazol-2-yl)-piperazin-1-ylmethylene]-2-(4-fluoro-naphthalen-1-yl)-4H-oxazol-5-one 418; MH+ 442; $^1$H NMR: (CD$_3$OD) δ9.25 (d, 1H), 8.15 (m, 2H), 7.66 (m, 2H), 7.60 (m, 6H), 4.70 (m, 2H), 3.90 (m, 6H);

4-[4-(1H-Benzoimidazol-2-yl)-piperazin-1-ylmethylene]-2-naphthalen-1-yl-4H-oxazol-5-one 416; MH+ 424; $^1$H NMR (DMSO d6) δ9.24 (d, 1H), 8.11 (m, 3H), 7.72–7.59 (m, 4H), 7.45 (m, 2H), 7.27 (m, 2H), 4.65 (m, 2H), 4.04 (m, 2H), 3.97 (m, 4H);

4-[4-(1H-Benzoimidazol-2-yl)-piperazin-1-ylmethylene]-2-(7-fluoro-benzofuran-4-yl)-4H-oxazol-5-one 464; MH+ 432; $^1$H NMR: (DMSO d6) δ8.30 (d, 1H), 7.73 (m, 1H), 7.53 (s, 1H), 7.51 (m, 1H), 7.37 (m, 1H), 7.23 (m, 2H), 6.95 (m, 2H), 4.54 (m, 2H), 3.84 (m, 4H), 3.72 (m, 2H);

4-[4-(1H-Benzoimidazol-2-yl)-piperazin-1-ylmethylene]-2-(2,3-dihydro-benzo[1,4]dioxin-5-yl)-4H-oxazol-5-one 466 (MH+ 432);

4-[4-(1H-Benzoimidazol-2-yl)-piperazin-1-ylmethylene]-2-(2,3-dihydro-benzofuran-4-yl)-4H-oxazol-5-one 468 (M+ 415);

2-Benzo[1,3]dioxol-4-yl-4-[4-(1H-benzoimidazol-2-yl)-piperazin-1-ylmethylene]-4H-oxazol-5-one 470 (MH+ 418);

4-[4-(6-Methoxy-1H-benzoimidazol-2-yl)-piperazin-1-ylmethylene]-2-naphthalen-1-yl-4H-oxazol-5-one 472 (MH+ 454);

2-(2,3-Dihydro-benzo[1,4]dioxin-5-yl)-4-[4-(6-methoxy-1H-benzoimidazol-2-yl)-piperazin-1-ylmethylene]-4H-oxazol-5-one 474 (MH+ 462);

4-(4-Benzooxazol-2-yl-piperazin-1-ylmethylene)-2-naphthalen-1-yl-4H-oxazol-5-one 476 (MH+ 25);

4-(4-Benzothiazol-2-yl-piperazin-1-ylmethylene)-2-naphthalen-1-yl-4H-oxazol-5-one 478 (MH+ 441);

4-[4-(1H-Benzoimidazol-2-ylmethyl)-piperazin-1-ylmethylene]-2-naphthalen-1-yl-4H-oxazol-5-one 480 (MH+ 438); and 2-Benzofuran-4-yl-4-[5-(1H-benzoimidazol-2-yl)-hexahydro-pyrrolo[3,4-c]pyrrol-2-ylmethylene]-4H-oxazol-5-one 482 (M+ 439).

Example 26

4-[4-(1H-Benzoimidazol-2-yl)-piperazin-1-ylmethylene]-2-naphthalen-1-yl-4H-oxazol-5-one 416

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is benzoimidazol-2-yl; and $R^1$ is naphthyl.

A mixture of 2-chlorobenzoimidazole (218 mg, 1.43 mmol) and (200 mg, 0.65 mmol), as produced in Example 3, in 1-butanol was heated to 100° C. overnight. The resulting yellow precipitate was filtered and washed with hot 1-butanol to yield the desired product 416 (240 mg). MH+ 424; $^1$H NMR (DMSO d6) δ9.22 (d, 1H), 8.10 (m, 4H), 7.65 (m, 5H), 7.50 (m, 3H), 7.30 (m, 2H), 7.40 (m, 2H), 4.65 (m, 2H) (m, 6H).

Similarly, substituting 2-chlorobenzoimidazole with other substituted imidazoles and following the procedure described in Example 26, the following examples were prepared:

4-[4-(3H-Imidazo[4,5-b]pyridin-2-yl)-piperazin-1-ylmethylene]-2-naphthalen-1-yl-4H-oxazol-5-one hydrochloride 486 (M+ 425);

4-[4-(3H-Imidazo[4,5-c]pyridin-2-yl)-piperazin-1-ylmethylene]-2-naphthalen-1-yl-4H-oxazol-5-one hydrochloride 488 (M+ 425); and 4-[4-(5-Chloro-1H-benzoimidazol-2-yl)-piperazin-1-ylmethylene]-2-naphthalen-1-yl-4H-oxazol-5-one hydrochloride 490 (M+ 458).

Example 27

4-[4-(1-Methyl-1H-benzoimidazol-2-yl)-piperazin-1-ylmethylene]-2-naphthalen-1-yl-4H-oxazol-5-one 492

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is 1-methyl-benzoimidazol-2-yl; and $R^1$ is naphthyl.

To a solution of 416 (43 mg, 0.1 mmol) prepared as described in Example 26, in DMF (1 mL) sodium carbonate (10 mg, 0.1 mmol) was added, followed by iodomethane (62 mL, 0.1 mmol). The resulting mixture was stirred at 70° C. for 24 h, cooled to room temperature and the volatile materials were removed under reduced pressure to yield a yellow solid. The yellow solid was partitioned between chloroform and water, the organic phase separated, dried over anhydrous magnesium sulfate, filtered and evaporated under reduced pressure to yield an orange residue. Recrystallization of the orange residue from methanol yielded yellow crystals of the desired product 492 (15 mg). MH+ 438; $^1$H NMR: (DMSO d6) δ9.19 (d, 1H), 8.08 (m, 3H), 7.63 (m, 3H), 7.57 (s, 1H), 7.38 (m, 2H), 7.12 (m, 2H), 4.64 (m, 2H), 3.93 (m, 2H), 3.68 (s, 3H), 3.47 (m, 4H).

Example 28

1-(4,5-Dihydro-1H-imidazol-2-yl)-piperazine trifluoroacetate 494

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is 4,5-dihydro-1H-imidazol-2-yl.

2-Chloro-4,5-dihydro-1H-imidazole sulfate (10.0 g, 49.3 mmol) was partitioned between saturated aqueous NaHCO$_3$ (200 mL) and diethyl ether (200 mL). The organic phase was separated and the aqueous phase further extracted with diethyl ether (2×100 mL). The combined diethyl ether extract was dried over anhydrous magnesium sulfate and filtered. This ether solution was added to a solution of N-tert-butoxycarbonyl-piperazine (9.20 g, 49.3 mmol) in isopropanol (200 mL). The diethyl ether was evaporated from the combined solutions using a rotavapor to yield a residue. The resulting residue was heated at reflux for 90 min, cooled to room temperature and reduced in volume to approximately 50 mL. Crystals precipitated from this solution on standing and were collected by filtration, washed on the filter with diethyl ether and dried under vacuum to yield the N-tert-butoxy carbonyl-protected intermediate (4.2 g).

The crystalline solid intermediate was dissolved in dichloromethane (20 mL). Trifluoroacetic acid (20 mL) was added to the solution and the reaction mixture was stirred for 2.5 h at room temperature. The volatile materials were removed under reduced pressure to yield a colorless oil that slowly crystallized on standing. Triturating with diethyl ether yielded the desired product (3.93 g) as its trifluoroacetate salt 494. MH+ 256; $^1$H NMR: (DMSO d6) δ8.74 (br. s, 1H, exch. D$_2$O), 3.64 (m, 4H), 3.35 (s, 4H), 3.23 (m, 4H).

Example 29

1-(4,5-Dihydro-oxazol-2-yl)-piperazine trifluoroacetate 496

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is 4,5-dihydro-oxazol-2-yl.

2-Chloroethyl isocyanate (3.4 g, 32.2 mmol) was added to a solution of N-tert-butoxycarbonyl-piperazine (5.0 g, 26.8 mmol) in tetrahydrofuran (30 mL) under a nitrogen atmosphere and the mixture was stirred overnight at room temperature. A small amount of solid precipitated into the reaction mixture. The resulting suspension was poured into vigorously stirring hexane (400 mL), the resulting precipitate collected by filtration and dried under vacuum to yield chloroethyl urea (7.40 g).

Potassium fluoride (40% by weight on alumina, 15.0 g) was added to a solution of (7.40 g, 25.4 mmol) in acetonitrile (160 mL), and the resulting mixture was refluxed overnight. The reaction mixture was filtered and evaporated under reduced pressure to yield a colorless oil (9.2 g).

Trifluoroacetic acid (35 mL) was added to a solution of the colorless oil in dichloromethane (35 mL) and the mixture stirred at room temperature for 4 h. The volatile materials were removed under vacuum to yield the desired product as its trifluoroacetate salt 496. $^1$H NMR: (DMSO d6) δ4.67 (m, 2H), 3.73 (m, 2H), 3.57 (m, 2H), 3.31 (m, 2H), 3.11 (m, 2H), 2.91 (m, 2H).

Example 30

2-Benzofuran-7-yl-4-[4-(4,5-dihydro-1H-imidazol-2-yl)-piperazin-1-ylmethylene]-4H-oxazol-5-one hydrochloride 498

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is 4,5-dihydro-1H-imidazol-2-yl; and $R^1$ is 2-benzofuran-7-yl.

N,N-Diisopropylethylamine (383 mg, 3 mmol) was added to a suspension of 494 (382 mg, 1 mmol), prepared as described in Example 28, and 2-benzofuran-7-yl-4-ethoxymethylene-4H-oxazol-5-one (257 mg, 1 mmol) in acetonitrile (10 mL), and the mixture was stirred at room temperature for 24 h. The resulting precipitate was collected by filtration and dried under vacuum. Recrystallization of the resulting solid from ethanol/diethyl ether saturated with gaseous HCl yielded the desired product (218 mg) as its hydrochloride salt 498. MH+ 366; $^1$H NMR: (DMSO d6) δ9.00 (br. s, 1H, exch. D$_2$O), 8.13 (d, 1H), 7.82 (m, 2H), 7.50 (s, 1H), 7.39 (t, 1H), 7.08 (d, 1H), 4.52 (m, 2H), 3.81 (m, 6H), 3.68 (s, 4H).

Similarly, substituting 1-(4,5-Dihydro-1H-imidazol-2-yl)-piperazine with other substituted amines, and 2-benzofuran-7-yl-4-ethoxymethylene-4H-oxazol-5-one with other oxazolones, following the procedure described in Example 30, the following compounds were prepared:

4-[4-(4,5-Dihydro-1H-imidazol-2-yl)-piperazin-1-ylmethylene]-2-(4-fluoro-naphthalen-1-yl)-4H-oxazol-5-one 500 (MH+ 394);

2-Benzofuran-4-yl-4-[4-(4,5-dihydro-1H-imidazol-2-yl)-piperazin-1-ylmethylene]-4H-oxazol-5-one 502 (MH+ 366);

2-(2,3-Dihydro-benzo[1,4]dioxin-5-yl)-4-[4-(4,5-dihydro-1H-imidazol-2-yl)-piperazin-1-ylmethylene]-4H-oxazol-5-one 504 (MH+ 384); and 4-[4-(4,5-Dihydro-oxazol-2-yl)-piperazin-1-ylmethylene]-2-naphthalen-1-yl-4H-oxazol-5-one 506 (MH+ 377).

Example 31

4-[4-(4,5-Dihydro-1H-imidazol-2-yl)-piperazin-1-ylmethylene]-2-naphthalen-1-yl-4H-oxazol-5-one 508

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is 4,5-dihydro-1H-imidazol-2-yl; and $R^1$ is naphthyl.

2-Chloro-4,5-dihydro-1H-imidazole sulfate (41 mg, 0.2 mmol) was partitioned between saturated aqueous NaHCO$_3$ and diethyl ether, the phases separated and the aqueous phase further extracted with diethyl ether. The combined diethyl ether extracts were dried over anhydrous magnesium sulfate, filtered and added to a solution of 50 prepared as described in Example 3 (61 mg, 0.2 mmol) in isopropanol. The diethyl ether was removed from the combined solution by evaporation under reduced pressure and the residue was refluxed for 10 min before cooling to room temperature to yield a yellow solid, which was collected by filtration and recrystallized from isopropanol yielding the desired product 508 (40 mg). MH$^+$ 376; $^1$H NMR: (CD$_3$OD) δ9.1 (d, 2H), 7.95–7.70 (m, 3H), 7.40 (m, 3H), 7.22 (s, 1H), (m, 2H), 3.60 (m 10H).

Example 32

4-[2-(4-Fluoro-naphthalen-1-yl)-5-oxo-oxazol-4-ylidenemethyl]-piperazine-1-carboxamidine hydrochloride 510

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is carboxamidine; and $R^1$ is 4-fluoro-1-naphthyl.

A solution of 4-ethoxymethylene-2-(4-fluoro-naphthalen-1-yl)-4H-oxazol-5-one (178 mg, 0.5 mmole) in tetrahydrofuran (5 mL) was added to a mixture of piperazine-1-carboxamidine (143 mg, 0.5 mmol) and triethylamine (210 μL) in tetrahydrofuran (10 mL) at 0° C. After 20 min, the solvents were removed and the residue dried. The residue was redissolved in tetrahydrofuran (5 mL) and treated with 4 M hydrochloric acid in dioxane (2 mL) at 0° C. A yellow precipitate was formed which was filtered, washed with tetrahydrofuran and dried under vacuum to afford the desired product 510 (125 mg). MH$^+$ 368.

Similarly, substituting 4-ethoxymethylene-2-(4-fluoro-naphthalen-1-yl)-4H-oxazol-5-one with other oxazolones and following the procedure described in Example 32, the following compound was prepared:

4-(2-Naphthalen-1-yl-5-oxo-oxazol-4-ylidenemethyl)-piperazine-1-carboxamidine hydrochloride 512 (MH$^+$ 351).

Example 33

N-Pyridin-4-yl-piperazine-1-carboxamidine trifluoroacetate 514

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is N-pyridin-4-yl-carboxamidine.

1,1-Thiocarbonyldiimidazole (29.4 g, 0.16 mol) was added to a solution of 4-aminopyridine (14.1 g, 0.15 mol) in anhydrous tetrahydrofuran (600 mL) and the resulting mixture stirred for 17 h. The solvent was removed under reduced pressure and the resulting solid suspended in a mixture of dichloromethane and water. Filtration of the undissolved solid followed by washing with acetone yielded a solid product (8.98 g).

Gaseous ammonia was bubbled through a solution of the resulting solid product (8.50 g, 0.06 mol) in anhydrous tetrahydrofuran (250 mL) for 20 min. The ammonia flow was discontinued and the mixture was stirred for 17 h during which time a precipitate was formed in the reaction. Filtration followed by drying the solid under vacuum yielded the desired thiourea product (5.1 g).

A mixture of the thiourea product (3.90 g, 26 mmol), N-tert-butoxycarbonyl-piperazine (4.84 g, 26 mmol) and 1,3-dicyclohexylcarbodiimide (5.90 g, 28 mmol) in dioxane (105 mL) was refluxed under a nitrogen for 48 h. The solvent was removed under reduced pressure and the residue sonicated in toluene and filtered. The residue was concentrated to approximately one third its volume and filtered to yield the N-tert-butoxycarbonyl-protected intermediate (660 mg). Trifluoroacetic acid (12.8 mL) was added to a suspension of the protected intermediate (656 mg) in dichloromethane (12.8 mL) and the resulting solution was stirred for 1 h. Removal of the volatile materials under reduced pressure followed by trituration with diethyl ether yielded the crystalline product (1.68 g) as its trifluoroacetate salt 514. MH$^+$ 206; $^1$H NMR (DMSO d6) δ9.2 (br. s, 1H), 8.75 (br. s, 1H), 8.5 (m, 1H), 7.32 (m, 1H), 3.75 (m, 4H), 3.40 (m, 4H).

Example 34

4-[2-(4-Fluoro-naphthalen-1-yl)-5-oxo-oxazol-4-ylidenemethyl]-N-pyridin-4-yl-piperazine-1-carboxamidine hydrochloride 516

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is n-pyridin-4-yl-carboxamidine; and $R^1$ is 4-fluoro-1-naphthyl.

Triethylamine (758 mg, 7.5 mmol) was added to a solution 514 (811 mg, 1.5 mmol), as produced in Example 33, in anhydrous tetrahydrofuran (6 mL) and the resulting suspension cooled to 0° C. A solution of 4-ethoxymethylene-2-(4-fluoro-naphthalen-1-yl)-4H-oxazol-5-one (428 mg, 1.5 mmol) in tetrahydrofuran (6 mL) was added and the mixture stirred for 1 h and evaporated under reduced pressure to yield a residue. The resulting residue was dissolved in tetrahydrofuran (5 mL) and 4 M hydrochloric acid in dioxane (2 mL) added. The resulting precipitate was collected by filtration, washed on the filter with 20% diethyl ether/methyl tert-butyl ether and dried under vacuum to yield the desired product 516 (349 mg). MH$^+$ 444; $^1$H NMR (DMSO d6) δ9.30 (m, 1H), 8.60 (m, 1H), 8.15 (m, 3H), 7.80 (m, 3H), 7.5 (m, 4H), 4.60 (m, 2H), 3.9 (m, 6H).

Similarly, substituting 4-ethoxymethylene-2-(4-fluoro-naphthalen-1-yl)-4H-oxazol-5-one with other oxazolones and following the procedure described in Example 34 the following compound was prepared:

4-(2-Naphthalen-1-yl-5-oxo-oxazol-4-ylidenemethyl)-N-pyridin-4-yl-piperazine-1-carboxamidine hydrochloride 518. MH$^+$ 427; $^1$HNMR (DMSO d6) δ9.20 (m, 2H), 8.60 (m, 2H), 8.15 (m, 3H), 7.60 (m, 5H), 4.60 (m, 2H), 3.9 (m, 6H).

Example 35

N-Pyridin-3-yl-piperazine-1-carboxamidine trifluoroacetate 520

In accordance with the general Scheme 2A, the following is the preparation of a compound of Structure 4A, wherein each of $R^{2a}$, $R^{2b}$ and $R^{2c}$ is hydrogen, m=2, n=1; Z is N; and Y is N-pyridin-3-yl-carboxamidine.

A mixture of 1-(3-pyridyl)thiourea (3.45 g, 22.5 mmol), N-tert-butoxycarbonyl-piperazine (4.60 g, 24.7 mmol) and 1,3-dicyclohexylcarbodiimide (5.40 g, 26.2 mmol) in anhydrous tetrahydrofuran (150 mL) under a nitrogen atmosphere was refluxed for 48 h, cooled to room temperature and the solvent removed under reduced pressure to yield an oily residue. The only residue was triturated with water (2×50 mL) and filtered. The aqueous filtrate was concentrated to give a white solid (1.50 g). The resulting white solid was suspended in toluene and sonicated, the precipitate was filtered and the filtrate concentrated under reduced pressure yielding a pale solid (920 mg).

The resulting pale solid (378 mmol) was treated with 50% trifluoroacetic acid/dichloromethane for 3 h. Removal of the solvent followed by trituration with methyl tert-butyl ether yielded the desired product as a crystalline solid that was collected by filtration and dried under vacuum 520. (MH$^+$ 206).

Example 36

4-(2-Naphthalen-1-yl-5-oxo-oxazol-4-ylidenemethyl)-N-pyridin-3-yl-Piperazine-1-carboxamidine hydrochloride 522

In accordance with the general Scheme 2A, the following is the preparation of a compound of Structure 5A, wherein each of $R^{2a}$, $R^{2b}$ and $R^{2c}$ is hydrogen, m=2, n=1; Z is N; Y is N-pyridin-3-yl-carboxamidine; and $R^1$ is naphthyl.

To a solution of 520 (346 mg, 0.63 mmol), prepared as described in Example 35, in anhydrous tetrahydrofuran (5 mL), triethylamine (600 mL, 3.1 mmol) was added, followed by a solution of 4-ethoxymethylene-2-naphthalen-1-yl-4H-oxazol-5-one (169 mg, 0.63 mmol) in tetrahydrofuran (3 mL). The mixture was stirred for 30 min and the volatile materials were removed under reduced pressure to yield residue. The resulting residue was dissolved in tetrahydrofuran (5 mL) and 4 M hydrochloric acid in dioxane (2 mL) added. The resulting precipitate was collected by filtration, washed with 20% diethyl ether/methyl tert-butyl ether and dried under vacuum to yield the desired product as its hydrochloride salt 522 (43 mg). $MH^+$ 427; $^1H$ NMR ($CD_3OD$) δ9.28 (d, 1H), 8.50 (m, 2H), 8.15 (m, 1H), 8.03 (m, 1H), 7.98 (m, 1H), 7.78 (m, 1H), 7.60 (m, 4H), 7.45 (s, 1H), 4.85 (m, 2H), 3.9 (m, 6H).

Example 37

4-(2-Naphthalen-1-yl-5-oxo-oxazol-4-ylidenemethyl)-N-pyrimidin-2-yl-piperazine-1-carboxamidine hydrochloride 524

In accordance with the general Scheme 3A, the following is the preparation of a compound of Structure 5A, wherein each of $R^{2a}$, $R^{2b}$ and $R^{2c}$ is hydrogen, m=2, n=1; Z is N; Y is N-pyrimidin-2-yl-carboxamidine; and $R^1$ is naphthyl.

A mixture 1H-pyrrole-1-carboxamidine hydrochloride (4.40 g, 30 mmol), N-tert-butoxycarbonyl piperazine (5.59 g, 30 mmol) and N,N-diisopropylethylamine (6.3 mL, 36 mmol) in 2-propanol (50 mL) was refluxed for 24 h, cooled to room temperature and the solvents were removed under reduced pressure. The residue was suspended in acetonitrile (50 mL) and filtered; the white precipitate was washed with acetonitrile (50 mL) and dried under vacuum to yield N-tert-butoxycarbonyl piperazine-1-carboxamidine (6.20 g).

To a mixture of N-tert-butoxycarbonyl piperazine-1-carboxamidine (228 mg, 1 mmol) and 2-chloropyrimidine (172 mg, 1.5 mmol) in anhydrous dioxane (2 mL), 60% NaH (80 mg, 2 mmol) was added. The reaction mixture was refluxed for 2 h, cooled to room temperature and concentrated to give a yellow oil. The oil was washed with methyl tert-butyl ether, followed by water, to yield a yellow precipitate of the desired intermediate (113 mg).

The yellow precipitate was treated with 50% trifluoroacetic acid/dichloromethane (1.5 mL) at room temperature for 1 h. The solvents were removed under reduced pressure, the residue washed with methyl tert-butyl ether and dried under vacuum yielding the desired piperazine intermediate as its trifluoroacetate salt (204 mg).

To a solution of the piperazine intermediate (180 mg, 0.33 mmol) in anhydrous tetrahydrofuran (5 mL), triethylamine (200 mL, 1.6 mmol) was added, followed by a solution of 4-ethoxymethylene-2-naphthalen-1-yl-4H-oxazol-5-one (89 mg, 0.33 mmol) in tetrahydrofuran (3 mL). The mixture was stirred for 20 min and the volatile materials were removed under reduced pressure. The residue was dissolved in tetrahydrofuran (5 mL) and 4 M hydrochloric acid in dioxane (2 mL) was added. The resulting precipitate was collected by filtration, washed with 50% ethanol/methyl tert-butyl ether and dried under vacuum to yield the desired product (100 mg) as its hydrochloride salt 524 (43 mg). $M^+$ 428; $^1H$ NMR ($CD_3OD$) δ9.28 (d, 1H), 8.85 (d, 2H), 8.15 (d, 1H), 8.00 (m, 2H), 7.60 (m, 3H), 7.45 (s, 1H), 7.30 (m, 1H), 4.85 (m, 2H), 3.9 (m, 6H).

Similarly, substituting 2-chloropyrimidine with 2-chloropyrazine, 4.6-dichloropyrimidine and the like, and 4-ethoxymethylene-2-naphthalen-1-yl-4H-oxazol-5-one with other oxazolones, following the procedure described in Example 37, the following examples were prepared:

4-(2-Naphthalen-1-yl-5-oxo-oxazol-4-ylidenemethyl)-N-pyrazin-2-yl-piperazine-1-carboxamidine hydrochloride 526; $M^+$ 428; $^1H$ NMR ($CD_3OD$) δ9.20 (d, 1H), 8.75 (s, 1H), 8.55 (m, 2H), 8.15 (d, 1H), 7.90 (m, 2H), 7.50 (m, 3H), 7.40 (s, 1H), 1H), 4.70 (m, 2H), 3.85 (m, 6H); and N-(6-Chloro-pyrimidin-4-yl)-4-(2-naphthalen-1-yl-5-oxo-oxazol-4-ylidenemethyl)-piperazine-1-carboxamidine hydrochloride 528; $M^+$ 461.97; $^1H$ NMR (DMSO d6) δ9.30 (br. s, 1H), 9.20 (d, 1H), 8.80 (s, 1H), 8.1 (m, 3H), 7.70 (m, 4H), 7.40 (s, 1H), 4.60 (m, 2H), 3.95 (m, 6H).

Example 38

4-(4-Amino-piperidin-1-ylmethylene)-2-naphthalen-1-yl-4H-oxazol-5-one 530

In accordance with the general Scheme 3A, the following is the preparation of a compound of Structure 5A, wherein each of $R^{2a}$, $R^{2b}$ and $R^{2c}$ is hydrogen, m=2, n=1; Z is CH; Y is amino; and $R^1$ is naphthyl.

To a solution of 4-ethoxymethylene-2-naphthalen-1-yl-4H-oxazol-5-one (6.30 g, 23.7 mmol) in tetrahydrofuran, piperidin-4-yl-carbamic acid tert-butyl ester (4.70 g, 23.7 mmol) was added, and the mixture was stirred at room temperature for 24 h. The reaction mixture was concentrated under reduced pressure to yield [1-(2-naphthalen-1-yl-5-oxo-oxazol-4-ylidenemethyl)-piperidin-4-yl]-carbamic acid tert-butyl ester.

[1-(2-naphthalen-1-yl-5-oxo-oxazol-4-ylidenemethyl)-piperidin-4-yl]-carbamic acid tert-butyl ester was stirred overnight in 20% trifluoroacetic acid/dichloromethane at room temperature. Neutralization with triethylamine afforded a precipitate that was collected by filtration, washed with cold methyl tert-butyl ether and dried under vacuum yielding the desired product 530 (6.70 g), ($MH^+$ 322).

Example 39

4-(4-Aminomethyl-piperidin-1-ylmethylene)-2-naphthalen-1-yl-4H-oxazol-5-one 532

In accordance with the general Scheme 3A, the following is the preparation of a compound of Structure 5A, wherein each of $R^{2a}$, $R^{2b}$ and $R^{2c}$ is hydrogen, m=2, n=1; Z is CH; Y is aminomethyl; and $R^1$ is naphthyl.

To a solution of 4-ethoxymethylene-2-naphthalen-1-yl-4H-oxazol-5-one (11.40 g, 43 mmol) in tetrahydrofuran, benzylidene-piperidin-4-ylmethyl-amine (8.60 g, 43 mmol) was added, and the mixture was stirred at room temperature for 24 h. The reaction mixture was concentrated under reduced pressure to yield 4-{4-[(benzylidene-amino)-methyl]-piperidin-1-ylmethylene}-2-naphthalen-1-yl-4H-oxazol-5-one.

4-{4-[(benzylidene-amino)-methyl]-piperidin-1-ylmethylene}-2-naphthalen-1-yl-4H-oxazol-5-one was stirred overnight in 20% trifluoroacetic acid, 10% water in dichloromethane at room temperature. The resulting mixture was neutralized using aqueous sodium carbonate (250 mL), the resulting precipitate collected by filtration and washed with cold methyl tert-butyl ether. Recrystallization from dioxane yielded the desired product 532 (11.0 g); (MH$^+$ 336).

Example 40

Furan-2-carboxylic acid [1-(2-naphthalen-1-yl-5-oxo-oxazol-4-ylidenemethyl)-piperidin-4-yl]-amide 534

In accordance with the general Scheme 3A, the following is the preparation of a compound of Structure 5A, wherein each of $R^{2a}$, $R^{2b}$ and $R^{2c}$ is hydrogen, m=2, n=1; Z is CH; Y is furna-2-yl-amide; and $R^1$ is naphthyl.

A 0.5 M acetonitrile solution of N,N-diisopropylethylamine (200 µL) was added to a 1.25 M acetonitrile solution of 530 (200 µL), prepared as described in Example 38. A 0.25 M tetrahydrofuran solution of 2-furanoyl chloride (300 µL) was added, the reaction vessel sealed, and the mixture was maintained at 60° C. for 24 h. The volatile materials were removed under high vacuum to yield the desired product 534 (MH$^+$ 416).

Similarly, substituting 4-(4-amino-piperidin-1-ylmethylene)-2-naphthalen-1-yl-4H-oxazol-5-one with 4-(4-aminomethyl-piperidin-1-ylmethylene)-2-naphthalen-1-yl-4H-oxazol-5-one, and 2-furanoyl chloride with other acid chlorides, following the procedure described in Example 40, the following examples were prepared:

N-[1-(2-Naphthalen-1-yl-5-oxo-oxazol-4-ylidenemethyl)-piperidin-4-ylmethyl]-isobutyramide 536 (MH$^+$ 406);

N-[1-(2-Naphthalen-1-yl-5-oxo-oxazol-4-ylidenemethyl)-piperidin-4-yl]-isobutyramide 538 (MH$^+$ 392);

Cyclohexanecarboxylic acid [1-(2-naphthalen-1-yl-5-oxo-oxazol-4-ylidenemethyl)-piperidin-4-yl]-amide 540 (MH$^+$ 432);

3-Methyl-N-[1-(2-naphthalen-1-yl-5-oxo-oxazol-4-ylidenemethyl)-piperidin-4-ylmethyl]-butyramide 542 (MH$^+$ 420);

3-Methyl-N-[1-(2-naphthalen-1-yl-5-oxo-oxazol-4-ylidenemethyl)-piperidin-4-yl]-butyramide 544 (MH$^+$ 406);

Furan-2-carboxylic acid [1-(2-naphthalen-1-yl-5-oxo-oxazol-4-ylidenemethyl)-piperidin-4-ylmethyl]-amide 546 (MH$^+$ 430); and 2-Methoxy-N-[1-(2-naphthalen-1-yl-5-oxo-oxazol-4-ylidenemethyl)-piperidin-4-yl]-benzamide 548 (MH$^+$ 456).

Example 41

1-[1-(2-Naphthalen-1-yl-5-oxo-oxazol-4-ylidenemethyl)-piperidin-4-ylmethyl]-3-(3,4,5-trimethoxy-phenyl)-urea 550

In accordance with the general Scheme 3A, the following is the preparation of a compound of Structure 5A, wherein each of $R^{2a}$, $R^{2b}$ and $R^{2c}$ is hydrogen, m=2, n=1; Z is CH; Y is aminomethyl; and $R^1$ is naphthyl.

To a 1.25 M acetonitrile solution of 532 (200 µL), prepared as described in Example 39, a 0.5 M acetonitrile solution of N,N-diisopropylethylamine (200 µL) was added, followed by a 0.25 M tetrahydrofuran solution of 3,4,5-trimethoxy-phenyl isocyanate (300 µL). The reaction vessel was sealed and the mixture was maintained at 60° C. for 24 h, cooled to room temperature and the volatile materials removed under high vacuum yielding the desired product 550 (MH$^+$ 545).

Similarly, substituting 4-(4-amino-piperidin-1-ylmethylene)-2-naphthalen-1-yl-4H-oxazol-5-one for 4-(4-aminomethyl-piperidin-1-ylmethylene)-2-naphthalen-1-yl-4H-oxazol-5-one, and 3,4,5-trimethoxy-phenyl isocyanate with other isocyanates, following the procedure described in Example 41, the following examples were prepared:

1-Benzoyl-3-[1-(2-naphthalen-1-yl-5-oxo-oxazol-4-ylidenemethyl)-piperidin-4-yl]-urea 552 (MH$^+$ 470);

1-Cyclohexyl-3-[1-(2-naphthalen-1-yl-5-oxo-oxazol-4-ylidenemethyl)-piperidin-4-yl]-urea 554 (MH$^+$ 448);

1-[1-(2-Naphthalen-1-yl-5-oxo-oxazol-4-ylidenemethyl)-piperidin-4-yl]-3-phenethyl-urea 556 (MH$^+$ 470);

1-(2-Methoxy-phenyl)-3-[1-(2-naphthalen-1-yl-5-oxo-oxazol-4-ylidenemethyl)-piperidin-4-ylmethyl]-urea 558 (MH$^+$ 484);

3-{3-[1-(2-Naphthalen-1-yl-5-oxo-oxazol-4-ylidenemethyl)-piperidin-4-yl]-ureido}-propionic acid ethyl ester 560 (MH$^+$ 465);

1-(4-Methoxy-phenyl)-3-[1-(2-naphthalen-1-yl-5-oxo-oxazol-4-ylidenemethyl)-piperidin-4-yl]-urea 562 (MH$^+$ 471); and 1-[1-(2-Naphthalen-1-yl-5-oxo-oxazol-4-ylidenemethyl)-piperidin-4-yl]-3-phenyl-urea 564 (MH$^+$ 441).

Example 42

Naphthalene-2-sulfonic acid [1-(2-naphthalen-1-yl-5-oxo-oxazol-4-ylidenemethyl)-piperidin-4-ylmethyl]-amide 566

In accordance with the general Scheme 3A, the following is the preparation of a compound of Structure 5A, wherein each of $R^{2a}$, $R^{2b}$ and $R^{2c}$ is hydrogen, m=2, n=1; Z is CH; Y is naphthylsulfonamide; and $R^1$ is naphthyl.

To a 0.25 M acetonitrile solution of 532 (200 µL), prepared as described in Example 39, a 0.5 M acetonitrile solution of N,N-diisopropylethylamine (200 µL) was added, followed by a 0.25 M acetonitrile solution of naphthalene-2-sulfonyl chloride (300 µL). The reaction vessel was sealed and the mixture was maintained at room temperature for 24 h. The volatile materials were removed under high vacuum yielding the desired product 566 (MH$^+$ 526).

Similarly, substituting 4-(4-amino-piperidin-1-ylmethylene)-2-naphthalen-1-yl-4H-oxazol-5-one for 4-(4-aminomethyl-piperidin-1-ylmethylene)-2-naphthalen-1-yl-4H-oxazol-5-one, and naphthalene-2-sulfonyl chloride with other sulfonyl chlorides, following the procedure described in Example 42, the following examples were prepared:

5-Dimethylamino-naphthalene-1-sulfonic acid [1-(2-naphthalen-1-yl-5-oxo-oxazol-4-ylidenemethyl)-piperidin-4-ylmethyl]-amide 568 (MH$^+$ 570);

4-Fluoro-N-[1-(2-naphthalen-1-yl-5-oxo-oxazol-4-ylidenemethyl)-piperidin-4-ylmethyl]-benzenesulfonamide 570 (MH$^+$ 495);

Benzo[1,2,5]thiadiazole-4-sulfonic acid [1-(2-naphthalen-1-yl-5-oxo-oxazol-4-ylidenemethyl)-piperidin-4-ylmethyl]-amide 572 (MH$^+$ 434);

Naphthalene-2-sulfonic acid [1-(2-naphthalen-1-yl-5-oxo-oxazol-4-ylidenemethyl)-piperidin-4-yl]-amide 574 (MH$^+$ 513);

Quinoline-8-sulfonic acid [1-(2-naphthalen-1-yl-5-oxo-oxazol-4-ylidenemethyl)-piperidin-4-ylmethyl]-amide 576 (MH$^+$ 527);

4-Bromo-N-[1-(2-naphthalen-1-yl-5-oxo-oxazol-4-ylidenemethyl)-piperidin-4-ylmethyl]-benzenesulfonamide 578 (MH$^+$ 555);

5-Dimethylamino-naphthalene-1-sulfonic acid [1-(2-naphthalen-1-yl-5-oxo-oxazol-4-ylidenemethyl)-piperidin-4-yl]-amide 580 (MH+ 555).

Example 43

[1-(2-Naphthalen-1-yl-5-oxo-oxazol-4-ylidenemethyl)-piperidin-4-yl]-carbamic acid cyclopentyl ester 582

In accordance with the general Scheme 3A, the following is the preparation of a compound of Structure 5A, wherein each of $R^{2a}$, $R^{2b}$ and $R^{2c}$ is hydrogen, m=2, n=1; Z is CH; Y is cyclopentyl carbamate; and $R^1$ is naphthyl.

To a 0.25 M DMF solution of 530 (200 μL), prepared as described in Example 38, a 0.5 M tetrahydrofuran solution of N,N-diisopropylethylamine (200 μL) was added, followed by a 0.25 M tetrahydrofuran solution of cyclopentyl chloroformate (300 μL). The reaction vessel sealed and the mixture was maintained at room temperature for 24 h. The volatile materials were removed under high vacuum and the desired product utilized without further purification 582 (MH+ 434).

Similarly, substituting 4-(4-amino-piperidin-1-ylmethylene)-2-naphthalen-1-yl-4H-oxazol-5-one with 4-(4-aminomethyl-piperidin-1-ylmethylene)-2-naphthalen-1-yl-4H-oxazol-5-one, and cyclopentyl chloroformate with other chloroformates, following the procedure described in Example 43, the following examples were prepared:

[1-(2-Naphthalen-1-yl-5-oxo-oxazol-4-ylidenemethyl)-piperidin-4-ylmethyl]-carbamic acid methyl ester 584 (MH+ 394);

[1-(2-Naphthalen-1-yl-5-oxo-oxazol-4-ylidenemethyl)-piperidin-4-yl]-carbamic acid methyl ester 586 (MH+ 380);

[1-(2-Naphthalen-1-yl-5-oxo-oxazol-4-ylidenemethyl)-piperidin-4-yl]-carbamic acid isopropyl ester 588 (MH+ 408);

[1-(2-Naphthalen-1-yl-5-oxo-oxazol-4-ylidenemethyl)-piperidin-4-ylmethyl]-carbamic acid phenyl ester 590 (MH+ 456);

[1-(2-Naphthalen-1-yl-5-oxo-oxazol-4-ylidenemethyl)-piperidin-4-yl]-carbamic acid isobutyl ester 592 (MH+ 422);

[1-(2-Naphthalen-1-yl-5-oxo-oxazol-4-ylidenemethyl)-piperidin-4-yl]-carbamic acid phenyl ester 594 (MH+ 442); and

[1-(2-Naphthalen-1-yl-5-oxo-oxazol-4-ylidenemethyl)-piperidin-4-ylmethyl]-carbamic acid isopropyl ester 596 (MH+ 422).

Example 44

1-(2-Naphthalen-1-yl-5-oxo-oxazol-4-ylidenemethyl)-piperidine-4-carboxylic acid phenylamide 598

In accordance with the general Scheme 2A, the following is the preparation of a compound of Structure 5A, wherein each of $R^{2a}$, $R^{2b}$ and $R^{2c}$ is hydrogen, m=2, n=1; Z is CH; Y is N-phenylamide; and $R^1$ is naphthyl.

A mixture of aniline (372 mg, 4 mmol), N-tert-butoxycarbonyl-isonipecotic acid (917 mg, 4 mmol) and 1-(3-dimethylaminopropyl)-3-ethylcarbodiimide (1.80 g, 3 mmol) in dichloromethane (15 mL) was stirred at room temperature under an argon atmosphere overnight. The reaction mixture was diluted with dichloromethane and the organic solution was washed with cold 1 M aqueous hydrochloric acid, water, saturated aqueous sodium bicarbonate, brine, dried over anhydrous sodium sulphate, filtered and evaporated under reduced pressure. The residue was recrystallized from ether yielding a white solid (1.06 g).

The resulting white solid was treated with 50% trifluoroacetic acid/dichloromethane (15 mL) at room temperature overnight. The volatile materials were removed under high vacuum and the residue was azeotroped with toluene. To the resulting solid was added diethyl ether (15 mL) followed by triethylamine (1 mL), the mixture was set aside and the resulting precipitate collected by filtration.

To a solution of the resulting precipitate (406 mg, 2 mmol) in acetonitrile (8 mL), triethylamine (0.5 mL) was added, followed by a solution of 4-ethoxymethylene-2-naphthalen-1-yl-4H-oxazol-5-one (534 mg, 2 mmol) in acetonitrile (8 mL), and the resulting mixture was stirred at room temperature for 4 h. Concentration of the reaction mixture to approximately half its volume afforded a yellow precipitate that was collected by filtration and dried under vacuum yielding 1-(2-naphthalen-1-yl-5-oxo-oxazol-4-ylidenemethyl)-piperidine-4-carboxylic acid phenylamide 598 (500 mg). MH+ 426; $^1$H NMR: (DMSO d6): δ1.98 (m, 2H), 2.19 (m, 2H), 2.90 (m, 1H), 3.65 (t, 2H), 4.18 (d, 1H), 5.58 (d, 2H), 7.20 (m, 1H), 7.45 (m, 2H), 7.60 (s, 1H), 7.70 (m, 6H), 8.15 (m, 4H), 9.30 (d, 1H), 10.00 (s, 1H).

Example 45

[$^3$H]prazosin Binding (alpha 1-Adrenoceptor) Assay $alpha_{1A}$, $alpha_{1B}$, and $alpha_{1D}$adrenoceptor transfected CHO-K1 cells, prepared using the methods described in Chang et al. (1998) *FEBS Lett.* 422:279–283, were grown to confluence in T-162 tissue culture flasks in Ham's F-12 culture medium supplemented with 10% fetal bovine serum, geneticin (150 μg/mL) and streptomycin/penicillin (30 μg/mL/30 μg/mL) at 37° C. in 7% $CO_2$. Cells were harvested by incubating with phosphate-buffered saline (PBS) containing 30 μM EDTA for 5–10 min at 37° C. Cells were pelleted by centrifuging at 500×g for 5 min, the pelleted cells were homogenized (Polytron homogenizer) in 10 vols (w/v) of 50 mM Tris, 1 mM EDTA, (homogenisation buffer, pH 7.4 at 4° C.). The homogenate was centrifuged at 45,000×g for 20 min. The pellet was resuspended in the homogenizing buffer and rehomogenized. The resulting homogenate was centrifuged at 45,000×g for 20 min. The pellet was resuspended in 50 mM Tris buffer (pH 7.4 at 4° C.), aliquoted, frozen, and stored at −80° C. for further use.

The membranes were thawed at room temperature and diluted in assay buffer (50 mM Tris buffer at pH 4) at 37° C. and homogenized using the Polytron tissue disrupter. The membranes were incubated with the radioligand ([$^3$H] prazosin, NEN, 0.1–0.5 nM) and test compound at 37° C. for 30 min. The membranes were then filtered over polyethyleneimine-treated GF/B unifilter plates using a Packard Filtermate Harvester and washed with ice-cold 50 mM Tris-HCl, 1 mM EDTA buffer (3×3 sec. washes). Scintillation cocktail was added to the filter plates and bound radioligand determined by liquid scintillation spectrophotometry.

For each experiment, total binding (in the absence of any test or reference compounds) and non-specific binding (10 μM phentolamine) were determined. For each sample tested, the concentration producing 50% inhibition of binding ($IC_{50}$) and Hill Slope ($n_H$) was determined using iterative non-linear curve fitting techniques with Kaleidagraph (Synergy Software) or other appropriate software. If the radioligand $K_D$ was known, the inhibition dissociation constant ($K_i$) of each ligand was determined according to the method of Cheng and Prusoff (Cheng, Y-C. and Prusoff, W. H., *Biochem. Pharmacol.*, (1973), 22:3099–3108).

Proceeding as in Example 45, compounds of Formula (I) were tested and found to be selective alpha$_{1B}$-adrenoceptor antagonists.

Example 46

Rat In Vivo, Blood Pressure Assay

The following describes an in vivo assay for measuring the effect of test compounds on blood pressure in normotensive and spontaneously hypertensive rats.

Normotensive or spontaneously hypertensive rats (0.25 to 0.45 kg) were fasted for 18 h and anesthetized with ether. The right femoral vein was isolated and cannulated with a fluid filled polyethylene cannulae for bolus administration of test substances. The right femoral artery was isolated and cannulated with a fluid filled polyethylene cannula connected to an external pressure transducer for monitoring mean arterial blood pressure (MAP).

Following cannulation, rats are pretreated (intravenous route) with an angiotensin receptor antagonist, a beta-adrenergic receptor antagonist and an alpha$_2$-adrenergic receptor antagonist as described in Blue et al. (*Br. J. Pharmacol.* 120:107P).

The rats were placed in restrainers and allowed to recover from anesthesia. Following a 30–60 minute period for stabilization, the test compounds or vehicles were administered intravenously. Following the last dose of test compound, prazosin was optionally administered, i.v., to determine hypotensive effects obtained by non-subtype-selective blockade of alpha$_1$-adrenoceptors. Blood pressure and heart rate were monitored continuously for at least 4 h post-administration.

Proceeding as in Example 46, compounds of Formula (I) were tested and found to be considerably less potent than prazosin at producing blood pressure lowering effects.

Example 47

Pain Response to Radiant Heat in Neuropathic Rats

The following describes an in vivo assay for measuring the effect of test compounds on the pain response to radiant heat in neuropathic rats. Male Sprague-Dawley rats (Harlan, 240–300 g) were surgically prepared to have a chronic constriction injury (CCI) as described herein 13–15 days prior to testing. Rats were selected for the study according to the following criteria: ligated leg ($L_L$)latency −4 to 14 seconds; sham leg ($L_S$) latency −6 to 18 seconds; difference ($L_{Diff}=L_L-L_S$) –greater than 1.5 seconds. Selected rats were randomly assigned to treatment groups and dosed at 0 (vehicle, 10 mL/kg, 0.5% CMC, 30, 60, 100 or 300 μg/kg, i.p. After 1 hour post-dosing, rats were placed under inverted plastic cages on an elevated glass platform. For each rat, four trials of each of the following were performed: shone light on the left hind paw (sham) and recorded the latency when the paw was withdrawn; shone light on the right hind paw (ligated) and recorded the latency when the paw was withdrawn. Five minute intervals were allowed between trials. Hind paws were examined for redness and blistering after each test.

Proceeding as in Example 47, compounds of Formula I were tested and found to have a significant effect in the radiant heat assay.

Example 48

Cold Allodynia Response in Neuropathic Rats

The following describes an in vivo assay for measuring the effect of test compounds on the cold allodynia response in neuropathic rats.

Male Sprague-Dawley rats (Harlan, 160–200 g) were surgically prepared to have a chronic constriction injury (CCI) as described herein 6 days prior to testing. Rats were selected for the study according to the following criteria: 1) the average of two trials was less than or equal to 13 sec; and 2) there was consistency across the two trial scores. Animals were screened for hypersensitivy to cold on post-surgery days 4 through 10, and selected for inclusion in dose-response studies based on the criteria described herein. The pre-dose screening values were used as the animals' baseline cold allodynia scores.

Selected rats were tested twice in the cold bath assay described herein for a pre-dose baseline and randomly assigned to treatment groups and dosed at 0 (vehicle, 10 mL/kg, 0.5% CMC, 30, 100 or 300 μg/kg, i.p. After 1 hour and 3 hours post-dosing, rats were tested in the cold bath assay. For each rat, the assay was run once at 1 and 3 hours post-dose. The time to raise the rear leg was recorded in each trial. The maximal observing time in each trial was 20 seconds.

Proceeding as in Example 48, compounds of Formula (I) were tested and found to have a significant effect in the cold allodynia response assay.

Example 49

The following are representative pharmaceutical formulations containing a compound of Formula (I).

Tablet Formulation

The following ingredients are mixed intimately and pressed into single scored tablets.

| Ingredient | Quantity per tablet (mg) |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per tablet (mg) |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| colorings | 0.5 mg |
| distilled water | q.s to 100 mL |

Injectable Formulation

The following ingredients are mixed to form an injectable formulation.

| Ingredient | Amount |
|---|---|
| compound of this invention | 0.2 g |
| sodium acetate buffer solution, 0.4 M | 2. mL |
| HCl (1N) or NaOH (1N) | q.s. to suitable pH |
| water (distilled, sterile) | q.s. to 20 mL |

Topical Formulation

A topical formulation is prepared with the following ingredients:

| Ingredient | Amount (g) |
|---|---|
| compound of this invention | 10 |
| Span 60 | 2 |
| TWEEN ®60 | 2 |
| mineral oil | 5 |
| petrolatum | 5 |
| methyl paraben | 0.15 |
| propyl paraben | 0.05 |
| BHA (butylated hydroxy anisole) | 0.01 |
| distilled water | q.s to 100 mL |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
|---|---|
| compound of this invention | 500 mg |
| Witepsol ® H-15 | balance |

Nasal Spray Formulation

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–10 h.

What is claimed is:

1. A compound comprising the Formula (I):

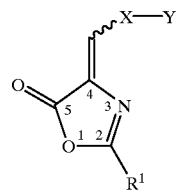

(I)

wherein:

X is Formula (A):

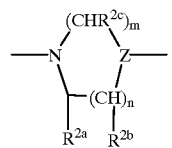

(A)

m is 2;

n is 1;

Y is —$(CH_2)_w$—$R^3$, —$(CH_2)_w$—CO—$R^4$, —$(CH_2)_w$—CO—NH—$R^5$, —$(CH_2)_w$—C($NR^6$)—NH—$R^7$, —$(CH_2)_w$—$SO_2$—$R^8$, —$(CH_2)_w$—NH—$R^9$, —$(CH_2)_w$—NH—CO—$R^{10}$, —$(CH_2)_w$—NH—CO—NH—$R^{11}$, or —$(CH_2)_w$—NH—$SO_2$—$R^{12}$; wherein w is an integer ranging from 0 to 3 inclusive;

Z is N;

$R^1$ is cycloalkyl, cycloalkenyl, heterocyclic, aryl or heteroaryl;

$R^{2a}$, $R^{2b}$ or $R^{2c}$ are each independently in each occurrence hydrogen, alkyl, alkenyl, cycloalkyl, aryl, or arylalkyl;

$R^3$ is heterocyclic or heteroaryl;

$R^4$, $R^5$, $R^8$, $R^9$, $R^{10}$, $R^{11}$ and $R^{12}$ are each independently in each occurrence hydrogen, alkyl, alkoxy, hydroxyalkyl, alkylthio, alkenyl, cycloalkyl, cycloalkylalkyl, cycloalkenyl, cycloalkenylalkyl, heterocyclic, heterocyclicalkyl, aryl, arylalkyl, heteroaryl or heteroarylalkyl;

$R^6$ and $R^7$ are each independently in each occurrence hydrogen, alkyl, hydroxyalkyl, alkenyl, cycloalkyl, cycloalkylalkyl, cycloalkenyl, cycloalkenylalkyl, heterocyclic, heterocyclicalkyl, aryl, arylalkyl, heteroaryl or heteroarylalkyl;

or an individual isomer or a racemic or non-racemic mixture of isomers, or a pharmaceutically acceptable salt or solvate thereof.

2. The compound of claim 1, wherein $R^1$ is aryl or heteroaryl; or an individual isomer or a racemic or non-racemic mixture of isomers, or a pharmaceutically acceptable salt or solvate thereof.

3. The compound of claim 1, wherein $R^1$ is an alkyl-, halo- or alkoxy-substituted phenyl, a bicyclic aryl or a bicyclic heteroaryl; or an individual isomer or a racemic or non-racemic mixture of isomers, or a pharmaceutically acceptable salt or solvate thereof.

4. The compound of claim 1, wherein $R^1$ is 3-methylphenyl, 3-chlorophenyl, 3-methoxyphenyl, naphthyl, fluoronaphthyl, thianaphthenyl, benzofuranyl, quinolinyl, indolyl, fluorobenzofuranyl, or benzimidazolyl; or an individual isomer or a racemic or non-racemic mixture of isomers, or a pharmaceutically acceptable salt or solvate thereof.

5. The compound of claim 3, wherein Y is —$(CH_2)_w$—$COR^4$, —$(CH_2)_w$—$SO_2R^8$, —$(CH_2)_w$—$NHR^9$, —$(CH_2)_w$—$NHCOR^{10}$, —$(CH_2)_w$—$NHCONHR^{11}$, or —$(CH_2)_w$—$NHSO_2R^{12}$; or an individual isomer or a racemic or non-racemic mixture of isomers, or a pharmaceutically acceptable salt or solvate thereof.

6. The compound of claim 5, wherein $R^1$ is 3-methylphenyl, 3-chlorophenyl, 3-methoxyphenyl, naphthyl, fluoronaphthyl, thianaphthenyl, benzofuranyl, quinolinyl, indolyl, fluorobenzofuranyl or benzimidazolyl; $R^4$ is alkyl, alkoxy, cycloalkyl, aryl, arylalkyl, heteroaryl, or heteroarylalkyl; $R^8$ and $R^{12}$ are alkyl, aryl, arylalkyl, or heteroaryl; $R^9$ is alkyl, arylalkyl, or heteroarylalkyl; $R^{10}$ is alkyl, alkoxy, cycloalkyl, aryl, arylalkyl, heteroaryl, or heteroarylalkyl; $R^{11}$ is alkyl, cycloalkyl, heterocyclicalkyl, aryl, arylalkyl, or heteroaryl; or an individual isomer or a racemic or non-racemic mixture of isomers, or a pharmaceutically acceptable salt or solvate thereof.

7. The compound of claim 1, wherein Y is —$(CH_2)_w$—$R^3$; or an individual isomer or a racemic or non-racemic mixture of isomers, or a pharmaceutically acceptable salt or solvate thereof.

8. The compound of claim 7 wherein, $R^1$ is aryl or heteroaryl; or an individual isomer or a racemic or non-racemic mixture of isomers, or a pharmaceutically acceptable salt or solvate thereof.

9. The compound of claim 7, wherein $R^1$ is an alkyl-, halo- or alkoxy-substituted phenyl, a bicyclic aryl or a bicyclic heteroaryl; or an individual isomer or a racemic or non-racemic mixture of isomers, or a pharmaceutically acceptable salt or solvate thereof.

10. The compound of claim 7, wherein $R^1$ is 3-methylphenyl, 3-chlorophenyl, 3-methoxyphenyl, naphthyl, fluoronaphthyl, thianaphthenyl, benzofuranyl, quinolinyl, indolyl, fluorobenzofuranyl or benzimidazolyl; or an individual isomer or a racemic or non-racemic mixture of isomers, or a pharmaceutically acceptable salt or solvate thereof.

11. The compound of claim 7, wherein $R^3$ is a moiety selected from benzooxazolyl, pyrazolyl, pyrimidyl, pyrrolyl, quinolinyl, isoquinolinyl, benzoisoquinolinyl dione, indolyl, imidazolyl, benzimidazolyl, imidazopyridinyl, oxazolyl, isooxazolyl, quinoxanilyl, thiazolyl, benzothiazolyl, or thiazolidinyl; wherein said moiety is optionally substituted with one or more of the following substituents: hydroxy, cyano, alkyl, alkoxy, thioalkyl, halo, haloalkyl, trifluoromethyl, hydroxyalkyl, alkoxycarbonyl, nitro, amino, alkylamino, dialkylamino, cycloalkyl, cycloalkylenyl, heterocyclic, aryl or heteroaryl; or an individual isomer or a racemic or non-racemic mixture of isomers, or a pharmaceutically acceptable salt or solvate thereof.

12. The compound of claim 1, wherein Y is —$(CH_2)_w$—CO—NH—$R^5$; or an individual isomer or a racemic or non-racemic mixture of isomers, or a pharmaceutically acceptable salt or solvate thereof.

13. The compound of claim 12, wherein $R^1$ is aryl or heteroaryl; or an individual isomer or a racemic or non-racemic mixture of isomers, or a pharmaceutically acceptable salt or solvate thereof.

14. The compound of claim 12, wherein $R^1$ is an alkyl-, halo- or alkoxy-substituted phenyl, a bicyclic aryl or a bicyclic heteroaryl; or an individual isomer or a racemic or non-racemic mixture of isomers, or a pharmaceutically acceptable salt or solvate thereof.

15. The compound of claim 12, wherein $R^1$ is 3-methylphenyl, 3-chlorophenyl, 3-methoxyphenyl, naphthyl, fluoronaphthyl, thianaphthenyl, benzofuranyl, quinolinyl, indolyl, fluorobenzofuranyl, or benzimidazolyl; or an individual isomer or a racemic or non-racemic mixture of isomers, or a pharmaceutically acceptable salt or solvate thereof.

16. The compound of claim 12, wherein $R^5$ is alkyl, cycloalkyl, heterocyclicalkyl, aryl, arylalkyl, or heteroaryl; or an individual isomer or a racemic or non-racemic mixture of isomers, or a pharmaceutically acceptable salt or solvate thereof.

17. The compound of claim 1, wherein Y is —$(CH_2)_w$—$C(NR^6)$—NH—$R^7$; or an individual isomer or a racemic or non-racemic mixture of isomers, or a pharmaceutically acceptable salt or solvate thereof.

18. The compound of claim 17, wherein $R^1$ is aryl or heteroaryl; or an individual isomer or a racemic or non-racemic mixture of isomers, or a pharmaceutically acceptable salt or solvate thereof.

19. The compound of claim 17, wherein $R^1$ is an alkyl-, halo- or alkoxy-substituted phenyl, a bicyclic aryl or a bicyclic heteroaryl; or an individual isomer or a racemic or non-racemic mixture of isomers, or a pharmaceutically acceptable salt or solvate thereof.

20. The compound of claim 17, wherein $R^1$ is 3-methylphenyl, 3-chlorophenyl, 3-methoxyphenyl, naphthyl, fluoronaphthyl, thianaphthenyl, benzofuranyl, quinolinyl, indolyl, fluorobenzofuranyl, or benzimidazolyl; or an individual isomer or a racemic or non-racemic mixture of isomers, or a pharmaceutically acceptable salt or solvate thereof.

21. The compound of claim 17, wherein $R^6$ is hydrogen, alkyl, cycloalkyl, aryl, arylalkyl, or heteroaryl; or an individual isomer or a racemic or non-racemic mixture of isomers, or a pharmaceutically acceptable salt or solvate thereof.

22. The compound of claim 21, wherein $R^6$ is hydrogen or alkyl; or an individual isomer or a racemic or non-racemic mixture of isomers, or a pharmaceutically acceptable salt or solvate thereof.

23. The compound of claim 17, wherein $R^7$ is hydrogen, alkyl, cycloalkyl, aryl, arylalkyl, or heteroaryl; or an individual isomer or a racemic or non-racemic mixture of isomers, or a pharmaceutically acceptable salt or solvate thereof.

24. The compound of claim 1, wherein the compound is:
4-(2-Naphthalen-1-yl-5-oxo-oxazol-4-ylidenemethyl)-piperazine-1-carboxylic acid phenylamide;
4-(2-Naphthalen-1-yl-5-oxo-oxazol-4-ylidenemethyl)-N-pyridin-2-yl-piperazine-1-carboxamidine;
4-(2-Naphthalen-1-yl-5-oxo-oxazol-4-ylidenemethyl)-N-phenyl-piperazine-1-carboxamidine;
4-[4-(1H-Benzoimidazol-2-yl)-piperazin-1-ylmethylene]-2-naphthalen-1-yl-4H-oxazol-5-one;
4-[2-(4-Fluoro-naphthalen-1-yl)-5-oxo-oxazol-4-ylidenemethyl]-piperazine-1-carboxylic acid phenylamide;
4-[2-(4-Fluoro-naphthalen-1-yl)-5-oxo-oxazol-4-ylidenemethyl]-N-pyridin-2-yl-piperazine-1-carboxamidine;

4-[2-(4-Fluoro-naphthalen-1-yl)-5-oxo-oxazol-4-ylidenemethyl]-N-phenyl-piperazine-1-carboxamidine;
4-[4-(1H-Benzoimidazol-2-yl)-piperazin-1-ylmethylene]-2-(4-fluoro-naphthalen-1-yl)-4H-oxazol-5-one;
4-[4-(4,5-Dihydro-1H-imidazol-2-yl)-piperazin-1-ylmethylene]-2-(4-fluoro-naphthalen-1-yl)-4H-oxazol-5-one;
4-[2-(7-Fluoro-benzofuran-4-yl)-5-oxo-oxazol-4-ylidenemethyl]-piperazine-1-carboxylic acid phenylamide;
4-[2-(7-Fluoro-benzofuran-4-yl)-5-oxo-oxazol-4-ylidenemethyl]-N-pyridin-2-yl-piperazine-1-carboxamidine;
4-[2-(7-Fluoro-benzofuran-4-yl)-5-oxo-oxazol-4-ylidenemethyl]-N-phenyl-piperazine-1-carboxamidine;
4-[4-(1H-Benzoimidazol-2-yl)-piperazin-1-ylmethylene]-2-(7-fluoro-benzofuran-4-yl)-4H-oxazol-5-one;
4-(2-Benzofuran-4-yl-5-oxo-oxazol-4-ylidenemethyl)-piperazine-1-carboxylic acid phenylamide;
4-(2-Benzofuran-4-yl-5-oxo-oxazol-4-ylidenemethyl)-N-pyridin-2-yl-piperazine-1-carboxamidine;
4-(2-Benzofuran-4-yl-5-oxo-oxazol-4-ylidenemethyl)-N-phenyl-piperazine-1-carboxamidine;
2-Benzofuran-4-yl-4-[4-(1H-benzoimidazol-2-yl)-piperazin-1-ylmethylene]-4H-oxazol-5-one;
4-[2-(2,3-Dihydro-benzofuran-4-yl)-5-oxo-oxazol-4-ylidenemethyl]-piperazine-1-carboxylic acid phenylamide;
4-[2-(2,3-Dihydro-benzofuran-4-yl)-5-oxo-oxazol-4-ylidenemethyl]-N-pyridin-2-yl-piperazine-1-carboxamidine;
4-[2-(2,3-Dihydro-benzofuran-4-yl)-5-oxo-oxazol-4-ylidenemethyl]-N-phenyl-piperazine-1-carboxamidine;
4-(2-Benzofuran-7-yl-5-oxo-oxazol-4-ylidenemethyl)-piperazine-1-carboxylic acid phenylamide;
4-(2-Benzofuran-7-yl-5-oxo-oxazol-4-ylidenemethyl)-N-pyridin-2-yl-piperazine-1-carboxamidine;
4-(2-Benzofuran-7-yl-5-oxo-oxazol-4-ylidenemethyl)-N-phenyl-piperazine-1-carboxamidine;
2-Benzofuran-7-yl-4-[4-(4,5-dihydro-1H-imidazol-2-yl)-piperazin-1-ylmethylene]-4H-oxazol-5-one;
4-[2-(2,3-Dihydro-benzofuran-7-yl)-5-oxo-oxazol-4-ylidenemethyl]-piperazine-1-carboxylic acid phenylamide;
4-[2-(2,3-Dihydro-benzo[1,4]dioxin-5-yl)-5-oxo-oxazol-4-ylidenemethyl]-N-pyridin-2-yl-piperazine-1-carboxamidine;
4-[4-(1H-Benzoimidazol-2-yl)-piperazin-1-ylmethylene]-2-(2,3-dihydro-benzo[1,4]dioxin-5-yl)-4H-oxazol-5-one;
2-(2,3-Dihydro-benzo[1,4]dioxin-5-yl)-4-[4-(4,5-dihydro-1H-imidazol-2-yl)-piperazin-1-ylmethylene]-4H-oxazol-5-one; or
an individual isomer, a racemic or non-racemic mixture of isomers, or a pharmaceutically acceptable salt or solvate thereof.

25. The compound of claim 24, wherein the compound is:
4-(2-Naphthalen-1-yl-5-oxo-oxazol-4-ylidenemethyl)-piperazine-1-carboxylic acid phenylamide;
4-(2-Naphthalen-1-yl-5-oxo-oxazol-4-ylidenemethyl)-N-pyridin-2-yl-piperazine-1-carboxamidine;
4-(2-Naphthalen-1-yl-5-oxo-oxazol-4-ylidenemethyl)-N-phenyl-piperazine-1-carboxamidine;
4-[4-(1H-Benzoimidazol-2-yl)-piperazin-1-ylmethylene]-2-naphthalen-1-yl-4H-oxazol-5-one;
4-[2-(4-Fluoro-naphthalen-1-yl)-5-oxo-oxazol-4-ylidenemethyl]-piperazine-1-carboxylic acid phenylamide;
4-[2-(4-Fluoro-naphthalen-1-yl)-5-oxo-oxazol-4-ylidenemethyl]-N-pyridin-2-yl-piperazine-1-carboxamidine;
4-[2-(4-Fluoro-naphthalen-1-yl)-5-oxo-oxazol-4-ylidenemethyl]-N-phenyl-piperazine-1-carboxamidine;
4-[4-(1H-Benzoimidazol-2-yl)-piperazin-1-ylmethylene]-2-(4-fluoro-naphthalen-1-yl)-4H-oxazol-5-one;
4-[2-(7-Fluoro-benzofuran-4-yl)-5-oxo-oxazol-4-ylidenemethyl]-piperazine-1-carboxylic acid phenylamide;
4-[2-(7-Fluoro-benzofuran-4-yl)-5-oxo-oxazol-4-ylidenemethyl]-N-pyridin-2-yl-piperazine-1-carboxamidine;
4-[2-(7-Fluoro-benzofuran-4-yl)-5-oxo-oxazol-4-ylidenemethyl]-N-phenyl-piperazine-1-carboxamidine;
4-[4-(1H-Benzoimidazol-2-yl)-piperazin-1-ylmethylene]-2-(7-fluoro-benzofuran-4-yl)-4H-oxazol-5-one;
4-(2-Benzofuran-4-yl-5-oxo-oxazol-4-ylidenemethyl)-piperazine-1-carboxylic acid phenylamide;
4-(2-Benzofuran-4-yl-5-oxo-oxazol-4-ylidenemethyl)-N-pyridin-2-yl-piperazine-1-carboxamidine;
4-(2-Benzofuran-4-yl-5-oxo-oxazol-4-ylidenemethyl)-N-phenyl-piperazine-1-carboxamidine;
2-Benzofuran-4-yl-4-[4-(1H-benzoimidazol-2-yl)-piperazin-1-ylmethylene]-4H-oxazol-5-one; or
an individual isomer, a racemic or non-racemic mixture of isomers, or a pharmaceutically acceptable salt or solvate thereof.

26. The compound of claim 25, wherein the compound is:
4-(2-Naphthalen-1-yl-5-oxo-oxazol-4-ylidenemethyl)-N-pyridin-2-yl-piperazine-1-carboxamidine;
4-(2-Naphthalen-1-yl-5-oxo-oxazol-4-ylidenemethyl)-N-phenyl-piperazine-1-carboxamidine;
4-[2-(4-Fluoro-naphthalen-1-yl)-5-oxo-oxazol-4-ylidenemethyl]-N-pyridin-2-yl-piperazine-1-carboxamidine;
4-[2-(4-Fluoro-naphthalen-1-yl)-5-oxo-oxazol-4-ylidenemethyl]-N-phenyl-piperazine-1-carboxamidine;
4-(2-Benzofuran-4-yl-5-oxo-oxazol-4-ylidenemethyl)-N-pyridin-2-yl-piperazine-1-carboxamidine;
4-(2-Benzofuran-4-yl-5-oxo-oxazol-4-ylidenemethyl)-N-phenyl-piperazine-1-carboxamidine; or
an individual isomer, a racemic or non-racemic mixture of isomers, or a pharmaceutically acceptable salt or solvate thereof.

27. A pharmaceutical composition comprising a therapeutically effective amount of the compound of claim 1, in admixture with one or more pharmaceutically acceptable non-toxic carriers.

28. The pharmaceutical composition of claim 27, wherein the compound is an alpha$_1$-adrenoceptor modulator.

29. The pharmaceutical composition of claim 28, wherein the alpha$_1$-adrenoceptor modulator is an alpha$_1$-adrenoceptor antagonist.

30. The pharmaceutical composition of claim 29, wherein the alpha$_1$-adrenoceptor antagonist is an alpha$_{1B}$-adrenoceptor antagonist.

* * * * *